US008609649B2

(12) United States Patent
Agar et al.

(10) Patent No.: US 8,609,649 B2
(45) Date of Patent: Dec. 17, 2013

(54) COMPOSITIONS AND METHODS FOR THE DIAGNOSIS, TREATMENT, AND PREVENTION OF AMYOTROPHIC LATERAL SCLEROSIS AND RELATED NEUROLOGICAL DISEASES

(75) Inventors: Jeffrey N. Agar, Newton, MA (US); Gregory A. Petsko, Belmont, MA (US); Dagmar Ringe, Belmont, MA (US); Walter R. P. Novak, Waltham, MA (US)

(73) Assignee: Brandeis University, Waltham, MA (US)

(*) Notice: Subject to any disclaimer, the term of this patent is extended or adjusted under 35 U.S.C. 154(b) by 750 days.

(21) Appl. No.: 12/532,309

(22) PCT Filed: Mar. 20, 2008

(86) PCT No.: PCT/US2008/057699
§ 371 (c)(1),
(2), (4) Date: Jan. 15, 2010

(87) PCT Pub. No.: WO2008/116092
PCT Pub. Date: Sep. 25, 2008

(65) Prior Publication Data
US 2010/0152125 A1 Jun. 17, 2010

Related U.S. Application Data

(60) Provisional application No. 60/895,822, filed on Mar. 20, 2007.

(51) Int. Cl.
A61K 31/7034 (2006.01)
A61K 31/195 (2006.01)
A61K 31/343 (2006.01)
A61K 31/55 (2006.01)
A61K 31/4015 (2006.01)
A61K 31/4709 (2006.01)
A61K 31/415 (2006.01)
A61K 31/416 (2006.01)
A61K 31/4439 (2006.01)
A61K 31/15 (2006.01)

(52) U.S. Cl.
USPC ...... 514/212.01; 514/314; 514/338; 514/404; 514/405; 514/423; 514/469; 514/562; 514/639

(58) Field of Classification Search
None
See application file for complete search history.

(56) References Cited

U.S. PATENT DOCUMENTS

2003/0045575 A1* 3/2003 Gwag et al. ............ 514/539
2004/0138153 A1 7/2004 Ramesh et al.
2007/0207093 A1* 9/2007 Bryant et al. ............ 424/49

FOREIGN PATENT DOCUMENTS

WO WO-02/072542 A2 9/2002
WO WO-2004/041793 A1 5/2004

OTHER PUBLICATIONS

John W. Baynes, The Role of AGEs in Aging: Causation or Correlation, 36 Experimental Gertontology 1527-1537 (2001).*
Nilus et al., Transient Receptor Potential Cation Channels in Disease, 87 Physiol Rev. 165-217 (2007).*
Reddy & Beyaz, Inhibitors of the Maillard reaction and AGE breakers as therapeutics for multiple diseases, 11(13/14) Drug Discovery Today, 646-654 (Jul. 2006).*
Rahbar et al., Novel Inhibitors of Advanced Glycation Endproducts (Part II), 3 Mol. Cell. Biol. Res. Commun. 360-366 (2000).*
Auclair, J. R. et al., "Strategies for stabilizing superoxide dismutase (SOD1), the protein destabilized in the most common form of familial amyotrophic lateral sclerosis", *PNAS*, 107(50):21394-21399 (Dec. 14, 2010).
Cheroni, C. et al., "Accumulation of human SOD1 and ubiquitinated deposits in the spinal cord of DOS1G93A mice during motor neuron disease progression correlated with a decrease of proteasome", *Neurobiology of Disease*, 18:509-522 (Elsevier, Inc. 2005).
Fel'Dman, I. Kh. et al., "Amino sulfides and amino sulfones. XXVII. Synthesis of some sulfonamides of salicylic acid", *Zhurnal Obshchei Khimii*, 33:394-396 (1963) (XP002653604, Database Accession No. 1963:415274, Chemical Abstracts Service, Columbus, OH, USA).
Friedlich, A. L. et al., "Effects of inducible nitric oxide synthase inhibitors in a transgenic model of amytrophic lateral sclerosis", XP002653606, Database Biosys Accession No. PREV200100075646, Biosciences Information Service, Philadelphia, PA, USA, 2000).
Kabashi, E. et al., "Focal dysfunction of the proteasome: a pathogenic factor in a mouse model of amyotrophic lateral sclerosis", *Journal of Neurochemistry*, 89:1325-1335 (International Society of Neurochemistry, 2004).

(Continued)

Primary Examiner — Janet L Andres
Assistant Examiner — Timothy R Rozof
(74) Attorney, Agent, or Firm — Foley Hoag LLP

(57) ABSTRACT

One aspect of the invention relates to a method of treating or preventing a neurodegenerative disease, comprising the step of administering to a patient in need thereof a therapeutically effective amount of an inhibitor of the formation of advanced glycation end products. Another aspect of the invention relates to a proteasome activity-based screening assay to select compounds which may be useful for treating or preventing a neurodegenerative disease, and the materials used therein. Yet another aspect of the invention relates to molecules, and methods of use thereof, which bind at or adjacent to SOD-I Trp32, including molecules that bind in a site adjacent to SOD-I Trp32 whether or not it is oxidized, for treating or preventing neurodegenerative disease.

9 Claims, 16 Drawing Sheets

(56) References Cited

OTHER PUBLICATIONS

Kurosaki, R. et al., "Effect of angiotensin-coverting enzyme inhibitor perindopril on interneurons in MPTP-treated mice", *European Neuropsychopharmacology*, 15:57-67 (Elsevier B. V. 2005).

Mohamed, Y. A. et al., "Synthesis of some new salicylic acid-5-sulfonamides as possible antibacterial and analgesic agents", *Acta Pharmaceutica Jugoslavica*, 39(3):181-191 (1989) (XP002653603, Database Accession No. 1990:197735, Chemical Abstracts Service, Columbus, OH, USA).

Pandey, H. K. et al., "Antimicrobial studies of doped Pr (III) and Nd (III) ions in the solution of some N and O donor atom ligands", *International Journal of Chemical Sciences*, 4(1):55-60 (2006) (XP002653602, Database Accession No. 2006:598973, Chemical Abstracts Service, Columbus, OH, USA).

Stoppa, G. R. et al., Aminoguanidine prevented impairment of blood antioxidant system in insulin-dependent diabetic rate, *Life Sciences*, 78:1352-1361 (Elsevier Inc. 2005).

Zhang, H. et al., "Bicarbonate-dependent Peroxidase Activity of Human Cu,Zn-Superoxide Dismutase Induces Covalent Aggregation of Protein", *Journal of Biological Chemistry*, 278(26):24078-24089 (USA, 2003).

Supplementary European Search Report from European application No. EP 08744133 dated Jul. 28, 2011.

Huebschmann et al., "Diabetes and Advanced Glycoxidation End Products," Diabetes Care, 29(6):1420-1432 (2006).

\* cited by examiner

Figure 1

| Category of therapy: human studies | Most advanced stage of trials as relates to AGEs | Trial results | Safety concerns |
|---|---|---|---|
| Prevent AGE formation | | | |
| Therapeutic entity | | | |
| Aminoguanidine | Human, phase III | ↓ nephropathy, ↓ retinopathy | ↑ glomerulonephritis, ↓ vitamin B6, ↓ iNOS |
| Benfotiamine | Human, phase II | ↓ neuropathy | None reported |
| AR inhibitors (epalrestat, zopolrestat) | Human, phase II | ↓ AGE levels, ↓ neuropathy, ↑ esophageal motility | None reported |
| AGE cross-link disrupter | | | |
| Therapeutic entity | | | |
| ALT-711 (alagebrium chloride) | Human, phase III | ↓ arterial stiffness, ↓ pulse pressure, breaks cross-links formed by AGEs, ↑ diastolic heart function | None reported |
| Antihypertensive | | | |
| Therapeutic entity | | | |
| ARB | Human, phase III | ↓ macrophages in carotid artery plaque | ↓ GFR, rare angioedema |
| ACE inhibitor | Human, phase II | ↓ RAGE levels | ↓ GFR, rare angioedema |
| Dietary factors | | | |
| Therapeutic entity | | | |
| Low-AGE diet | Human data, stage N/A | ↓ AGE levels, ↓ C-reactive protein | None reported |
| Prevent AGE formation | | | |
| Therapeutic entity | | | |
| ALT-946 | Animal (diabetic rats) | ↓ nephropathy better than aminoguanidine | None reported |
| LR-90 | Animal (diabetic rats) | ↓ nephropathy, ↓ oxidative stress | ↑ weight gain |
| OPB 9195 | Animal (diabetic rats) | ↓ stenosis after vessel injury, ↓ nephropathy | ↓ vitamin B6 |
| PARP inhibitors | Animal (diabetic rats) | ↓ endothelial dysfunction, ↓ diastolic dysfunction, ↓ neuropathy | None reported |
| Pyridoxamine | Animal (diabetic rats) | ↓ nephropathy, ↓ cholesterol, ↓ weight | None reported |
| AGE cross-link disrupter | | | |
| Therapeutic entity | | | |
| PTB | Animal (diabetic rats) | ↓ AGEs | None reported |
| AGE binder | | | |
| Therapeutic entity | | | |
| Soluble RAGE | Animal (diabetic mice) | ↓ stenosis after vessel injury, ↓ neuropathy | None reported |
| Lysozyme | Animal (diabetic and apolipoprotein E-null mice) | ↓ AGEs, ↓ nephropathy, ↓ atherosclerosis | None reported |
| Antioxidants | | | |
| Therapeutic entity | | | |
| Green tea | Animal (diabetic rats) | ↑ AGEs, ↑ AGE cross-links | None reported |
| Vitamins E and C | Animal (diabetic rats) | ↑ AGEs, ↑ AGE cross-links | ↑ CV morbidity from vitamin E >400 IU |
| Oral hypoglycemic agents | | | |
| Therapeutic entity | | | |
| Metformin | Animal (diabetic rats) | ↓ AGEs, ↓ AGE cross-links | Lactic acidosis |
| Pioglitazone | In vitro | ↓ AGEs, ↓ AGE cross-links | ↑ hepatitis, ↑ CHF if susceptible |

AR, aldose reductase; CHF, congestive heart failure; CV, cardiovascular; GFR, glomerular filtration rate; iNOS, inducible nitric oxide synthase; PTB, N-phenacylthiazolium bromide; TZD, thiazolidinedione.

Figure 3

>pcDNA3_control-T7.ab1 (wtSOD1)

DNA sequence:
NNNNNNNNNNNNNNNNANNCNNNGCNGCGTCTGGGGTTTCCGTTGCAGTCCTC
GGAACCAGGACCTCGGCGTGGCCTAGCGAGTTATGGCGACGAAGGCCGTGTGC
GTGCTGAAGGGCGACGGCCCAGTGCAGGGCATCATCAATTTCGAGCAGAAGGA
AAGTAATGGACCAGTGAAGGTGTGGGGAAGCATTAAAGGACTGACTGAAGGCC
TGCATGGATTCCATGTTCATGAGTTTGGAGATAATACAGCAGGCTGTACCAGTG
CAGGTCCTCACTTTAATCCTCTATCCAGAAAACACGGTGGGCCAAAGGATGAA
GAGAGGCATGTTGGAGACTTGGGCAATGTGACTGCTGACAAAGATGGTGTGGC
CGATGTGTCTATTGAAGATTCTGTGATCTCACTCTCAGGAGACCATTGCATCAT
TGGCCGCACACTGGTGGTCCATGAAAAGCAGATGACTTGGGCAAAGGTGGAA
ATGAAGAAAGTACAAAGACAGGAAACGCTGGAAGTCGTTTGGCTTGTGGTGTA
ATTGGGATCGCCCAATAAACATTCCCTTGGATGTAGTCTGAGGCCCCTTAACTC
ATCTGTTATCCTGCTAGCTGTAGAAATGTATCCTGATAAACATTAAACACTGTA
ATCTTAAAAAAGGATCCACTANNAACNGCCGCCAGTGTGCTGGAATTCTGCAG
ATATCCATCACACTGGCGGCCGCTCGAGCATGCATCTAGAGGGCCCTATTCTAT
AGTGTCACCTAAATGCTAGAGCTCGCTGATCAGCCTCGACTGTGCCTTCTAGTT
GCCAGCCATCTGTTGTTTGCCCCTCCCCCGTGCCTTCCTTGACCCTGGAANGTGC
CACTCCCACTGTCCTTTCCTAATAAAATGAGGAAATTGCATCGCATTGTCTGAG
TAGGTGTCATTCNNTTN (SEQ ID NO.: 1)

protein sequence:
Met A T K A V C V L K G D G P V Q G I I N F E Q K E S N G P V K V W G S I K G L
T E G L H G F H V H E F G D N T A G C T S A G P H F N P L S R K H G G P K D E E
R H V G D L G N V T A D K D G V A D V S I E D S V I S L S G D H C I I G R T L V V
H E K A D D L G K G G N E E S T K T G N A G S R L A C G V I G I A Q Stop (SEQ ID NO.: 2)

Figure 4

>pcDNA3_S1-T7.ab1 (empty pcDNA-3 vector)

DNA sequence:
NNNNNNNNNNNNCGTTNNNGGGCCCTCTAGACTCGAGCGGCCGCCACTGTGCT
GGATATCTGCAGAATTCCACCACACTGGACTAGTGGATCCGAGCTCGGTACCA
AGCTTAAGTTTAAACCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCA
CTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAA
GACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCAT
TAAGCGCGGCGGGTGTGGTGGTTACGCGCAGCGTGACCGCTACACTTGCCAGC
GCCCTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGTG
CTTTACGGCACCTCGACCCCAAAAAACTTGATTAGGGTGATGGTTCACGTAGTG
GGCCATCGCCCTGATAGACGGTTTTTCGCCCTTTGACGTTGGAGTCCACGTTCTT
TAATAGTGGACTCTTGTTCCAAACTGGAACAACACTCAACCCTATCTCGGTCTA
TTCTTTTGATTTATAAGGGATTTTGCCGATTTCGGCCTATTGGTTAAAAAATGAG
CTGATTTAACAAAAATTTAACGCGAATTAATTCTGTGGAATGTGTGTCAGTTAN
GGTGTGGAAAGTCCCCAGGCTCCCCAGCANGCAGAAGTATGCAAAGCATGCAT
CTCAATTAGTCAGCAACCAGGTGTGGAAAGTCCCCAGGCTCCCNN (SEQ ID NO.: 3)

Figure 5

>pcDNA3_S2-T7.ab1 (G93A)

DNA sequence:
NNNNNNNNNNNNNNNNNNNNCTCCTGCAGCGTCTGGGGTTTCCGTTGCAGTCCT
CGGAACCAGGACCTCGGCGTGGCCTAGCGAGTTATGGCGACGAAGGCCGTGTG
CGTGCTGAAGGGCGACGGCCCAGTGCAGGGCATCATCAATTTCGAGCAGAAGG
AAAGTAATGGACCAGTGAAGGTGTGGGGAAGCATTAAAGGACTGACTGAAGG
CCTGCATGGATTCCATGTTCATGAGTTTGGAGATAATACAGCAGGCTGTACCAG
TGCAGGTCCTCACTTTAATCCTCTATCCAGAAAACACGGTGGACCAAAGGATGA
AGAGAGGCATGTTGGAGACTTGGGCAATGTGACTGCTGACAAAGATGCTGTGG
CCGATGTGTCTATTGAAGATTCTGTGATCTCACTCTCAGGAGACCATTGCATCA
TTGGCCGCACACTGGTGGTCCATGAAAAAGCAGATGACTTGGGCAAAGGTGGA
AATGAAGAAAGTACAAAGACAGGAAACGCTGGAAGTCGTTTGGCTTGTGGTGT
AATTGGGATCGCCCAATAAACATTCCCTTGGATGTAGTCTGAGGCCCCTTAACT
CATCTGTTATCCTGCTAGCTGTAGAAATGTATCCTGATAAACATTAAACACTGT
AATCTTAAAAAAGGATCCACTANNAACGGCCGCCAGTGTGCTGGAATTCTGCA
GATATCCATCACACTGGCGGCCGCTCGAGCATGCATCTAGAGGGCCCTATTCTA
TAGTGTCACCTAAATGCTAGAGCTCGCTGATCAGCCTCNACTGTGCCTTCTAGT
TGCCAGCCATCTGTTGNTTGCCCCTCCCCCGTGCCTTCCTTGACCCTGGAAGGTG
NCACTCCNACTGTCCNTTTCCTAATAAAATGAGGAAATTGNATCNCATTGNCTG
ANTANGTGNCATTCNNNTCTGGGGGGNNNNGNNGGGGGCNNNN (SEQ ID NO.: 4)

protein sequence:
Met A T K A V C V L K G D G P V Q G I I N F E Q K E S N G P V K V W G S I K G L
T E G L H G F H V H E F G D N T A G C T S A G P H F N P L S R K H G G P K D E E
R H V G D L G N V T A D K D A V A D V S I E D S V I S L S G D H C I I G R T L V V
H E K A D D L G K G G N E E S T K T G N A G S R L A C G V I G I A Q Stop (SEQ ID NO.: 5)

Figure 6

>pcDNA3_S3-T7.ab1 (W32F G93A)

DNA sequence:
NNNNNNNNNNNNNNNNNNNCTCCTGCAGCGTCTGGGGTTTCCGTTGCAGTCCTC
GGAACCAGGACCTCGGCGTGGCCTAGCGAGTTATGGCGACGAAGGCCGTGTGC
GTGCTGAAGGGCGACGGCCCAGTGCAGGGCATCATCAATTTCGAGCAGAAGGA
AAGTAATGGACCAGTGAAGGTGTTCGGAAGCATTAAAGGACTGACTGAAGGCC
TGCATGGATTCCATGTTCATGAGTTTGGAGATAATACAGCAGGCTGTACCAGTG
CAGGTCCTCACTTTAATCCTCTATCCAGAAAACACGGTGGACCAAAGGATGAA
GAGAGGCATGTTGGAGACTTGGGCAATGTGACTGCTGACAAAGATGCTGTGGC
CGATGTGTCTATTGAAGATTCTGTGATCTCACTCTCAGGAGACCATTGCATCAT
TGGCCGCACACTGGTGGTTCATGAAAAGCAGATGACTTGGGCAAAGGTGGAA
ATGAAGAAAGTACAAAGACAGGAAACGCTGGAAGTCGTTTGGCTTGTGGTGTA
ATTGGGATCGCCCAATAAACATTCCCTTGGATGTAGTCTGAGGCCCCTTAACTC
ATCTGTTATCCTGCTAGCTGTAGAAATGTATCCTGATAAACATTAAACACTGTA
ATCTTAAAAAAGGATCNNNNANTAACGN (SEQ ID NO.: 6)

protein sequence:
Met A T K A V C V L K G D G P V Q G I I N F E Q K E S N G P V K V F G S I K G L T
E G L H G F H V H E F G D N T A G C T S A G P H F N P L S R K H G G P K D E E R
H V G D L G N V T A D K D A V A D V S I E D S V I S L S G D H C I I G R T L V V H
E K A D D L G K G G N E E S T K T G N A G S R L A C G V I G I A Q Stop (SEQ ID NO.: 7)

Figure 7

>pcDNA3_S4-T7.ab1 (W32F)

DNA sequence:
NNNNNNNNNNNNNNNNNNNNCTCNGCNGCGTCTGGGGTTTCCGTTGCAGTCCTC
GGAACCAGGACCTCGGCGTGGCCTAGCGAGTTATGGCGACGAAGGCCGTGTGC
GTGCTGAAGGGCGACGGCCCAGTGCAGGGCATCATCAATTTCGAGCAGAAGGA
AAGTAATGGACCAGTGAAGGTGTTCGGAAGCATTAAAGGACTGACTGAAGGCC
TGCATGGATTCCATGTTCATGAGTTTGGAGATAATACAGCAGGCTGTACCAGTG
CAGGTCCTCACTTTAATCCTCTATCCAGAAAACACGGTGGGCCAAAGGATGAA
GAGAGGCATGTTGGAGACTTGGGCAATGTGACTGCTGACAAAGATGGTGTGGC
CGATGTGTCTATTGAAGATTCTGTGATCTCACTCTCAGGAGACCATTGCATCAT
TGGCCGCACACTGGTGGTCCATGAAAAGCAGATGACTTGGGCAAAGGTGGAA
ATGAAGAAAGTACAAAGACAGGAAACGCTGGAAGTCGTTTGGCTTGTGGTGTA
ATTGGGATCGCCCAATAAACATTCCCTTGGATGTAGTCTGAGGCCCCTTAACTC
ATCTGTTATCCTGCTAGCTGTAGAAATGTATCCTGATAAACATTAAACACTGTA
ATCTTAAAAAAGGATCCACTAGTAACGGCCGCCAGTGTGCTGGAATTCTGCAG
ATATCCATCACACTGGCGGCCGCTCGAGCATGCATCTAGAGGGCCCTATTCTAT
AGTGTCACCTAAATGCTAGAGCTCGCTGATCAGCCTCGACTGTGCCTTCTAGTT
GCCAGCCATCTGTTGTTTGCCCCTCCCCGTGCCTTCCTTGACCCTGGAAGGTGC
CACTCCTACTGTCCTTTCCTAATAAAATGAGGAAATTGCATCGCATTGTCTGAG
TANGTGTCATTCTATTCTGGGGGGTGGGGNGGGNCNGGACAGCNAGGGGGANN
(SEQ ID NO.: 8)

protein sequence:
Met A T K A V C V L K G D G P V Q G I I N F E Q K E S N G P V K V F G S I K G L T
E G L H G F H V H E F G D N T A G C T S A G P H F N P L S R K H G G P K D E E R
H V G D L G N V T A D K D G V A D V S I E D S V I S L S G D H C I I G R T L V V H
E K A D D L G K G G N E E S T K T G N A G S R L A C G V I G I A Q Stop (SEQ ID
NO.: 9)

```
                              SEQUENCE LISTING

<160> NUMBER OF SEQ ID NOS: 9

<210> SEQ ID NO 1
<211> LENGTH: 927
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(16)
<223> OTHER INFORMATION: a, c, t, g, unknown or other
<220> FEATURE:
<221> NAME/KEY: modified_base
<222> LOCATION: (18)..(19)
<223> OTHER INFORMATION: a, c, t, g, unknown or other
<220> FEATURE:
<221> NAME/KEY: modified_base
<222> LOCATION: (21)..(23)
<223> OTHER INFORMATION: a, c, t, g, unknown or other
<220> FEATURE:
<221> NAME/KEY: modified_base
<222> LOCATION: (26)
<223> OTHER INFORMATION: a, c, t, g, unknown or other
<220> FEATURE:
<221> NAME/KEY: modified_base
<222> LOCATION: (662)..(663)
<223> OTHER INFORMATION: a, c, t, g, unknown or other
<220> FEATURE:
<221> NAME/KEY: modified_base
<222> LOCATION: (667)
<223> OTHER INFORMATION: a, c, t, g, unknown or other
<220> FEATURE:
<221> NAME/KEY: modified_base
<222> LOCATION: (852)
<223> OTHER INFORMATION: a, c, t, g, unknown or other
<220> FEATURE:
<221> NAME/KEY: modified_base
<222> LOCATION: (923)..(924)
<223> OTHER INFORMATION: a, c, t, g, unknown or other
<220> FEATURE:
<221> NAME/KEY: modified_base
<222> LOCATION: (927)
<223> OTHER INFORMATION: a, c, t, g, unknown or other

<400> SEQUENCE: 1
nnnnnnnnnn nnnnnnannc nnngcngcgt ctggggtttc cgttgcagtc ctcggaacca      60
ggacctcggc gtggcctagc gagttatggc gacgaaggcc gtgtgcgtgc tgaagggcga     120
cggcccagtg cagggcatca tcaatttcga gcagaaggaa agtaatggac cagtgaaggt     180
gtggggaagc attaaaggac tgactgaagg cctgcatgga ttccatgttc atgagtttgg     240
agataataca gcaggctgta ccagtgcagg tcctcacttt aatcctctat ccagaaaaca     300
cggtgggcca aaggatgaag agaggcatgt tggagacttg gcaatgtga ctgctgacaa      360
```

```
agatggtgtg gccgatgtgt ctattgaaga ttctgtgatc tcactctcag gagaccattg    420
catcattggc cgcacactgg tggtccatga aaaagcagat gacttgggca aaggtggaaa    480
tgaagaaagt acaaagacag gaaacgctgg aagtcgtttg gcttgtggtg taattgggat    540
cgcccaataa acattcccct tggatgtagt cgaggcccct taactcatct gttatcctgc    600
tagctgtaga aatgtatcct gataaacatt aaacactgta atcttaaaaa aggatccact    660
annaacngcc gccagtgtgc tggaattctg cagatatcca tcacactggc ggccgctcga    720
gcatgcatct agagggcccc attctatagt gtcacctaaa tgctagagct cgctgatcag    780
cctcgactgt gccttctagt tgccagccat ctgttgtttg cccctccccc gtgccttcct    840
tgaccctgga angtgccact cccactgtcc tttcctaata aaatgaggaa attgcatcgc    900
attgtctgag taggtgtcat tcnnttn                                        927
```

<210> SEQ ID NO 2
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 3
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (17)..(19)
<223> OTHER INFORMATION: a, c, t, g, unknown or other
<220> FEATURE:
<221> NAME/KEY: modified_base
<222> LOCATION: (862)

<223> OTHER INFORMATION: a, c, t, g, unknown or other
<220> FEATURE:
<221> NAME/KEY: modified_base
<222> LOCATION: (892)
<223> OTHER INFORMATION: a, c, t, g, unknown or other
<220> FEATURE:
<221> NAME/KEY: modified_base
<222> LOCATION: (959)..(960)
<223> OTHER INFORMATION: a, c, t, g, unknown or other

<400> SEQUENCE: 3

```
nnnnnnnnnn nncgttnnng ggccctctag actcgagcgg ccgccactgt gctggatatc      60
tgcagaattc caccacactg gactagtgga tccgagctcg gtaccaagct taagtttaaa     120
ccgctgatca gcctcgactg tgccttctag ttgccagcca tctgttgttt gcccctcccc     180
cgtgccttcc ttgaccctgg aaggtgccac tcccactgtc ctttcctaat aaaatgagga    240
aattgcatcg cattgtctga gtaggtgtca ttctattctg ggggtgggg tggggcagga     300
cagcaagggg gaggattggg aagacaatag caggcatgct ggggatgcgg tgggctctat    360
ggcttctgag gcggaaagaa ccagctgggg ctctaggggg tatccccacg cgccctgtag    420
cggcgcatta agcgcggcgg gtgtggtggt tacgcgcagc gtgaccgcta cacttgccag    480
cgccctagcg cccgctcctt tcgctttctt cccttccttt ctcgccacgt tcgccggctt    540
tccccgtcaa gctctaaatc ggggctccc tttaggggtc cgatttagtg ctttacggca    600
cctcgacccc aaaaaacttg attagggtga tggttcacgt agtgggccat cgccctgata    660
gacggttttt cgcccttga cgttggagtc cacgttcttt aatagtggac tcttgttcca    720
aactggaaca cactcaacc ctatctcggt ctattctttt gatttataag ggattttgcc    780
gatttcggcc tattggttaa aaatgagct gatttaacaa aaatttaacg cgaattaatt    840
ctgtggaatg tgtgtcagtt anggtgtgga aagtccccag gctccccagc angcagaagt    900
atgcaaagca tgcatctcaa ttagtcagca accaggtgtg gaaagtcccc aggctcccnn    960
```

<210> SEQ ID NO 4
<211> LENGTH: 953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(19)
<223> OTHER INFORMATION: a, c, t, g, unknown or other
<220> FEATURE:
<221> NAME/KEY: modified_base
<222> LOCATION: (663)..(664)
<223> OTHER INFORMATION: a, c, t, g, unknown or other
<220> FEATURE:
<221> NAME/KEY: modified_base
<222> LOCATION: (786)
<223> OTHER INFORMATION: a, c, t, g, unknown or other
<220> FEATURE:
<221> NAME/KEY: modified_base
<222> LOCATION: (818)
<223> OTHER INFORMATION: a, c, t, g, unknown or other
<220> FEATURE:
<221> NAME/KEY: modified_base
<222> LOCATION: (857)
<223> OTHER INFORMATION: a, c, t, g, unknown or other
<220> FEATURE:
<221> NAME/KEY: modified_base
<222> LOCATION: (864)
<223> OTHER INFORMATION: a, c, t, g, unknown or other
<220> FEATURE:
<221> NAME/KEY: modified_base
<222> LOCATION: (872)
<223> OTHER INFORMATION: a, c, t, g, unknown or other

```
<220> FEATURE:
<221> NAME/KEY: modified_base
<222> LOCATION: (897)
<223> OTHER INFORMATION: a, c, t, g, unknown or other
<220> FEATURE:
<221> NAME/KEY: modified_base
<222> LOCATION: (901)
<223> OTHER INFORMATION: a, c, t, g, unknown or other
<220> FEATURE:
<221> NAME/KEY: modified_base
<222> LOCATION: (907)
<223> OTHER INFORMATION: a, c, t, g, unknown or other
<220> FEATURE:
<221> NAME/KEY: modified_base
<222> LOCATION: (912)
<223> OTHER INFORMATION: a, c, t, g, unknown or other
<220> FEATURE:
<221> NAME/KEY: modified_base
<222> LOCATION: (915)
<223> OTHER INFORMATION: a, c, t, g, unknown or other
<220> FEATURE:
<221> NAME/KEY: modified_base
<222> LOCATION: (919)
<223> OTHER INFORMATION: a, c, t, g, unknown or other
<220> FEATURE:
<221> NAME/KEY: modified_base
<222> LOCATION: (925)..(927)
<223> OTHER INFORMATION: a, c, t, g, unknown or other
<220> FEATURE:
<221> NAME/KEY: modified_base
<222> LOCATION: (937)..(940)
<223> OTHER INFORMATION: a, c, t, g, unknown or other
<220> FEATURE:
<221> NAME/KEY: modified_base
<222> LOCATION: (942)..(943)
<223> OTHER INFORMATION: a, c, t, g, unknown or other
<220> FEATURE:
<221> NAME/KEY: modified_base
<222> LOCATION: (950)..(953)
<223> OTHER INFORMATION: a, c, t, g, unknown or other

<400> SEQUENCE: 4
nnnnnnnnnn nnnnnnnnnc tcctgcagcg tctggggttt ccgttgcagt cctcggaacc      60
aggacctcgg cgtggcctag cgagttatgg cgacgaaggc cgtgtgcgtg ctgaagggcg     120
acggcccagt gcagggcatc atcaatttcg agcagaagga agtaatggac ccagtgaagg     180
tgtggggaag cattaaagga ctgactgaag gcctgcatgg attccatgtt catgagtttg     240
gagataatac agcaggctgt accagtgcag gtcctcactt taatcctcta tccagaaaac     300
acggtggacc aaaggatgaa gagaggcatg ttggagactt gggcaatgtg actgctgaca     360
aagatgctgt ggccgatgtg tctattgaag attctgtgat ctcactctca ggagaccatt     420
gcatcattgg ccgcacactg gtggtccatg aaaaagcaga tgacttgggc aaaggtggaa     480
atgaagaaag tacaaagaca ggaaacgctg gaagtcgttt ggcttgtggt gtaattggga     540
tcgcccaata acattccct tggatgtagt ctgaggcccc ttaactcatc tgttatcctg     600
ctagctgtag aaatgtatcc tgataaacat taaacactgt aatcttaaaa aaggatccac     660
tannaacggc cgccagtgtg ctggaattct gcagatatcc atcacactgg cggccgctcg     720
agcatgcatc tagagggccc tattctatag tgtcacctaa atgctagagc tcgctgatca     780
gcctcnactg tgccttctag ttgccagcca tctgttgntt gcccctcccc cgtgccttcc     840
ttgaccctgg aagtgncac tccnactgtc cntttcctaa taaaatgagg aaattgnatc     900
ncattgnctg antangtgnc attcnnntct gggggnnnn gnnggggcn nnn             953

<210> SEQ ID NO 5
<211> LENGTH: 154
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 5

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45

His Glu Phe Gly Asp Asn Thr Ala Gly Cys Thr Ser Ala Gly Pro His
 50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Ala Val Ala
                 85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150

<210> SEQ ID NO 6
<211> LENGTH: 668
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(18)
<223> OTHER INFORMATION: a, c, t, g, unknown or other
<220> FEATURE:
<221> NAME/KEY: modified_base
<222> LOCATION: (657)..(660)
<223> OTHER INFORMATION: a, c, t, g, unknown or other
<220> FEATURE:
<221> NAME/KEY: modified_base
<222> LOCATION: (662)
<223> OTHER INFORMATION: a, c, t, g, unknown or other
<220> FEATURE:
<221> NAME/KEY: modified_base
<222> LOCATION: (668)
<223> OTHER INFORMATION: a, c, t, g, unknown or other

<400> SEQUENCE: 6
nnnnnnnnnn nnnnnnnnct cctgcagcgt ctggggtttc cgttgcagtc ctcggaacca      60
ggacctcggc gtggcctagc gagttatggc gacgaaggcc gtgtgcgtgc tgaagggcga     120
cggcccagtg cagggcatca tcaatttcga gcagaaggaa agtaatggac cagtgaaggt     180
gttcggaagc attaaaggac tgactgaagg cctgcatgga ttccatgttc atgagtttgg     240
agataataca gcaggctgta ccagtgcagg tcctcacttt aatcctctat ccagaaaaca     300
cggtggacca aggatgaag agaggcatgt tggagacttg gcaatgtga ctgctgacaa      360 agatgctgtg gccgatgtgt ctattgaaga ttctgtgatc tcactctcag gagaccattg     420
catcattggc cgcacactgg tggttcatga aaaagcagat gacttgggca aggtggaaa      480 tgaagaaagt acaaagacag gaaacgctgg aagtcgtttg gcttgtggtg taattgggat     540
```

```
cgcccaataa acattccctt ggatgtagtc tgaggcccct taactcatct gttatcctgc    600
tagctgtaga aatgtatcct gataaacatt aaacactgta atcttaaaaa aggatcnnnn    660 antaacgn                                                             668
```

<210> SEQ ID NO 7
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Ala Thr Lys Ala Val Cys Val Leu Lys Gly Asp Gly Pro Val Gln
 1               5                  10                  15

Gly Ile Ile Asn Phe Glu Gln Lys Glu Ser Asn Gly Pro Val Lys Val
            20                  25                  30

Phe Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Ala Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 8
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(19)
<223> OTHER INFORMATION: a, c, t, g, unknown or other
<220> FEATURE:
<221> NAME/KEY: modified_base
<222> LOCATION: (23)
<223> OTHER INFORMATION: a, c, t, g, unknown or other
<220> FEATURE:
<221> NAME/KEY: modified_base
<222> LOCATION: (26)
<223> OTHER INFORMATION: a, c, t, g, unknown or other
<220> FEATURE:
<221> NAME/KEY: modified_base
<222> LOCATION: (913)
<223> OTHER INFORMATION: a, c, t, g, unknown or other
<220> FEATURE:
<221> NAME/KEY: modified_base
<222> LOCATION: (940)
<223> OTHER INFORMATION: a, c, t, g, unknown or other
<220> FEATURE:
<221> NAME/KEY: modified_base
<222> LOCATION: (944)
<223> OTHER INFORMATION: a, c, t, g, unknown or other

```
<220> FEATURE:
<221> NAME/KEY: modified_base
<222> LOCATION: (946)
<223> OTHER INFORMATION: a, c, t, g, unknown or other
<220> FEATURE:
<221> NAME/KEY: modified_base
<222> LOCATION: (954)
<223> OTHER INFORMATION: a, c, t, g, unknown or other
<220> FEATURE:
<221> NAME/KEY: modified_base
<222> LOCATION: (962)..(963)
<223> OTHER INFORMATION: a, c, t, g, unknown or other

<400> SEQUENCE: 8
nnnnnnnnnn nnnnnnnnnc tcngcngcgt ctggggtttc cgttgcagtc ctcggaacca      60
ggacctcggc gtggcctagc gagttatggc gacgaaggcc gtgtgcgtgc tgaagggcga     120
cggcccagtg cagggcatca tcaatttcga gcagaaggaa agtaatggac cagtgaaggt     180
gttcggaagc attaaaggac tgactgaagg cctgcatgga ttccatgttc atgagtttgg     240
agataataca gcaggctgta ccagtgcagg tcctcacttt aatcctctat ccagaaaaca     300
cggtgggcca aggatgaaag agaggcatgt tggagacttg gcaatgtga ctgctgacaa      360 agatggtgtg gccgatgtgt ctattgaaga ttctgtgatc tcactctcag agaccattg      420 catcattggc cgcacactgg tggtccatga aaaagcagat gacttgggca aggtggaaa     480 tgaagaaagt acaaagacag gaaacgctgg aagtcgtttg gcttgtggtg taattgggat    540
cgcccaataa acattccctt ggatgtagtc tgaggcccct taactcatct gttatcctgc    600
tagctgtaga aatgtatcct gataaacatt aaacactgta atcttaaaaa aggatccact    660
agtaacggcc gccagtgtgc tggaattctg cagatatcca tcacactggc ggccgctcga    720
gcatgcatct agagggccct attctatagt gtcacctaaa tgctagagct cgctgatcag    780
cctcgactgt gccttctagt tgccagccat ctgttgtttg ccctccccc gtgccttcct     840 tgaccctgga aggtgccact cctactgtcc tttcctaata aaatgaggaa attgcatcgc     900
attgtctgag tangtgtcat tctattctgg ggggtggggn gggncnggac agcnagggg     960 ann                                                                  963

<210> SEQ ID NO 9
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
                 20                  25                  30

Phe Gly Ser Ile Lys Gly Leu Thr Glu Gly Leu His Gly Phe His Val
             35                  40                  45

His Glu Phe Gly Asp Asn Thr Ala Gly Cys Thr Ser Ala Gly Pro His
         50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
                100                 105                 110
```

```
Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

COMPOSITIONS AND METHODS FOR THE DIAGNOSIS, TREATMENT, AND PREVENTION OF AMYOTROPHIC LATERAL SCLEROSIS AND RELATED NEUROLOGICAL DISEASES

RELATED APPLICATIONS

This application is the U.S. National Stage of International Patent Application No. PCT/US2008/057699, filed Mar. 20, 2008, which claims the benefit of U.S. Provisional Patent Application Ser. No. 60/895,822, filed Mar. 20, 2007, which both of which are hereby incorporated by reference in their entireties.

SEQUENCE LISTING

The instant application contains a Sequence Listing which has been submitted via EFS-Web and is hereby incorporated by reference in its entirety. Said ASCII copy, created on Dec. 18, 2009, is named BUG02201.txt, and is 16,534 bytes in size.

BACKGROUND

Amyotrophic lateral sclerosis (ALS), also called Lou Gehrig's disease, is a progressive neuromuscular disease that weakens and eventually destroys motor neurons (components of the nervous system that connect the brain with the skeletal muscles). Skeletal muscles are involved with voluntary movements, such as walking and talking. The motor neurons transmit the command to move from the brain to the skeletal muscles, which respond by contracting.

A person with ALS usually presents with problems in dexterity or gait resulting from muscle weakness, or with difficulty speaking or swallowing. Sphincter control, sensory function, intellectual ability, and skin integrity are preserved. Patients become paralyzed and often require ventilation and surgery to provide a new opening in the stomach (gastrostomy). Loss of respiratory function is ultimately the cause of death.

ALS is an adult onset neurodegenerative disease in which two percent of all cases are caused by mutations in the gene encoding copper/zinc superoxide dismutase (SOD-1). Rosen, D. R., Siddique, T., Patterson, D., Figlewicz, D. A., Sapp, P., Hentati, A., Donaldson, D., Goto, J., O'Regan, J. P., and Deng, H. X. (1993) Nature 362, 59-62. More than 100 mutations distributed throughout the structure of the protein introduce a toxic gain of function that decreases protein solubility, leading to aggregation and the formation of both detergent-insoluble SOD-1 and inclusions that are a histopathological hallmark of ALS. Shinder, G. A., Lacourse, M. C., Minotti, S., and Durham, H. D. (2001) J. Biol. Chem. 276, 12791-12796; Johnston, J. A., Dalton, M. J., Gurney, M. E., and Kopito, R. R. (2000) Proc. Natl. Acad. Sci. U.S.A. 97, 12571-12576; Shibata, N., Asayama, K., Hirano, A., and Kobayashi, M. (1996) Dev. Neurosci. 18, 492-498; Bruijn, L. I., Becher, M. W., Lee, M. K., Anderson, K. L., Jenkins, N. A., Copeland, N. G., Sisodia, S. S., Rothstein, J. D., Borchelt, D. R., Price, D. L., and Cleveland, D. W. (1997) Neuron 18, 327-338; Durham, H. D., Roy, J., Dong, L., and Figlewicz, D. A. (1997) J. Neuropathol. Exp. Neurol. 56, 523-530; Kato, S., Horiuchi, S., Liu, J., Cleveland, D. W., Shibata, N., Nakashima, K., Nagai, R., Hirano, A., Takikawa, M., Kato, M., Nakano, I., and Ohama, E. (2000) Acta Neuropathol. (Berl.) 100, 490-505; Aoki, M., Kato, S., Nagai, M., and Itoyama, Y. (2005) Neuropathology 25, 365-370.

It is known that a portion of fALS is linked to a genetic defect on chromosome 21. This gene codes for an enzyme called superoxide dismutase (SOD-1), an antioxidant that protects motor neurons from free radical damage. The nature of the toxic gain of function imparted by familial ALS (fALS)-causing SOD-1 mutations is not completely understood (reviewed in Shaw, B. F., and Valentine, J. S. (2007) Trends Biochem. Sci 32, 78-85). These mutations do, however, provide evidence that diverse and relatively minor changes in SOD-1 primary structure can cause fALS. Approximately ninety percent of ALS is sporadic, and it is plausible that post-translational modification of wild-type proteins affects structural changes analogous to those caused by point mutation. Bredesen, D. E., Ellerby, L. M., Hart, P. J., Wiedau-Pazos, M., and Valentine, J. S. (1997) Ann. Neurol. 42, 135-137. Indeed, Lewy body-like inclusions in sporadic ALS are immunoreactive with antibodies to SOD-1. Shibata, N., Hirano, A., Kobayashi, M., Siddique, T., Deng, H. X., Hung, W. Y., Kato, T., and Asayama, K. (1996) J. Neuropathol. Exp. Neurol. 55, 481-490; Shibata, N., Hirano, A., Kobayashi, M., Sasaki, S., Kato, T., Matsumoto, S., Shiozawa, Z., Komori, T., Ikemoto, A., and Umahara, T. (1994) Neurosci. Lett. 179, 149-152; Chou, S. M., Wang, H. S., and Komai, K. (1996) J. Chem. Neuroanat. 10, 249-258. It has also been demonstrated that oxidative post-translational modification of SOD-1 occurs in vivo with aging and in association with the fALS, Parkinson, and Alzheimer neurodegenerative diseases. Takata, I., Kawamura, N., Myint, T., Miyazawa, N., Suzuki, K., Maruyama, N., Mino, M., and Taniguchi, N. (1996) Biochem. Biophys. Res. Commun. 219, 243-248; Kato, S., Nakashima, K., Horiuchi, S., Nagai, R., Cleveland, D. W., Liu, J., Hirano, A., Takikawa, M., Kato, M., Nakano, I., Sakoda, S., Asayama, K., and Ohama, E. (2001) Neuropathology 21, 67-81; Shibata, N., Hirano, A., Kato, S., Nagai, R., Horiuchi, S., Komori, T., Umahara, T., Asayama, K., and Kobayashi, M. (1999) Acta Neuropathol. (Berl.) 97, 240-246; Kato, S., Horiuchi, S., Nakashima, K., Hirano, A., Shibata, N., Nakano, I., Saito, M., Kato, M., Asayama, K., and Ohama, E. (1999) Acta Neuropathol. (Berl.) 97, 260-266; Choi, J., Rees, H. D., Weintraub, S. T., Levey, A. I., Chin, L. S., and Li, L. (2005) J. Biol. Chem. 280, 11648-11655. There is also considerable evidence that fALS-causing mutations predispose SOD-1 to post-translational modifications, and that in vitro oxidative modification of SOD-1 induces aggregation Poon, H. F., Hensley, K., Thongboonkerd, V., Merchant, M. L., Lynn, B. C., Pierce, W. M., Klein, J. B., Calabrese, V., and Butterfield, D. A. (2005) Free Radic. Biol. Med. 39, 453-462; Andrus, P. K., Fleck, T. J., Gurney, M. E., and Hall, E. D. (1998) J. Neurochem. 71, 2041-2048; Tiwari, A., and Hayward, L. J. (2003) J. Biol. Chem. 278, 5984-5992; Zhang, H., Joseph, J., Crow, J., and Kalyanaraman, B. (2004) Free Radic. Biol. Med. 37, 2018-2026; Davies, K. J. (1987) J. Biol. Chem. 262, 9895-9901; and Rakhit, R., Cunningham, P., Furtos-Matei, A., Dahan, S., Qi, X. F., Crow, J. P., Cashman, N. R., Kondejewski, L. H., and Chakrabartty, A. (2002) J. Biol. Chem. 277, 47551-47556.

SUMMARY

One aspect of the invention relates to a method of treating or preventing a neurodegenerative disease, comprising the step of administering to a patient in need thereof a therapeutically effective amount of an inhibitor of the formation of advanced glycation end products. Another aspect of the invention relates to a proteasome activity-based screening assay to select compounds which may be useful for treating or preventing a neurodegenerative disease, and the materials used therein. Yet another aspect of the invention relates to molecules, and methods of use thereof, which bind at or adjacent to SOD-1 Trp32, including molecules that bind in a site adjacent to SOD-1 Trp32 whether oxidized or not, for treating or preventing neurodegenerative disease.

BRIEF DESCRIPTION OF THE FIGURES

FIG. 1 depicts a table summarizing therapeutic agents targeting advanced glycation endproducts. See Diabetes Care 2006, 29(6), 1424.

FIG. 3 depicts the nucleic acid and corresponding protein sequences of a pcDNA-3 vector with wild type SOD-1.

FIG. 4 depicts the nucleic acid sequence of a pcDNA-3 vector.

FIG. 5 depicts the nucleic acid and corresponding protein sequences of a pcDNA-3 vector with G93A SOD-1.

FIG. 6 depicts the nucleic acid and corresponding protein sequences of a pcDNA-3 vector with W32F G93A SOD-1.

FIG. 7 depicts the nucleic acid and corresponding protein sequences of a pcDNA-3 vector with W32F SOD-1.

DETAILED DESCRIPTION

Figure 2:
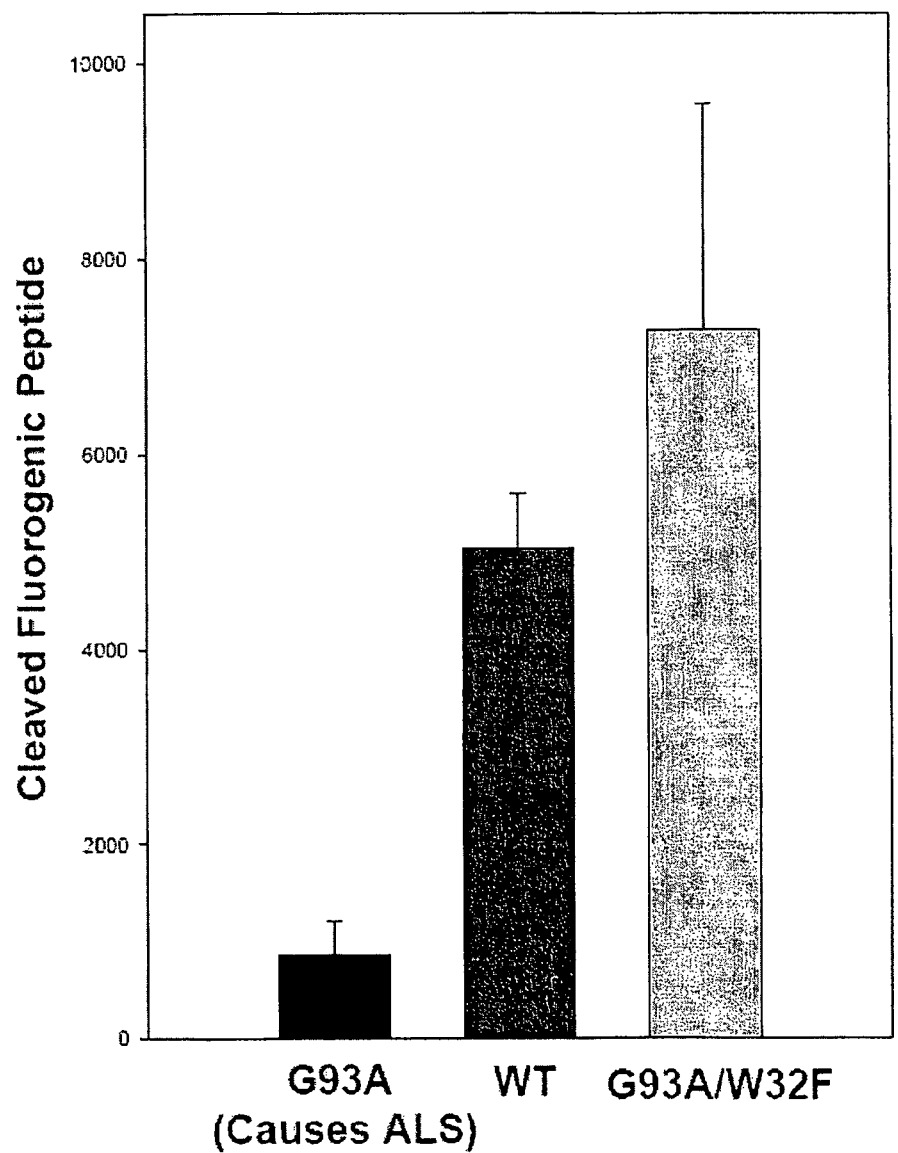
FIG. 2 illustrates proteasome activity in wild-type (WT) and mutated-SOD-1-expressing stably transfected monoclonal NIH/3T3 cell lines (i.e., G93A SOD-1-expressing clones; wild-type SOD-1-expressing clones; and W32F/G93A SOD-1 expressing clones), which can be used as a screening method for ALS therapeutic compounds.

One aspect of the invention relates to a method of treating or preventing a neurodegenerative disease, comprising the step of administering to a patient in need thereof a therapeutically effective amount of an inhibitor of the formation of advanced glycation end products. Another aspect of the invention relates to a proteasome activity-based screening assay to select compounds which may be useful for treating or preventing a neurodegenerative disease, and the materials used therein. Yet another aspect of the invention relates to molecules, and methods of use thereof, which bind at or adjacent to SOD-1 Trp32, including molecules that bind in a site adjacent to SOD-1 Trp32 whether oxidized or not, for treating or preventing neurodegenerative disease.

Advanced Glycation Endproduct Inhibitors

It is known that one familial form of amyotrophic lateral sclerosis, a neurodegenerative disease, is caused by gain-of-function mutations in the gene encoding copper/zinc superoxide dismutase (SOD-1). In vivo evidence disclosed herein reveals that normally occurring oxidative modification to SOD-1 promotes aggregation and toxicity of mutant proteins. The oxidation of tryptophan 32 (Trp-32) was identified as a normal modification being present in both wild-type enzyme and SOD-1 with the disease-causing mutation, G93A, isolated from erythrocytes. Mutating Trp-32 to a residue with a slower rate of oxidative modification, phenylalanine (Zhang, H., Andrekopoulos, C., Joseph, J., Chandran, K., Karoui, H., Crow, J. P., and Kalyanaraman, B. (2003) J. Biol. Chem. 278, 24078-24089), resulted in decreased cytotoxicity of a disease-causing mutant SOD-1 (SOD-1$^{G93A}$ or G93A SOD-1) in a motor neuronal cell culture model and decreased the propensity to form cytoplasmic inclusions.

Remarkably, as described herein, it has been discovered that suppression or prevention of oxidation of Trp32 in SOD-1 improves survival in ALS models. For a few background references see: Shibata N, Asayama K, Hirano A, Kobayashi M. Immunohistochemical study on superoxide dismutases in spinal cords from autopsied patients with amyotrophic lateral sclerosis. Dev. Neurosci. 1996; 18:492-498; Bruijn L I, Becher M W, Lee M K, et al. ALS-linked SOD1 mutant G85R mediates damage to astrocytes and promotes rapidly progressive disease with SOD1-containing inclusions. Neuron 1997; 18:327-338; Durham H D, Roy J, Dong L, Figlewicz D A. Aggregation of mutant Cu/Zn superoxide dismutase proteins in a culture model of ALS. J. Neuropathol. Exp. Neurol. 1997; 56:523-530; Kato S, Horiuchi S, Liu J, et al. Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation. Acta Neuropathol. (Berl) 2000; 100: 490-505; Aoki M, Kato S, Nagai M, Itoyama Y. Development of a rat model of amyotrophic lateral sclerosis expressing a human SOD1 transgene. Neuropathology 2005; 25:365-370; Shaw P J, Ince P G, Falkous G, Mantle D. Oxidative damage to protein in sporadic motor neuron disease spinal cord. Ann. Neurol. 1995; 38:691-695; Shinder G A, Lacourse M C, Minotti S, Durham H D. Mutant Cu/Zn-superoxide dismutase proteins have altered solubility and interact with heat shock/stress proteins in models of amyotrophic lateral sclerosis. J Biol. Chem. 2001; 276:12791-12796; Johnston J A, Dalton M J, Gurney M E, Kopito R R. Formation of high molecular weight complexes of mutant Cu, Zn-superoxide dismutase in a mouse model for familial amyotrophic lateral sclerosis. Proc. Natl. Acad. Sci. U.S.A 2000; 97:12571-12576; Wang J, Xu G, Borchelt D R. High molecular weight complexes of mutant superoxide dismutase 1: age-dependent and tissue-specific accumulation. Neurobiol. Dis. 2002; 9:139-148; Shibata N, Hirano A, Hedley-Whyte E T, et al. Selective formation of certain advanced glycation end products in spinal cord astrocytes of humans and mice with superoxide dismutase-1 mutation. Acta Neuropathol. (Berl) 2002; 104:171-178.

Figure 8:
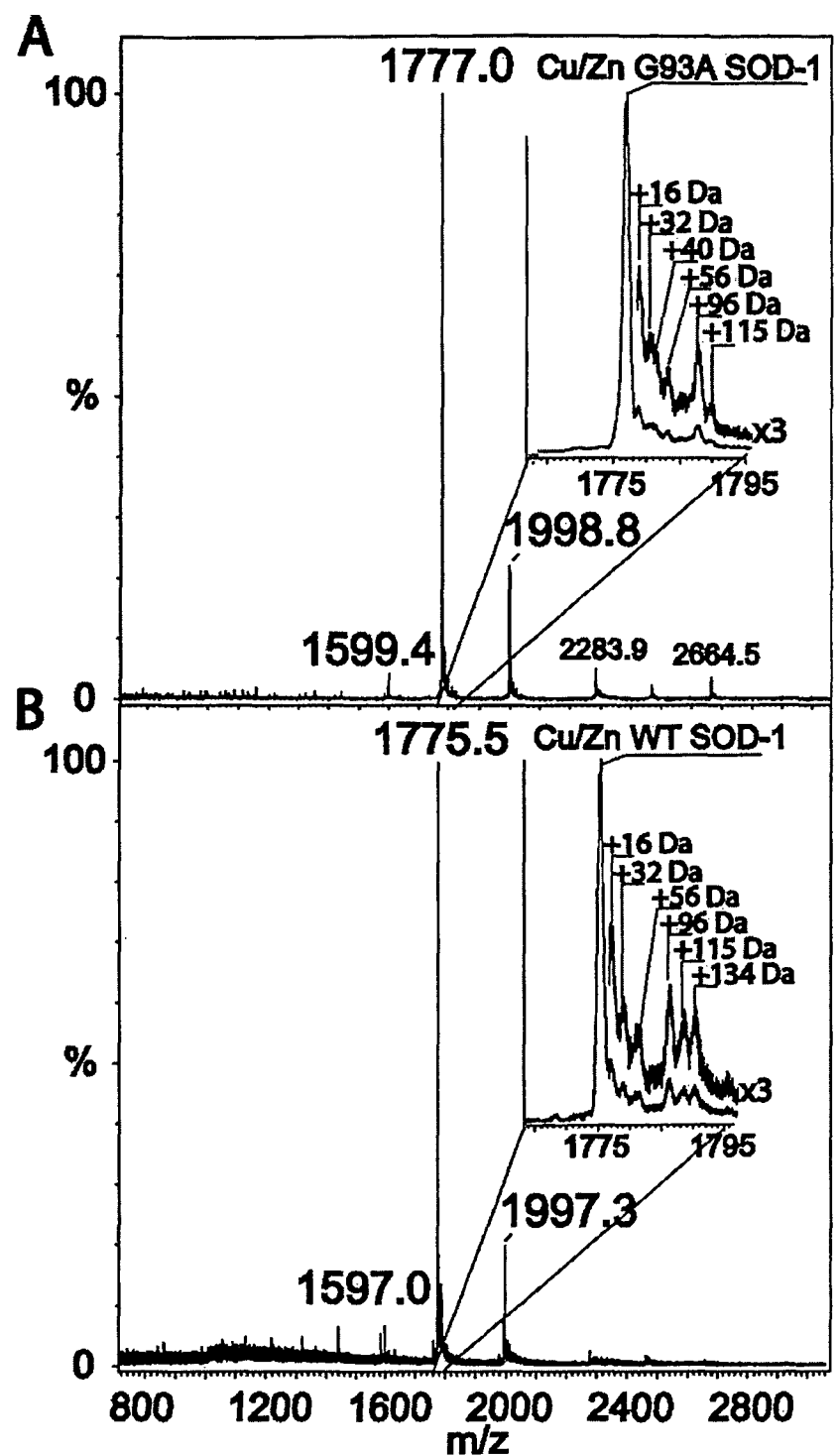
FIG. 8 depicts mass spectral evidence of as-isolated SOD-1 modifications. [A] SOD-1$^{G93A}$ purified from mouse blood and analyzed by nanoelectrospray ionization mass spectrometry. [B] hSOD-1$^{wt}$ purified from human blood and analyzed by nanoelectrospray ionization mass spectrometry. Inset panels show expansion of the +9 charge state (5 protons and two positive charges each on copper and zinc). Mass shifts (calculated as the change in mass/charge×a charge state of 9) observed in the intact protein indicate post-translational modification of SOD-1 by 1-6 oxygen atoms.

The results disclosed herein provide mass spectral evidence for the oxidation of Trp-32 in as-isolated SOD-1. Specifically, using immunoaffinity chromatography with antibodies raised against partially oxidized human SOD-1wt, SOD-1 was purified from human blood, and SOD-1wt and SOD-1G93A were purified from transgenic mouse blood. Intact SOD-1 was analyzed by infusion nanoelectrospray mass spectrometry, affording a survey of post-translational modifications. MS data demonstrate that SOD-1 purified from human and mouse erythrocytes was metallated and retained an intact intrasubunit disulfide. Previous studies of SOD-1G93A metallation in the unaffected organs, liver and kidney, also indicated full metallation. Jonsson, P. A., Graffmo, K. S., Andersen, P. M., Brannstrom, T., Lindberg, M., Oliveberg, M., and Marklund, S. L. (2006) Brain 129, 451-464. The mass-to-charge ratio of SOD-1 was consistent with the oxidation state of the metals being Cu(II) and Zn(II) (FIG. 8). Lei, Q. P., Cui, X., Kurtz, D. M., Jr., Amster, I. J., Chemushevich, I. V., and Standing, K. G. (1998) Anal. Chem. 70, 1838-1846; and Johnson, K. A., Verhagen, M. F., Brereton, P. S., Adams, M. W., and Amster, I. J. (2000) Anal. Chem. 72, 1410-1418. High resolution Fourier transform mass spectrometry (data not shown) in the presence and absence of tri-(2-carboxyethyl) phosphine confirmed the presence of an intrasubunit disulfide bridge. Aside from the expected metallation and disulfide, both SOD-1wt and SOD-1G93A were further post-translationally modified by the addition of between one and six oxygen atoms per monomer (FIG. 8, insets). Tiwari, A., and Hayward, L. J. (2003) J. Biol. Chem. 278, 5984-5992. Oxidatively modified SOD-1 consistently represented 20-30% of total as isolated SOD-1. Among the most prevalent modifications were SOD-1 modified by one and two oxygen atoms, representing 6 and 5% of total SOD-1, respectively.

Figure 9:
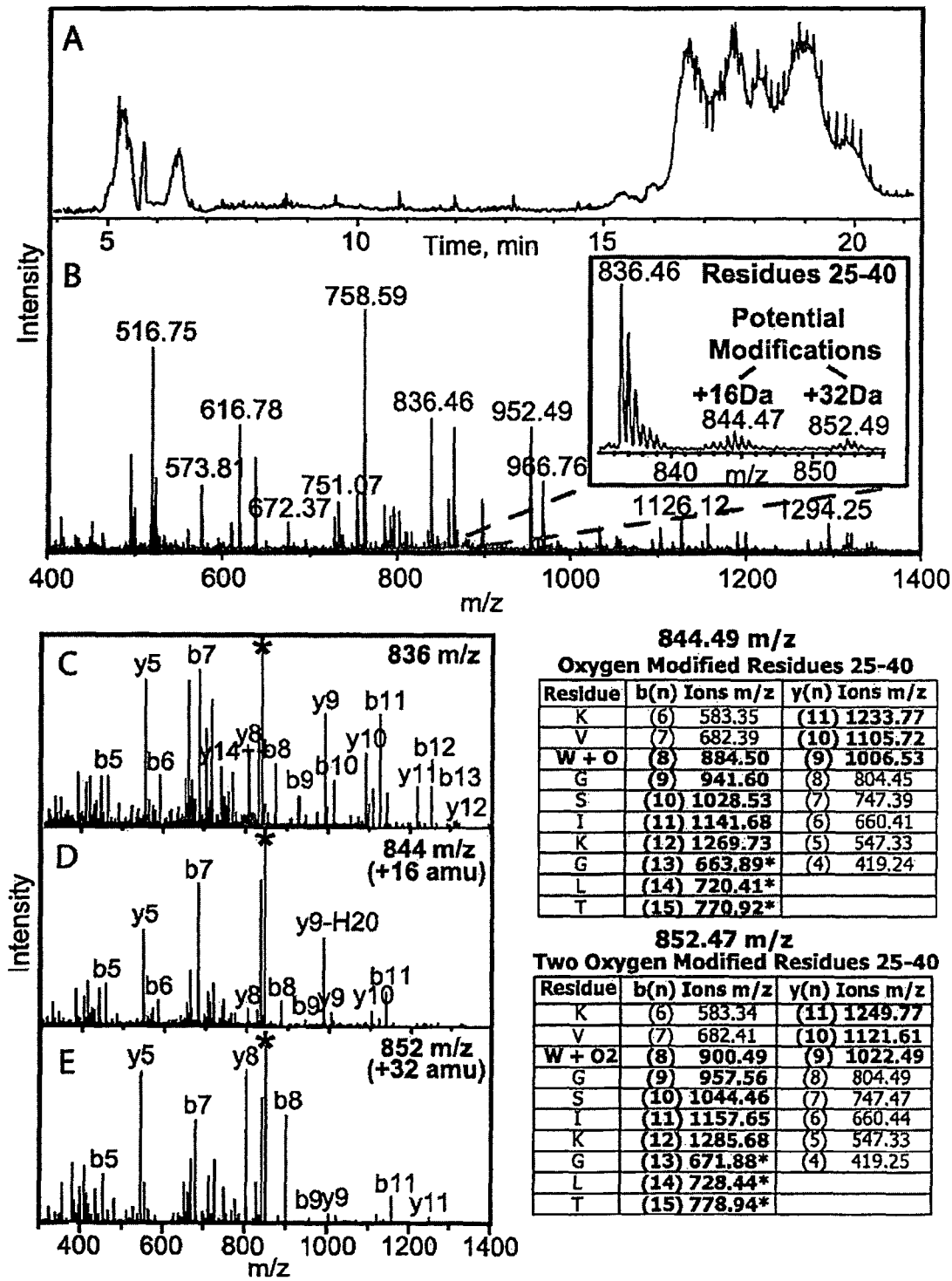
FIG. 9 depicts an LC-MS/MS identification of Trp-32 oxidative modification. Typical liquid chromatography-electrospray ionization-mass spectrometry experiment consisting of a total ion chromatogram [A] and a summation of all of the chromatographic peaks between 5 and 21 min [B]. The inset panel in [B] shows peaks corresponding to the net addition of both a single oxygen and two oxygen atoms to residues 25-40 were identified and localized to Trp-32 by comparing the CAD of molecules at 836 [C], 844 [D], and 852 [E] m/z. Assignments for experimentally observed CAD fragment ions of 844 and 852 m/z-modified residues are shown in respectively labeled tables, with oxygen-modified fragment ions in bold type. Modifications were observed in both the +2H$^+$ and +3H$^+$ charge states of residues 25-40 and in the +3H$^+$ charge state of residues 25-49, which contained one missed trypsin cleavage. The average difference between a given experimental CAD fragment ion and the theoretical fragment ion to which it was assigned was 40 parts/million (0.038 Da), and the standard error for all fragment ions of a modified peptide was 10 parts/million (0.010 Da). Trp-32 is a surface residue; see model in FIG. 10.
Figure 10:
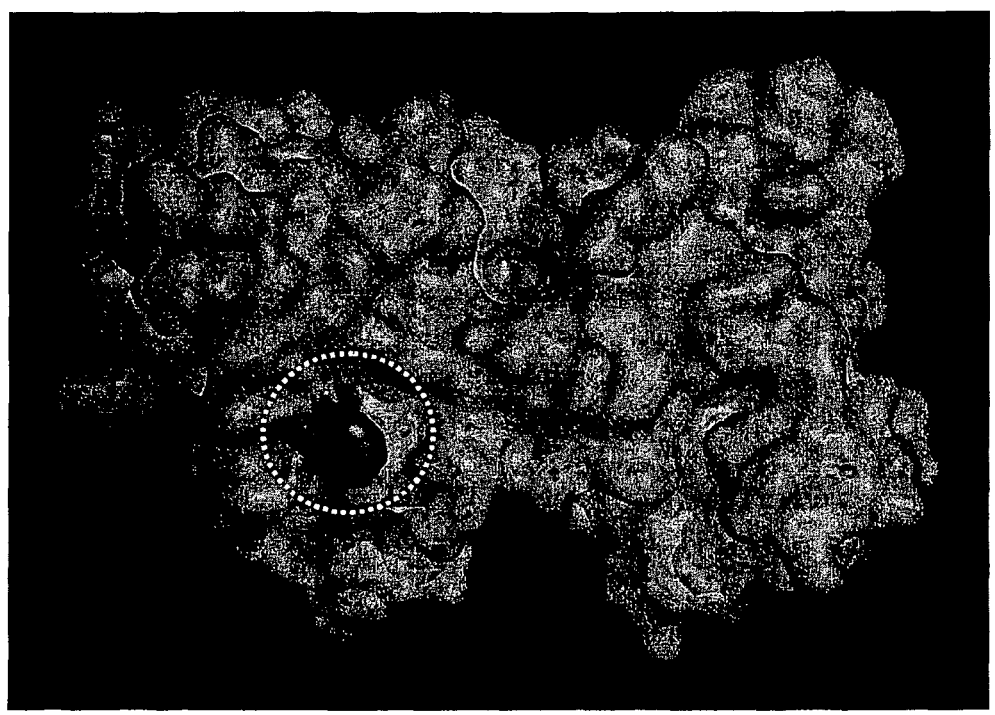
FIG. 10 depicts a crystal structure of SOD-1 with Trp-32 highlighted. Protein structure data bank file 1 SPD (Deng, H. X., Hentati, A., Tainer, J. A., Iqbal, Z., Cayabyab, A., Hung, W. Y., Getzoff, E. D., Hu, P., Herzfeldt, B., and Roos, R. P. (1993) Science 261, 1047-1051) was rendered with a transparent surface and with Trp-32 shown as a ball and stick model using PyMOL.

To identify sites of oxidative modification, SOD-1 was digested with endoproteinase GluC, creating peptides that are amenable to MS/MS analysis. Peptides were separated by reverse phase liquid chromatography (FIG. 9A), their masses were measured using MS, and peptides were isolated and subjected to CAD (FIG. 9, C and D). The peptide mass and fragment masses were used to "sequence" and identify peptides using the MASCOT search engine followed by manual validation, and the full amino acid sequence of SOD-1 was accounted for. Individual peptides of SOD-1 were surveyed for oxidative modification (FIG. 9B, inset), and potentially modified peptides were sequenced in subsequent LC-MS/MS experiments. Following this procedure, Trp-32 was determined to be modified by one and two oxygen atom(s) (FIG. 9, D and E). Post-translational modification of both intact protein and Trp-32 were present in preparations from both aerobic and anaerobic conditions, indicating that oxidative modification occurred in vivo, not as an artifact from exposure to air during purification or digestion (FIG. 10).

The survival and aggregation of SOD-1W32F/G93A is also described herein. In previous studies, recombinant SOD-1 was oxidized at Trp-32 and aggregated following exposure to peroxide or superoxide in vitro. Zhang, H., Joseph, J., Crow, J., and Kalyanaraman, B. (2004) Free Radic. Biol. Med. 37, 2018-2026; and Zhang, H., Andrekopoulos, C., Joseph, J., Chandran, K., Karoui, H., Crow, J. P., and Kalyanaraman, B. (2003) J. Biol. Chem. 278, 24078-24089. Rates of oxidation-induced aggregation of SOD-1wt were decreased by replacing Trp-32 with Phe. Zhang, H., Andrekopoulos, C., Joseph, J., Chandran, K., Karoui, H., Crow, J. P., and Kalyanaraman, B. (2003) J. Biol. Chem. 278, 24078-24089. This finding, combined with the identification, in this study, of oxidized Trp-32 in as-isolated SOD-1, provided the impetus to test whether Trp-32 plays a role in the toxicity or aggregation of mutant SOD-1 in living motor neurons. Trp-32 was replaced with Phe in SOD-1G93A and in the SOD-1wt control. The G93A mutant was chosen because it retains normal dismutase activity and has been relatively well characterized. Borchelt, D. R., Lee, M. K., Slunt, H. S., Guarnieri, M., Xu, Z. S., Wong, P. C., Brown, R. H., Jr., Price, D. L., Sisodia, S. S., and Cleveland, D. W. (1994) Proc. Natl. Acad. Sci. U.S.A. 91, 8292-8296. Plasmids encoding SOD-1wt, SOD-1 W32F, SOD-1G93A, and SOD-1W32F/G93A were expressed in the motor neurons of long term dissociated spinal cord-dorsal root ganglia cultures. Durham, H. D., Roy, J., Dong, L., and Figlewicz, D. A. (1997) J. Neuropathol. Exp. Neurol. 56, 523-530; and Roy, J., Minotti, S., Dong, L., Figlewicz, D. A., and Durham, H. D. (1998) J. Neurosci. 18, 9673-9684.

Figure 11:
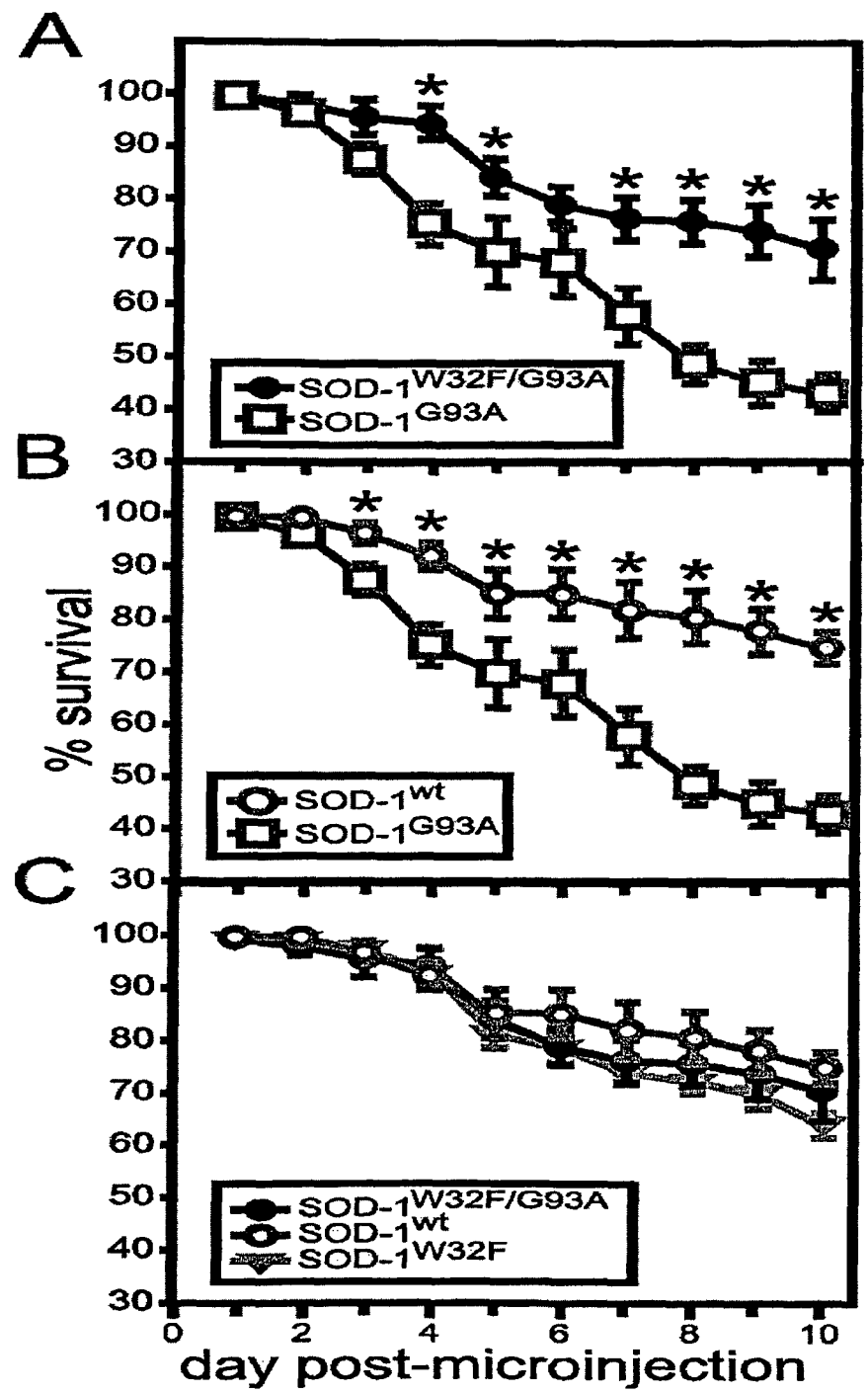
FIG. 11 depicts data showing that mutating Trp-32 to Phe ameliorates the toxicity of SOD-1$^{G93A}$ in cultured motor neurons. Motor neurons were microinjected with plasmid encoding SOD-1$^{G93A}$, SOD-1$^{wt}$, SOD-1$^{W32F/G93A}$, or SOD-1$^{W32F}$ along with the marker, 70-kDa dextran-fluorescein. Viable motor neurons were counted daily for 10 days. Shown are the data from a single experiment with six cultures from the same batch for each condition. Data were reproduced in another culture batch, and grouping of the data from all experiments did not alter the significance at any time point. Statistical comparisons were made groupwise using analysis of variance, and curves were plotted separately to highlight key comparisons. [A] SOD-1$^{W32F/G93A}$ significantly improved the viability of motor neurons in comparison to those expressing SOD-1$^{G93A}$. [B] The difference between the viability of motor neurons expressing SOD-1$^{G93A}$ or SOD-1" was significant at the same time points as the comparison in A. [C] The mutants SOD-1$^{W32F/G93A}$ and SOD-1$^{W32F}$ exhibit similar toxicity to SOD1$^{wt}$ (*, p<0.001, day 4; p<0.01, day 7; p<0.0001 at days 8-10 using analysis of variance and the Holm-Sidak method of pairwise group comparison). Bonferroni and Tukey tests confirmed significance at each time point.

As previously reported, motor neurons expressing SOD-$1^{G93A}$ died at a considerably faster rate over the 10 days of observation relative to motor neurons expressing SOD-$1^{wt}$ (FIG. 11B). Durham, H. D., Roy, J., Dong, L., and Figlewicz, D. A. (1997) J. Neuropathol. Exp. Neurol. 56, 523-53. The presence of the W32F mutation significantly reduced the death of motor neurons conferred by the G93A mutation from 6.8 to 3.6%/day (FIG. 11A). In fact, viability of motor neurons expressing SOD-1 with the double mutation (W32F and G93A) did not differ significantly from the controls; SOD-$1^{wt}$ (3.0%/day), SOD-$1^{W32F}$ (4.3%/day), and SOD-$1^{W32F/G93A}$ (3.6%/day) survived as a group (FIG. 11C).

Figure 12:
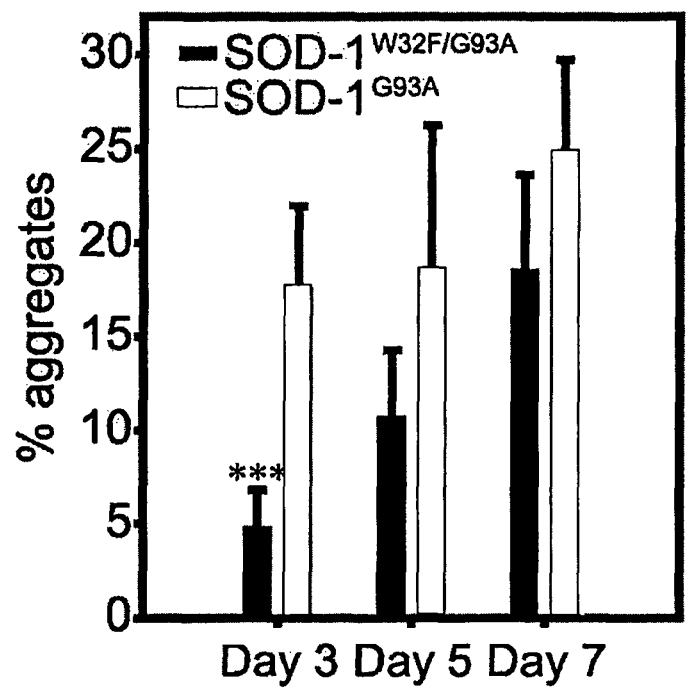
FIG. 12 depicts data showing that the mutation of Trp-32 to Phe delays aggregation of SOD1G93A into inclusions in cultured motor neurons. The table provides the percentage of motor neurons microinjected with plasmid encoding SOD-1G93A and SOD-1 W32F/G93A that contained SOD-1-positive cytoplasmic inclusions. The graphs shows that the W32F mutation significantly reduced the percentage of motor neurons with mutant SOD-1 inclusions at post-microinjection day 3. There was no observable difference in the size or distribution of the aggregates observed in a given SOD-1G93A or SOD-1 W32F/G93A inclusion-containing cell, although a significantly lower proportion of SOD-1 W32F/G93A-injected cells contained aggregates at day 3. Normal distribution of the data allowed for weighted t test comparison of data (p<0.005, day 3). No significant difference was observed at days 5 and 7.

SOD-$1^{wt}$ distributed diffusely throughout the cell (data not shown), whereas a proportion of motor neurons expressing SOD-$1^{G93A}$ contained SOD-1 immunoreactive inclusions. Not only did introduction of the W32F mutation into SOD-$1^{G93A}$ prolong the survival of motor neurons, it also delayed aggregation of the protein into inclusions (FIG. 12).

The results presented herein indicate that oxidation of Trp-32 occurs in vivo as a natural modification to SOD-1 and that the Trp-32 residue is an important mediator of the toxicity of an SOD-$1^{G93A}$ mutant associated with fALS. Exchanging Trp-32 with the less oxidation-prone Phe decreased the toxicity of SOD-$1^{G93A}$ to motor neurons, reducing both lethality and the formation of cytoplasmic, SOD-1-containing inclusions. This study does not rule out the possibility that a property of Trp-32 other than its propensity for oxidative modification promotes toxicity of mutant SOD-1. For instance, tryptophan is among the most critical residues in the formation of protein-protein and protein-ion interactions. Bogan, A. A., and Thorn, K. S. (1998) J. Mol. Biol. 280, 1-9; Dougherty, D. A. (1996) Science 271, 163-168; and Gallivan, J. P., and Dougherty, D. A. (1999) Proc. Natl. Acad. Sci. U.S.A. 96, 9459-9464. There are, however, a number of circumstantial arguments supporting the involvement of oxidative modification of Trp-32 in the promotion of G93A toxicity. (1) Trp-32 was found to be oxidized in vivo. (2) Trp is the most oxidizable of all of the amino acids, and Trp oxidation is associated with in vitro aggregation. Davies, K. J. (1987) J. Biol. Chem. 262, 9895-9901; and Davies, K. J., Delsignore, M. E., and Lin, S. W. (1987) J. Biol. Chem. 262, 9902-9907. (3) Mutating Trp to Phe also slows the rate of aggregation of recombinant SOD-$1^{wt}$ following oxidative modification in vitro. Zhang, H., Andrekopoulos, C., Joseph, J., Chandran, K., Karoui, H., Crow, J. P., and Kalyanaraman, B. (2003) J. Biol. Chem. 278, 24078-24089. (4) Oxidative modification of Trp results in the formation of free carbonyl moieties that go on to form advanced glycation end products; carbonyl-containing as well as anionic detergent- and dithiothreitol/β-mercaptoethanol-resistant high molecular weight species of mutant SOD-1 have been detected in cultured cells and in both tissues and filter-purified aggregates of transgenic mice expressing mutant SOD-1. Shinder, G. A., Lacourse, M. C., Minotti, S., and Durham, H. D. (2001) J. Biol. Chem. 276, 12791-12796; Johnston, J. A., Dalton, M. J., Gurney, M. E., and Kopito, R. R. (2000) Proc. Natl. Acad. Sci. U.S.A. 97, 12571-12576; Wang, J., Xu, G., and Borchelt, D. R. (2002) Neurobiol. Dis. 9, 139-148; and Shibata, N., Hirano, A., Hedley-Whyte, E. T., Dal Canto, M. C., Nagai, R., Uchida, K., Horiuchi, S., Kawaguchi, M., Yamamoto, T., and Kobayashi, M. (2002) Acta Neuropathol. (Berl.) 104, 171-178.

Direct measurement of the relationship between Trp-32 oxidation and protein conformation in vivo would require physical separation of oxidized and unmodified SOD-1, which would be difficult to achieve. Although there is controversy over the relationship between the aggregation of mutant SOD-1 and disease-related toxicity (reviewed in Kabashi, E., and Durham, H. D. (2006) Biochim. Biophys. Acta 1762, 1038-1050), only treatments that reduce the formation of cytoplasmic mutant SOD-1 inclusions also prolong survival in the primary motor neuron culture model provided herein. Roy, J., Minotti, S., Dong, L., Figlewicz, D. A., and Durham, H. D. (1998) J. Neurosci. 18, 9673-9684; Bruening, W., Roy, J., Giasson, B., Figlewicz, D. A., Mushynski, W. E., and Durham, H. D. (1999) J. Neurochem. 72, 693-699; Batulan, Z., Taylor, D. M., Aarons, R. J., Minotti, S., Doroudchi, M. M., Nalbantoglu, J., and Durham, H. D. (2006) Neurobiol. Dis. 24, 213-225; Batulan, Z., Shinder, G. A., Minotti, S., He, B. P., Doroudchi, M. M., Nalbantoglu, J., Strong, M. J., and Durham, H. D. (2003) J. Neurosci. 23, 5789-5798; and Batulan, Z., Nalbantoglu, J., and Durham, H. D. (2005) Cell Stress Chaperones 10, 185-196. This culture system has the distinct advantage of utilizing primary motor neurons, cells with particular vulnerability to mutant SOD-1 toxicity and ALS generally. Boillee, S., Yamanaka, K., Lobsiger, C. S., Copeland, N. G., Jenkins, N. A., Kassiotis, G., Kollias, G., and Cleveland, D. W. (2006) Science 312, 1389-1392; and Boillee, S., Vande Velde, C., and Cleveland, D. W. (2006) Neuron 52, 39-59.

In previous in vitro oxidation studies, the major modifications identified by MS or amino acid analysis were oxidation of active site H is residues. Zhang, H., Joseph, J., Crow, J., and Kalyanaraman, B. (2004) Free Radic. Biol. Med. 37, 2018-2026; Rakhit, R., Cunningham, P., Furtos-Matei, A., Dahan, S., Qi, X. F., Crow, J. P., Cashman, N. R., Kondejewski, L. H., and Chakrabartty, A. (2002) J. Biol. Chem. 277, 47551-47556; Zhang, H., Andrekopoulos, C., Joseph, J., Chandran, K., Karoui, H., Crow, J. P., and Kalyanaraman, B. (2003) J. Biol. Chem. 278, 24078-24089; and Kurahashi, T., Miyazaki, A., Suwan, S., and Isobe, M. (2001) J. Am. Chem. Soc. 123, 9268-9278. In all in vitro studies, activity and presumably copper were lost upon oxidation. In described herein, no more than 2% of SOD-1 isolated from erythrocytes was modified at His residues, and oxidatively modified SOD-1 retained its metals and presumably its activity. Forman, H. J., and Fridovich, I. (1973) J. Biol. Chem. 248, 2645-2649. In vitro oxidation is metal-catalyzed Fenton-type oxidation by hydroxyl radicals and may not mimic in vivo oxidation where SOD-1 is surrounded by diverse oxidants and antioxidants that change with both cell state and location. However, this does not rule out that oxidation of His residues occurs in vivo, considering that oxidatively modified SOD-1 is a target for proteasome degradation and that fALS mutations exhibit decreased stability in vivo through proteasome-mediated degradation. Davies, K. J. (1987) J. Biol. Chem. 262, 9895-9901; Borchelt, D. R., Lee, M. K., Slunt, H. S., Guarnieri, M., Xu, Z. S., Wong, P. C., Brown, R. H., Jr., Price, D. L., Sisodia, S. S., and Cleveland, D. W. (1994) Proc. Natl. Acad. Sci. U.S.A. 91, 8292-8296; and Hoffman, E. K., Wilcox, H. M., Scott, R. W., and Siman, R. (1996) J. Neurol. Sci. 139, 15-20. That 20-30% of human SOD-$1^{wt}$ from erythrocytes was oxidatively modified argues against all oxidative modifications acting as a trigger for degradation, given the long half-life of the wild-type protein. Borchelt, D. R., Lee, M. K., Slunt, H. S., Guarnieri, M., Xu, Z. S., Wong, P. C., Brown, R. H., Jr., Price, D. L., Sisodia, S. S., and Cleveland, D. W. (1994) Proc. Natl. Acad. Sci. U.S.A. 91, 8292-8296.

Oxidative modification of SOD-1 has been observed in Alzheimer, Parkinson, and fALS models. Such oxidative modification, however, should not be regarded as inherently toxic. Oxidative modification, thus far exclusive to cysteine, can increase protein stability, be cytoprotective, activate enzymes, or modulate subcellular localization (reviewed in Rhee, S. G. (2006) Science 312, 1882-1883; see also Claiborne, A., Mallett, T. C., Yeh, J. I., Luba, J., and Parsonage, D. (2001) Adv. Protein Chem. 58, 215-276). For instance, with the chaperone DJ-1, oxidative modification has been observed in the brains of Alzheimer and Parkinson patients. Choi, J., Sullards, M. C., Olzmann, J. A., Rees, H. D., Weintraub, S. T., Bostwick, D. E., Gearing, M., Levey, A. I., Chin, L. S., and Li, L. (2006) J. Biol. Chem. 281, 10816-10824. Cysteine oxidation of DJ-1, however, appears to create a cytoprotective protein that changes localization from the cytoplasm to the mitochondria, leaving open the possibility that those disease-related modifications are protective. Canet-Aviles, R. M., Wilson, M. A., Miller, D. W., Ahmad, R., McLendon, C., Bandyopadhyay, S., Baptista, M. J., Ringe, D., Petsko, G. A., and Cookson, M. R. (2004) Proc. Natl. Acad. Sci. U.S.A. 101, 9103-9108. Whether an analogous oxidation of SOD-1 drives fALS mutant SOD-1 accumulation in mitochondria warrants further study. Okado-Matsumoto, A., and Fridovich, I. (2001) Anal. Biochem. 298, 337-342; Pasinelli, P., Belford, M. E., Lennon, N., Bacskai, B. J., Hyman, B. T., Trotti, D., and Brown, R. H., Jr. (2004) Neuron 43, 19-30; Liu, J., Lillo, C., Jonsson, P. A., Vande Velde, C., Ward, C. M., Miller, T. M., Subramaniam, J. R., Rothstein, J. D., Marklund, S., Andersen, P. M., Brannstrom, T., Gredal, O., Wong, P. C., Williams, D. S., and Cleveland, D. W. (2004) Neuron 43, 5-17; Weisiger, R. A., and Fridovich, I. (1973) J. Biol. Chem. 248, 4793-4796; and Weisiger, R. A., and Fridovich, I. (1973) J. Biol. Chem. 248, 3582-3592. Clearly, post-translational modifications are not inherently toxic, and direct analysis of toxicity conferred by a given residue's modification is required. Taken together, the high oxidation propensity of Trp, the decrease in both cytopathological and peroxide-induced aggregation, and the in vivo oxidation of Trp-32 indicate that Trp-32 oxidative modification exacerbates the toxicity of the fALS SOD-1 mutation, SOD-1$^{G93A}$.

Therefore, because tryptophan oxidation leads to the formation of advanced glycation endproducts (AGEs), one aspect of the invention disclosed herein is a method of treating ALS, comprising administering to a patient in need thereof a therapeutically effective amount of an inhibitor of the formation of AGEs. In certain embodiments, the method uses an inhibitor of AGE formation that binds and/or detoxifies dicarbonyl intermediates. In certain embodiments, the method uses an inhibitor of AGE formation that disrupts AGE-based crosslinks.

In certain circumstances, AGEs are non-enzymatically formed by reducing glucose, lipids, and/or certain amino acids on proteins, lipids, and nucleic acids. For example, glucose and a free amino group form reversible intermediates of a Schiff base and an Amadori product (e.g., HbA1c) before a series of reactions that irreversibly generate an AGE. This process was first identified in 1912 and is known as the Maillard or "browning" reaction due to the associated yellow-brown color change. Alternate mechanisms of AGE formation include the "carbonyl stress" pathway, where oxidation of sugars and/or lipids create dicarbonyl intermediate compounds that use highly reactive carbonyl groups to bind amino acids and form AGEs. Non-glucose-dependent AGE pathways involve neutrophils, monocytes, and macrophages, which, upon inflammatory stimulation, produce myeloperoxidase and NADPH oxidase enzymes that induce AGE formation by oxidizing amino acids. Once bound by AGEs, receptors for AGE (RAGE) associated with reactive oxygen species generation promote more AGEs via the NADPH oxidase pathway. Monocytes, macrophages, and dendritic cells also secrete the nuclear protein amphoterin (also termed high-mobility group box 1 [HMGB1]), and HMGB1 can bind and activate RAGE and thus induce further inflammation. Another mechanism of AGE formation is the aldose reductase-mediated polyol pathway. Glucose entering the polyol pathway may directly form AGEs via 3-deoxyglucosone AGE intermediates, but this reaction also causes depletion of NADPH and glutathione, and the resultant oxidative stress indirectly increases formation of AGEs.

Given their varied mechanisms of formation, it is not surprising that AGEs are a heterogeneous group of compounds. Some AGEs are capable of intra- and intermolecular crosslinking, but not all share those properties. Once formed, certain cross-linking AGEs form stable cross-link structures with other proteins in the body, including structural proteins (e.g., collagen), intracellular proteins, membrane phospholipids, DNA, and lipoproteins (e.g., LDL cholesterol), and also bind to AGE receptors.

Aminoguanidine, which interferes with AGE production, has been shown to improve nephropathy, retinopathy, and vessel elasticity when administered to diabetic rats. Rahbar S, Figarola J L. Novel inhibitors of advanced glycation endproducts. Arch Biochem Biophys 2003; 419:63-79. While increased incidence of glomerulonephritis has been seen with higher-dose amino-guanidine in human phase III trials, the lower dose was equally effective at ameliorating proteinuria (P<0.001) and preventing retinopathy progression (P=0.03) and was free of serious side effects. However, aminoguanidine's binding of pyridoxal may lead to vitamin B6 deficiency and associated neurotoxicity. Aminoguanidine's toxicity has halted further studies, but its positive impact on proteinuria and vascular elasticity provide proof of concept and have encouraged continued development of other AGE-targeted therapies.

Pyridoxamine is one of three vitamin B6 natural forms. It retarded AGE formation and inhibited diabetic nephropathy equally to aminoguanidine and lowered cholesterol levels more than aminoguanidine while inducing mild weight loss in both nondiabetic and diabetic rats.

The peroxisome proliferator-activated receptor agonist OPB 9195 ([(±)-2-Isopropylidenehydrazono-4-oxo-thiazolidin-5-ylacetanilide) has inhibitory actions on glycoxidation and lipoxidation reactions, thereby decreasing formation of AGEs and dicarbonyl intermediates. This compound is also hypothesized to scavenge dicarbonyl intermediates. In animal models, OPB 9195 reduced progression of nephropathy, lowered blood pressure, reduced oxidative stress, and impaired carotid artery intimal proliferation following balloon damage to the endothelium.

ALT-946 (N-(2-acetamidoethyl)hydrazinecarboximidamide hydrochloride) therapy for 12 weeks has been shown to reduce renal AGEs by histologic analysis and to decrease albuminuria by 250% compared with aminoguanidine therapy in diabetic hypertensive rats. An additional study showed that ALT-946 therapy in a rat model reduced albuminuria both when used at the onset of diabetes and when initiated after 16 weeks of diabetes.

A promising line of AGE therapy investigates agents that disrupt the cross-links that bind AGEs to human tissue. ALT-711 (alagebrium chloride) is capable of cleaving AGE crosslinks, thus allowing endogenous AGE removal from vessel walls. A randomized, placebo-controlled trial in 93 hypertensive subjects age greater than 50 years showed significant reduction in pulse pressure and arterial stiffness in ALT-711-treated subjects compared with placebo. A 16-week open-label trial of ALT-711 in 23 humans with systolic hypertension and moderately severe diastolic heart failure (22% with diabetes) decreased left ventricular mass, improved left ventricular filling, and improved patient ratings of quality of life. In diabetic rats, ALT-711 has been shown to decrease levels of AGEs, RAGE expression, diabetic nephropathy, myocardial stiffness, and has attenuated atherosclerosis and decreased cholesterol and systolic blood pressure in diabetic hyperlipidemic mice. Another AGE cross-link breaker is N-phenacylthiazolium bromide. In diabetic rat models, this agent has been shown to decrease AGEs but has not decreased nephropathy as measured by proteinuria.

Metformin and pioglitazone have been shown in vitro to prevent AGE formation. ACE inhibitors (temocaprilat) and ARBs (olmesartan, candesartan, irbesartan, losartan, telmisartan, and valsartan) were effective in vitro at decreasing AGE formation. Studies in humans have shown decreased vascular inflammation with irbesartan and decreased RAGE levels with perindopril. Perindopril has also inhibited atherosclerosis in mice. However, after 12 weeks of ramipril therapy in mice, there was no significant impact on RAGE levels or expression of the proinflammatory transcription factor, NF-kB. In humans, the exact mechanism by which ACE inhibitors and ARBs effect AGEs is uncertain. Studies in humans with antioxidants have shown mixed benefit. These studies are summarized in FIG. 1.

One aspect of the invention relates to a method of treating or preventing a neurodegenerative disease, comprising the step of administering to a patient in need thereof a therapeutically effective amount of an inhibitor of the formation of advanced glycation end products.

In certain embodiments, the present invention relates to any one of the aforementioned methods and attendant definitions, wherein the inhibitor of the formation of advanced glycation end products is selected from the group consisting of aminoguanidine, carnosine, metformin, and derivatives thereof.

In certain embodiments, the present invention relates to any one of the aforementioned methods and attendant definitions, wherein said inhibitor of the formation of advanced glycation end products binds and/or detoxifies dicarbonyl intermediates.

In certain embodiments, the present invention relates to any one of the aforementioned methods and attendant definitions, wherein said inhibitor of the formation of advanced glycation end products disrupts advanced glycation end product-based crosslinks.

One aspect of the invention relates to a method of treating or preventing a neurodegenerative disease, comprising the step of administering to a patient in need thereof a therapeutically effective amount of a compound selected from the group consisting of aminoguanidine, pyridoxamine, (±)-2-isopropylidenehydrazono-4-oxo-thiazolidin-5-ylacetanilide, N-(2-acetamidoethyl)hydrazinecarboximidamide hydrochloride, alagebrium chloride, metformin carnosine, pioglitazone, irbesartan, perindopril, temocaprilat, olmesartan, candesartan, irbesartan, losartan, telmisartan, valsartan, benfotiamine, epalrestat, zopolrestat, and derivatives thereof.

In certain embodiments, the present invention relates to any one of the aforementioned methods and attendant definitions, wherein the neurodegenerative disease is Alzheimer, Parkinson, or Amyotrophic lateral sclerosis.

In certain embodiments, the present invention relates to any one of the aforementioned methods and attendant definitions, wherein the neurodegenerative disease is Amyotrophic lateral sclerosis.

Proteasome Activity-Based Screening Assay

One aspect of the invention relates to a proteasome activity-based screening assay. In certain embodiments, the proteasome activity-based screening assay may be used for discovering potential ALS therapeutics. In certain embodiments, the assay is based upon the propensity of mutants that cause fALS to be catabolized by the proteasome and inhibit proteasome activity. Hoffman E K, Wilcox H M, Scott R W, Siman R. Proteasome inhibition enhances the stability of mouse Cu/Zn superoxide dismutase with mutations linked to familial amyotrophic lateral sclerosis. J. Neurol. Sci. 1996; 139: 15-20; Puttaparthi K, Wojcik C, Rajendran B, DeMartino G N, Elliott J L. Aggregate formation in the spinal cord of mutant SOD1 transgenic mice is reversible and mediated by proteasomes. J. Neurochem. 2003; 87:851-860; and Urushitani M, Kurisu J, Tsukita K, Takahashi R. Proteasomal inhibition by misfolded mutant superoxide dismutase 1 induces selective motor neuron death in familial amyotrophic lateral sclerosis. J. Neurochem. 2002; 83:1030-1042. The underlying assumption of this assay is that proteasome activity is a surrogate marker for ALS toxicity. This view is well supported in the literature as proteasome inhibition is among the earliest observed phenotypes in fALS model mice and loss of proteasome activity is cytotoxic, particularly to neurons. Urushitani M, Kurisu J, Tsukita K, Takahashi R. Proteasomal inhibition by misfolded mutant superoxide dismutase 1 induces selective motor neuron death in familial amyotrophic lateral sclerosis. J. Neurochem. 2002; 83:1030-1042; Durham H D, Kabashi, E., Taylor, D. M., Agar, J. N. Motor Neuron Disease: Springer US, 2007; Kabashi E, Durham H D. Failure of protein quality control in amyotrophic lateral sclerosis. Biochim Biophys Acta 2006; 1762:1038-1050; Kabashi E, Agar J N, Taylor D M, Minotti S, Durham H D. Focal dysfunction of the proteasome: a pathogenic factor in a mouse model of amyotrophic lateral sclerosis. J. Neurochem. 2004; 89:1325-1335; Tsuji S, Kikuchi S, Shinpo K, et al. Proteasome inhibition induces selective motor neuron death in organotypic slice cultures. J Neurosci Res 2005; 82:443-451; Ding Q, Dimayuga E, Martin S, et al. Characterization of chronic low-level proteasome inhibition on neural homeostasis. J. Neurochem. 2003; 86:489-497; Ding Q, Keller J N. Proteasome inhibition in oxidative stress neurotoxicity: implications for heat shock proteins. J. Neurochem. 2001; 77:1010-1017; Ding Q, Keller J N. Proteasomes and proteasome inhibition in the central nervous system. Free Radic. Biol. Med. 2001; 31:574-584; Mytilineou C, McNaught K S, Shashidharan P, et al. Inhibition of proteasome activity sensitizes dopamine neurons to protein alterations and oxidative stress. J Neural Transm 2004; 111:1237-1251; and McNaught K S, Mytilineou C, Jnobaptiste R, et al. Impairment of the ubiquitin-proteasome system causes dopaminergic cell death and inclusion body formation in ventral mesencephalic cultures. J Neurochem 2002; 81:301-306. Therefore, compounds that relieve proteasome inhibition are expected to ameliorate ALS symptoms.

Therefore, one aspect of the invention relates to monitoring proteasome activity to screen for potential ALS therapeutic compounds. FIG. 2 illustrates the results of using SOD-1 expressing cells (eG93A SOD-1 expressing clones; wild-type SOD-1 expressing clones; and W32F G93A SOD-1 expressing clones) for said purpose. In certain embodiments, the assay involves administration of different concentrations of a given compound to G93A- and wild-type SOD-1 cell lines, and assaying proteasome activity. Successful compounds, in analogy to W32F/G93A double mutant (FIG. 2), will relieve G93A SOD-1 associated proteasome inhibition. Due to the near complete inhibition of proteasome activity in G93A cell lines, this is expected to be a sensitive assay. With successful hits, SOD-1 protein can be immunopurified from cell cultures to determine if there is any direct chemical bonding to SOD-1.

One aspect of the invention relates to a nucleic acid molecule comprising a nucleic acid which is at least 90 percent identical to SEQ ID Nos. 1, 4, 6, or 8.

One aspect of the invention relates to a nucleic acid molecule consisting essentially of a nucleic acid which is at least 90 percent identical to SEQ ID Nos. 1, 4, 6, or 8.

One aspect of the invention relates to a nucleic acid molecule consisting of a nucleic acid which is at least 90 percent identical to SEQ ID Nos. 1, 4, 6, or 8.

In certain embodiments, the present invention relates to any one of the aforementioned nucleic acids and attendant definitions, wherein the nucleic acid molecule is at least 90 percent identical to SEQ ID NO: 1. In certain embodiments, the present invention relates to any one of the aforementioned nucleic acids and attendant definitions, wherein the nucleic acid molecule is at least 95 percent identical to SEQ ID NO: 1. In certain embodiments, the present invention relates to any one of the aforementioned nucleic acids and attendant definitions, wherein the nucleic acid molecule is SEQ ID NO: 1.

In certain embodiments, the present invention relates to any one of the aforementioned nucleic acids and attendant definitions, wherein the nucleic acid molecule is at least 90 percent identical to SEQ ID NO: 4. In certain embodiments, the present invention relates to any one of the aforementioned methods and attendant definitions, wherein the nucleic acid molecule is at least 95 percent identical to SEQ ID NO: 4. In certain embodiments, the present invention relates to any one of the aforementioned nucleic acids and attendant definitions, wherein the nucleic acid molecule is SEQ ID NO: 4.

In certain embodiments, the present invention relates to any one of the aforementioned nucleic acids and attendant definitions, wherein the nucleic acid molecule is at least 90 percent identical to SEQ ID NO: 6. In certain embodiments, the present invention relates to any one of the aforementioned nucleic acids and attendant definitions, wherein the nucleic acid molecule is at least 95 percent identical to SEQ ID NO: 6. In certain embodiments, the present invention relates to any one of the aforementioned nucleic acids and attendant definitions, wherein the nucleic acid molecule is SEQ ID NO: 6.

In certain embodiments, the present invention relates to any one of the aforementioned nucleic acids and attendant definitions, wherein the nucleic acid molecule is at least 90 percent identical to SEQ ID NO: 8. In certain embodiments, the present invention relates to any one of the aforementioned nucleic acids and attendant definitions, wherein the nucleic acid molecule is at least 95 percent identical to SEQ ID NO: 8. In certain embodiments, the present invention relates to any one of the aforementioned nucleic acids and attendant definitions, wherein the nucleic acid molecule is SEQ ID NO: 8.

One aspect of the invention relates to an amino acid molecule comprising an amino acid which is at least 90 percent identical to SEQ ID Nos. 2, 5, 7, or 9.

One aspect of the invention relates to an amino acid molecule consisting essentially of an amino acid which is at least 90 percent identical to SEQ ID Nos. 2, 5, 7, or 9.

One aspect of the invention relates to an amino acid molecule consisting of an amino acid which is at least 90 percent identical to SEQ ID Nos. 2, 5, 7, or 9.

In certain embodiments, the present invention relates to any one of the aforementioned amino acids and attendant definitions, wherein the amino acid molecule is at least 90 percent identical to SEQ ID NO: 2. In certain embodiments, the present invention relates to any one of the aforementioned amino acids and attendant definitions, wherein the amino acid molecule is at least 95 percent identical to SEQ ID NO: 2. In certain embodiments, the present invention relates to any one of the aforementioned amino acids and attendant definitions, wherein the amino acid molecule is SEQ ID NO: 2.

In certain embodiments, the present invention relates to any one of the aforementioned amino acids and attendant definitions, wherein the amino acid molecule is at least 90 percent identical to SEQ ID NO: 5. In certain embodiments, the present invention relates to any one of the aforementioned amino acids and attendant definitions, wherein the amino acid molecule is at least 95 percent identical to SEQ ID NO: 5. In certain embodiments, the present invention relates to any one of the aforementioned amino acids and attendant definitions, wherein the amino acid molecule is SEQ ID NO: 5.

In certain embodiments, the present invention relates to any one of the aforementioned amino acids and attendant definitions, wherein the amino acid molecule is at least 90 percent identical to SEQ ID NO: 7. In certain embodiments, the present invention relates to any one of the aforementioned amino acids and attendant definitions, wherein the amino acid molecule is at least 95 percent identical to SEQ ID NO: 7. In certain embodiments, the present invention relates to any one of the aforementioned amino acids and attendant definitions, wherein the amino acid molecule is SEQ ID NO: 7.

In certain embodiments, the present invention relates to any one of the aforementioned amino acids and attendant definitions, wherein the amino acid molecule is at least 90 percent identical to SEQ ID NO: 9. In certain embodiments, the present invention relates to any one of the aforementioned amino acids and attendant definitions, wherein the amino acid molecule is at least 95 percent identical to SEQ ID NO: 9. In certain embodiments, the present invention relates to any one of the aforementioned amino acids and attendant definitions, wherein the amino acid molecule is SEQ ID NO: 9.

One aspect of the invention relates to a cell which comprises a nucleic acid which comprises a nucleic acid which is at least 90% identical to SEQ ID NO: 1, 4, 6, or 8.

One aspect of the invention relates to a cell which comprises a nucleic acid which consists essentially of a nucleic acid which is at least 90% identical to SEQ ID NO: 1, 4, 6, or 8.

One aspect of the invention relates to a cell which comprises a nucleic acid which consists of a nucleic acid which is at least 90% identical to SEQ ID NO: 1, 4, 6, or 8.

In certain embodiments, the present invention relates to any one of the aforementioned cells and attendant definitions, wherein the nucleic acid molecule is at least 90 percent identical to SEQ ID NO: 1. In certain embodiments, the present invention relates to any one of the aforementioned cells and attendant definitions, wherein the nucleic acid molecule is at least 95 percent identical to SEQ ID NO: 1. In certain embodiments, the present invention relates to any one of the aforementioned cells and attendant definitions, wherein the nucleic acid molecule is SEQ ID NO: 1.

In certain embodiments, the present invention relates to any one of the aforementioned cells and attendant definitions, wherein the nucleic acid molecule is at least 90 percent identical to SEQ ID NO: 4. In certain embodiments, the present invention relates to any one of the aforementioned methods and attendant definitions, wherein the nucleic acid molecule is at least 95 percent identical to SEQ ID NO: 4. In certain embodiments, the present invention relates to any one of the aforementioned cells and attendant definitions, wherein the nucleic acid molecule is SEQ ID NO: 4.

In certain embodiments, the present invention relates to any one of the aforementioned cells and attendant definitions, wherein the nucleic acid molecule is at least 90 percent identical to SEQ ID NO: 6. In certain embodiments, the present invention relates to any one of the aforementioned cells and attendant definitions, wherein the nucleic acid molecule is at least 95 percent identical to SEQ ID NO: 6. In certain embodiments, the present invention relates to any one of the aforementioned cells and attendant definitions, wherein the nucleic acid molecule is SEQ ID NO: 6.

In certain embodiments, the present invention relates to any one of the aforementioned cells and attendant definitions, wherein the nucleic acid molecule is at least 90 percent identical to SEQ ID NO: 8. In certain embodiments, the present invention relates to any one of the aforementioned cells and attendant definitions, wherein the nucleic acid molecule is at least 95 percent identical to SEQ ID NO: 8. In certain embodiments, the present invention relates to any one of the aforementioned cells and attendant definitions, wherein the nucleic acid molecule is SEQ ID NO: 8.

One aspect of the invention relates to a cell which comprises an amino acid which comprises an amino acid which is at least 90% identical to SEQ ID NO: 2, 5, 7, or 9.

One aspect of the invention relates to a cell which comprises an amino acid which consists essentially of an amino acid which is at least 90% identical to SEQ ID NO: 2, 5, 7, or 9.

One aspect of the invention relates to a cell which comprises an amino acid which consists of an amino acid which is at least 90% identical to SEQ ID NO: 2, 5, 7, or 9.

In certain embodiments, the present invention relates to any one of the aforementioned cells and attendant definitions, wherein the amino acid molecule is at least 90 percent identical to SEQ ID NO: 2. In certain embodiments, the present invention relates to any one of the aforementioned cells and attendant definitions, wherein the amino acid molecule is at least 95 percent identical to SEQ ID NO: 2. In certain embodiments, the present invention relates to any one of the aforementioned cells and attendant definitions, wherein the amino acid molecule is SEQ ID NO: 2.

In certain embodiments, the present invention relates to any one of the aforementioned cells and attendant definitions, wherein the amino acid molecule is at least 90 percent identical to SEQ ID NO: 5. In certain embodiments, the present invention relates to any one of the aforementioned cells and attendant definitions, wherein the amino acid molecule is at least 95 percent identical to SEQ ID NO: 5. In certain embodiments, the present invention relates to any one of the aforementioned cells and attendant definitions, wherein the amino acid molecule is SEQ ID NO: 5.

In certain embodiments, the present invention relates to any one of the aforementioned cells and attendant definitions, wherein the amino acid molecule is at least 90 percent identical to SEQ ID NO: 7. In certain embodiments, the present invention relates to any one of the aforementioned cells and attendant definitions, wherein the amino acid molecule is at least 95 percent identical to SEQ ID NO: 7. In certain embodiments, the present invention relates to any one of the aforementioned cells and attendant definitions, wherein the amino acid molecule is SEQ ID NO: 7.

In certain embodiments, the present invention relates to any one of the aforementioned cells and attendant definitions, wherein the amino acid molecule is at least 90 percent identical to SEQ ID NO: 9. In certain embodiments, the present invention relates to any one of the aforementioned cells and attendant definitions, wherein the amino acid molecule is at least 95 percent identical to SEQ ID NO: 9. In certain embodiments, the present invention relates to any one of the aforementioned cells and attendant definitions, wherein the amino acid molecule is SEQ ID NO: 9.

In certain embodiments, the present invention relates to any one of the aforementioned cells and attendant definitions, wherein the cell is stably transfected.

In certain embodiments, the present invention relates to any one of the aforementioned cells and attendant definitions, wherein the cell is monoclonal.

In certain embodiments, the present invention relates to any one of the aforementioned cells and attendant definitions, wherein the cell is a mammalian cell.

In certain embodiments, the present invention relates to any one of the aforementioned cells and attendant definitions, wherein the cell is a yeast cell.

In certain embodiments, the present invention relates to any one of the aforementioned cells and attendant definitions, wherein the cell is a bacterial cell.

In certain embodiments, the present invention relates to any one of the aforementioned cells and attendant definitions, wherein the cell is a NIH/3T3 cell.

One aspect of the invention relates to a method of screening a compound comprising the steps of: contacting a cell containing SOD-1$^{G93A}$ with the compound; and measuring the activity of the proteasome of the cell containing SOD-1$^{G93A}$.

One aspect of the invention relates to a method for identifying a compound that relieves proteasome inhibition caused by SOD-1$^{G93A}$ comprising the steps of:

contacting a genetically engineered host cell that contains a sequence encoding SOD-1$^{G93A}$ operatively associated with a regulatory sequence that controls gene expression, so that a SOD-1$^{G93A}$ gene product is stably expressed by the host cell (i.e., a cell containing SOD-1$^{G93A}$), with the a pre-determined amount of the compound;

measuring the activity of the proteasome in the host cell; and comparing the activity of the proteasome of the cells exposed to the compound to the proteasome activity of control cells that were not exposed to the compound.

In certain embodiments, the present invention relates to any one of the aforementioned methods and attendant definitions, further comprising the step of isolating the SOD-1$^{G93A}$ from the cell containing SOD-1$^{G93A}$.

In certain embodiments, the present invention relates to any one of the aforementioned methods and attendant definitions, further comprising the step of isolating the SOD-1$^{G93A}$ from the cell containing SOD-1$^{G93A}$; and determining if the compound is covalently bound to the SOD-1$^{G93A}$.

In certain embodiments, the present invention relates to any one of the aforementioned methods and attendant definitions, wherein a fluorogenic peptide is used to assay the proteasome activity of the cell containing SOD-1$^{G93A}$. The fluorogenic peptides of the invention preferably have a peptide sequence that includes at least one peptide bond cleavable by an enzyme, preferably a protease. Cleaving the peptide bond preferably releases the fluorogenic moiety from the peptide sequence, thereby producing a fluorescent moiety and a peptide moiety. The peptide bond which undergoes enzymatic cleavage can be located at any site within the peptide sequence. In certain embodiments, the peptide bond which undergoes enzymatic cleavage is located at a peptide bond formed between an amine of the fluorogenic moiety and a carboxylic acid moiety of the peptide carboxy terminus.

The term "fluorogenic moiety" is art-recognized and refers to a molecule or moiety, generally a polyaromatic hydrocarbon or heterocycle, that has the ability to fluoresce. The ability to fluoresce, or "fluorescence", of a fluorophore is generally understood to result from a three-stage process: (i) excitation, in which a photon is absorbed by the fluorophore, creating an excited electronic state in which the fluorophore has greater energy relative to the normal electronic state of the fluorophore; (ii) excited state lifetime, during which the fluorophore remains in the excited electronic state but also during which the energy of the state is partially dissipated; and (iii) emission, in which a photon of lower energy is emitted. Thus, a fluorophore absorbs a different wavelength of light (the "excitation wavelength") than it emits (the "emission wavelength").

In certain embodiments, the present invention relates to any one of the aforementioned methods and attendant definitions, wherein the cell containing SOD-1$^{G93A}$ is stably transfected.

In certain embodiments, the present invention relates to any one of the aforementioned methods and attendant definitions, wherein the cell containing SOD-1$^{G93A}$ is monoclonal.

In certain embodiments, the present invention relates to any one of the aforementioned methods and attendant definitions, wherein the cell containing SOD-1$^{G93A}$ is a mammalian cell.

In certain embodiments, the present invention relates to any one of the aforementioned cells and attendant definitions, wherein the cell containing SOD-1$^{G93A}$ is a yeast cell.

In certain embodiments, the present invention relates to any one of the aforementioned cells and attendant definitions, wherein the cell containing SOD-1$^{G93A}$ is a bacterial cell.

In certain embodiments, the present invention relates to any one of the aforementioned methods and attendant definitions, wherein the cell containing SOD-1$^{G93A}$ is a NIH/3T3 cell.

In certain embodiments, the present invention relates to any one of the aforementioned methods and attendant definitions, wherein the cell containing SOD-1$^{G93A}$ comprises a nucleic acid which is at least 90 percent identical to SEQ ID NO: 4. In certain embodiments, the present invention relates to any one of the aforementioned methods and attendant definitions, wherein the cell containing SOD-1$^{G93A}$ comprises a nucleic acid which is at least 95 percent identical to SEQ ID NO: 4. In certain embodiments, the present invention relates to any one of the aforementioned methods and attendant definitions, wherein the cell containing SOD-1$^{G93A}$ comprises a nucleic acid which is SEQ ID NO: 4.

In certain embodiments, the present invention relates to any one of the aforementioned methods and attendant definitions, further comprising the steps of contacting a cell containing SOD-1$^{wt}$ with the compound; and assaying the proteasome activity of the cell containing SOD-1$^{wt}$.

In certain embodiments, the present invention relates to any one of the aforementioned methods and attendant definitions, wherein a fluorogenic peptide is used to assay the proteasome activity of the cell containing SOD-1$^{wt}$.

In certain embodiments, the present invention relates to any one of the aforementioned methods and attendant definitions, further comprising the step of isolating the SOD-1$^{wt}$ from the cell containing SOD-1$^{wt}$.

In certain embodiments, the present invention relates to any one of the aforementioned methods and attendant definitions, further comprising the step of isolating the SOD-1$^{wt}$ from the cell containing SOD-1$^{wt}$; and determining if the compound is covalently bound to the SOD-1$^{wt}$.

In certain embodiments, the present invention relates to any one of the aforementioned methods and attendant definitions, wherein the cell containing SOD-1$^{wt}$ is stably transfected.

In certain embodiments, the present invention relates to any one of the aforementioned methods and attendant definitions, wherein the cell containing SOD-1$^{wt}$ is monoclonal.

In certain embodiments, the present invention relates to any one of the aforementioned methods and attendant definitions, wherein the cell containing SOD-1$^{wt}$ is a mammalian cell.

In certain embodiments, the present invention relates to any one of the aforementioned cells and attendant definitions, wherein the cell containing SOD-1$^{wt}$ is a yeast cell.

In certain embodiments, the present invention relates to any one of the aforementioned cells and attendant definitions, wherein the cell containing SOD-1$^{wt}$ is a bacterial cell.

In certain embodiments, the present invention relates to any one of the aforementioned methods and attendant definitions, wherein the cell containing SOD-1$^{wt}$ is a NIH/3T3 cell.

In certain embodiments, the present invention relates to any one of the aforementioned methods and attendant definitions, wherein the cell containing SOD-1$^{wt}$ comprises a nucleic acid which is at least 90 percent identical to SEQ ID NO: 1. In certain embodiments, the present invention relates to any one of the aforementioned methods and attendant definitions, wherein the cell containing SOD-1$^{wt}$ comprises a nucleic acid which is at least 95 percent identical to SEQ ID NO: 1. In certain embodiments, the present invention relates to any one of the aforementioned methods and attendant definitions, wherein the cell containing SOD-1$^{wt}$ comprises a nucleic acid which is SEQ ID NO: 1.

In certain embodiments, the present invention relates to any one of the aforementioned methods and attendant definitions, wherein the proteasome activity of the cell containing SOD-1$^{G93A}$ is increased by at least about 10% relative to the proteasome activity of the cell containing SOD-1$^{G93A}$ in the absence of the compound or relative to the proteasome activity of a cell containing SOD-1$^{wt}$ which has been contacted by the same compound.

In certain embodiments, the present invention relates to any one of the aforementioned methods and attendant definitions, wherein the proteasome activity of the cell containing SOD-1$^{G93A}$ is increased by at least about 25% relative to the proteasome activity of the cell containing SOD-1$^{G93A}$ in the absence of the compound or relative to the proteasome activity of a cell containing SOD-1$^{wt}$ which has been contacted by the same compound.

In certain embodiments, the present invention relates to any one of the aforementioned methods and attendant definitions, wherein the proteasome activity of the cell containing SOD-1$^{G93A}$ is increased by at least about 50% relative to the proteasome activity of the cell containing SOD-1$^{G93A}$ in the absence of the compound or relative to the proteasome activity of a cell containing SOD-1$^{wt}$ which has been contacted by the same compound.

In certain embodiments, the present invention relates to any one of the aforementioned methods and attendant definitions, wherein the proteasome activity of the cell containing SOD-1$^{G93A}$ is increased by at least about 75% relative to the proteasome activity of the cell containing SOD-1$^{G93A}$ in the absence of the compound or relative to the proteasome activity of a cell containing SOD-1$^{wt}$ which has been contacted by the same compound.

In certain embodiments, the present invention relates to any one of the aforementioned methods and attendant definitions, wherein the proteasome activity of the cell containing SOD-1$^{G93A}$ is increased by at least about 90% relative to the proteasome activity of the cell containing SOD-1$^{G93A}$ in the absence of the compound or relative to the proteasome activity of a cell containing SOD-1$^{wt}$ which has been contacted by the same compound.

In certain embodiments, the present invention relates to any one of the aforementioned methods and attendant definitions, further comprising the steps of contacting a cell containing SOD-1$^{W32F}$ with the compound; isolating the SOD-1$^{W32F}$ from the cell containing SOD-1$^{W32F}$; and determining if the compound is covalently bound to the SOD-1$^{W32F}$.

In certain embodiments, the present invention relates to any one of the aforementioned methods and attendant definitions, wherein the cell containing SOD-1$^{W32F}$ is stably transfected.

In certain embodiments, the present invention relates to any one of the aforementioned methods and attendant definitions, wherein the cell containing SOD-1$^{W32F}$ is monoclonal.

In certain embodiments, the present invention relates to any one of the aforementioned methods and attendant definitions, wherein the cell containing SOD-1$^{W32F}$ is a mammalian cell.

In certain embodiments, the present invention relates to any one of the aforementioned cells and attendant definitions, wherein the cell containing SOD-1$^{W32F}$ is a yeast cell.

In certain embodiments, the present invention relates to any one of the aforementioned cells and attendant definitions, wherein the cell containing SOD-1$^{W32F}$ is a bacterial cell.

In certain embodiments, the present invention relates to any one of the aforementioned methods and attendant definitions, wherein the cell containing SOD-1$^{W32F}$ is a NIH/3T3 cell.

In certain embodiments, the present invention relates to any one of the aforementioned methods and attendant definitions, wherein the cell containing SOD-1$^{W32F}$ comprises a nucleic acid which is at least 90 percent identical to SEQ ID NO: 8. In certain embodiments, the present invention relates to any one of the aforementioned methods and attendant definitions, wherein the cell containing SOD-1$^{W32F}$ comprises a nucleic acid which is at least 95 percent identical to SEQ ID NO: 8. In certain embodiments, the present invention relates to any one of the aforementioned methods and attendant definitions, wherein the cell containing SOD-1$^{W32F}$ comprises a nucleic acid which is SEQ ID NO: 8.

Binders of SOD-1 Trp32

One aspect of the invention relates to molecules which bind at or adjacent to Trp32; this includes molecules that bind in a site adjacent to Trp32 whether or not it is oxidized.

Preliminary results can not rule out the possibility that a property of Trp32 other than its propensity for oxidative modification promotes toxicity of mutant SOD-1. Indeed, tryptophan is among the most critical residues in the formation of protein-protein and protein-ion interactions. Therefore, to address the hypothesis that Trp32 mediated molecular interactions are a target for therapy, it is proposed herein to use of structure-guided drug discovery and development to find molecules that bind Trp32, thereby inhibiting other molecular interactions. Experience suggests that, properly applied, in silico screening can greatly increase the hit rate of actual screening. An experimental high throughput screen usually has hit rates of 0.01% or less. Thus a set of 200,000 or more compounds may have to be screened to find 20 hits in a good case. In silico screening can produce a list of 100 compounds from which it is not unusual to find 20-30 that actually bind to the target protein with reasonable affinity, a hit rate of about 25. These molecules need not be especially strong binders to efficacious, as their mechanism of action will resemble that of a pharmacological chaperone, which can be active at micromolar $K_d$.

One approach proposed herein is in some ways is similar to S. Ray and P. Lansbury study that identified SOD-1 subunit bridging molecules. See Ray S S, Nowak R J, Strokovich K, Brown R H, Jr., Walz T, Lansbury P T, Jr. An intersubunit disulfide bond prevents in vitro aggregation of a superoxide dismutase-1 mutant linked to familial amytrophic lateral sclerosis. Biochemistry 2004; 43:4899-4905. The steps followed were the following:

(1) A structural model of SOD-1 was generated, and hydrogen atoms were added to the model computationally as these are not normally observed in an X-ray diffraction experiment.

(2) A compound structure library was prepared. The library was filtered to remove compounds that are known to be "promiscuous" binders, such as clotrimazole and the library was enriched with compounds that, for example, obey the Lipinski "Rule of 5." Roche O, Schneider P, Zuegge J, et al. Development of a virtual screening method for identification of "frequent hitters" in compound libraries. J Med Chem 2002; 45:137-142; Seidler J, McGovern S L, Doman T N, Shoichet B K. Identification and prediction of promiscuous aggregating inhibitors among known drugs. J Med Chem 2003; 46:4477-4486; and Lipinski C A. Drug-like properties and the causes of poor solubility and poor permeability. J Pharmacol Toxicol Methods 2000; 44:235-249.

(3) Thousands of compounds were docked, computationally, into the desired site on the structure using the Glide package from Schroedinger Corp. Friesner R A, Banks J L, Murphy R B, et al. Glide: a new approach for rapid, accurate docking and scoring. 1. Method and assessment of docking accuracy. J Med Chem 2004; 47:1739-1749.

(4) The empirical interaction energies for all of the docked compounds were evaluated and then the docked compounds were rank ordered according to various criteria, for example principally binding energy, solubility, toxicity; ease of analoging, and cost. Irwin J J, Shoichet B K. ZINC—a free database of commercially available compounds for virtual screening. J Chem Inf Model 2005; 45:177-182.

Figure 13:
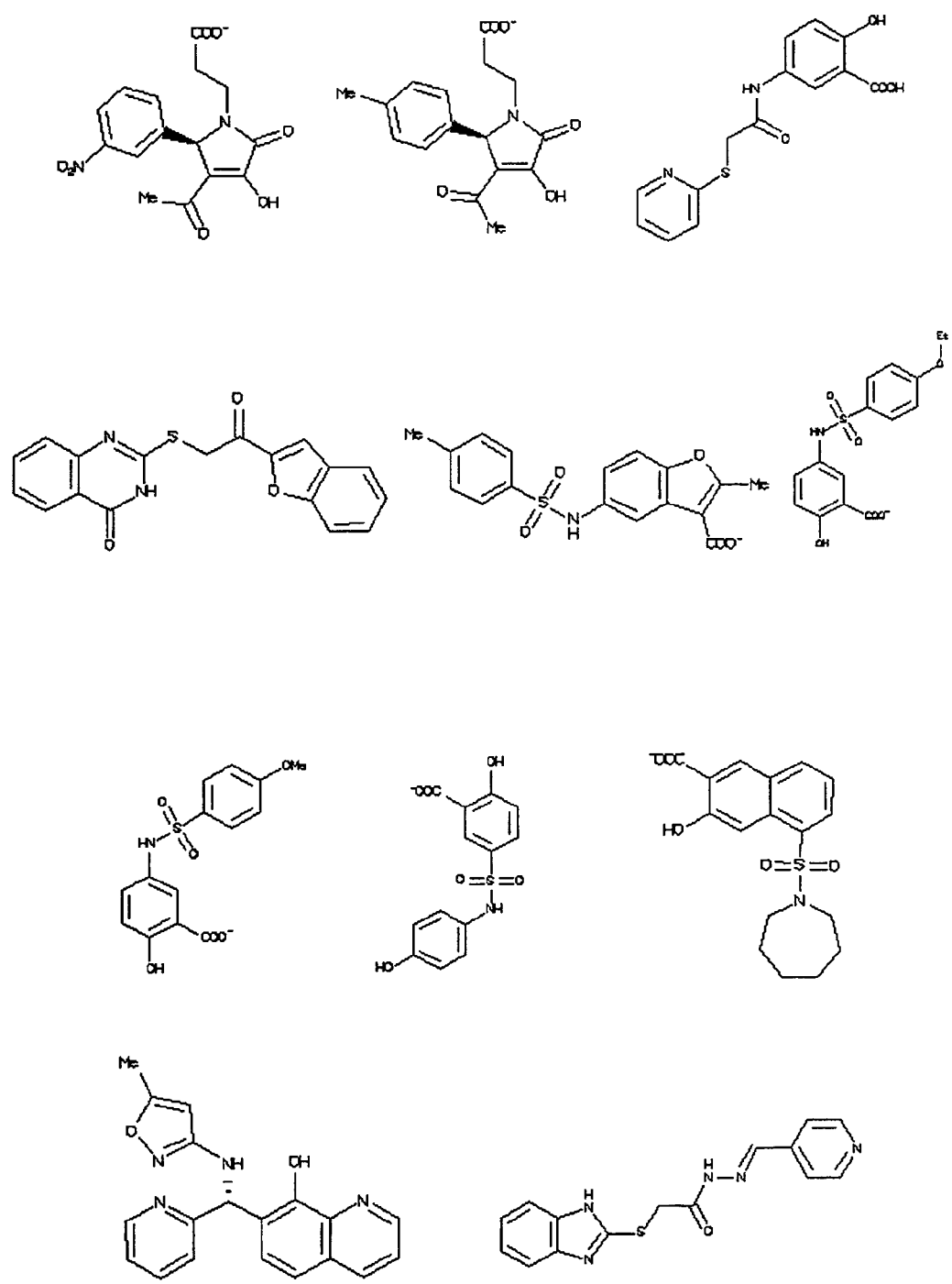
FIG. 13 depicts selected compounds of the invention that bind to SOD-1 Trp 32.
Figure 14:
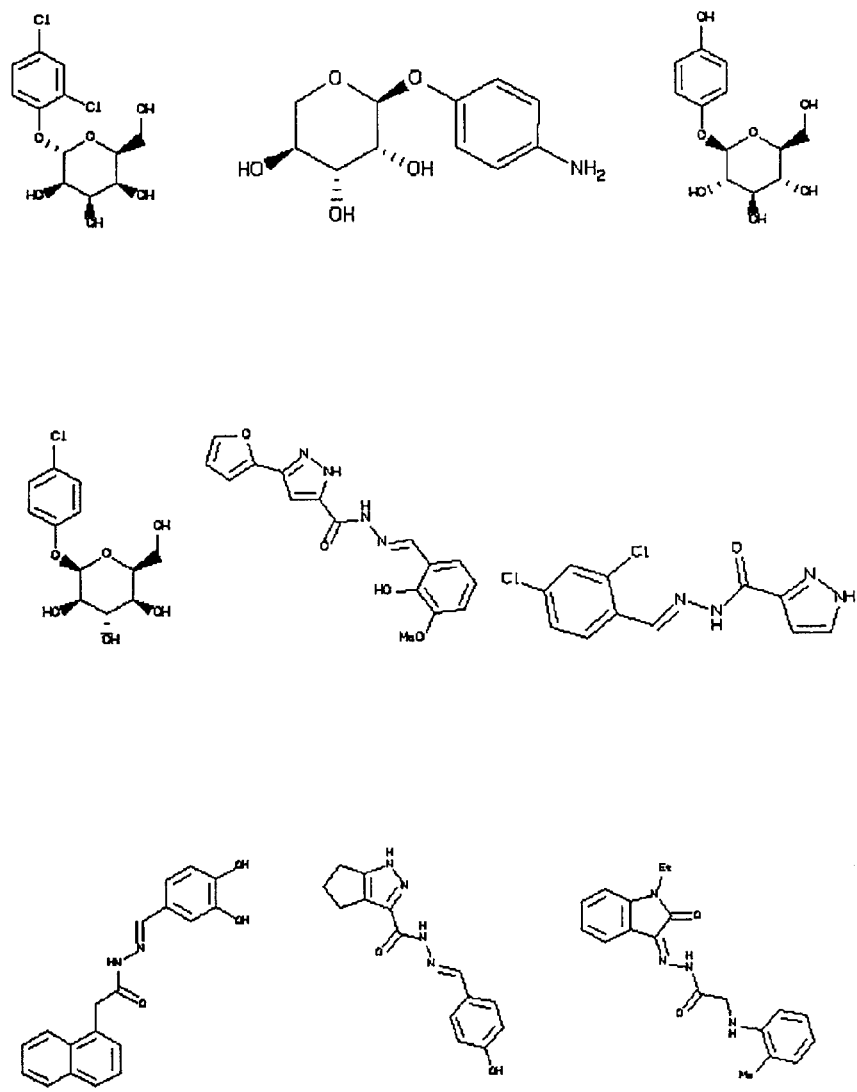
FIG. 14 depicts selected compounds of the invention that bind to SOD-1 Trp 32.
Figure 15:
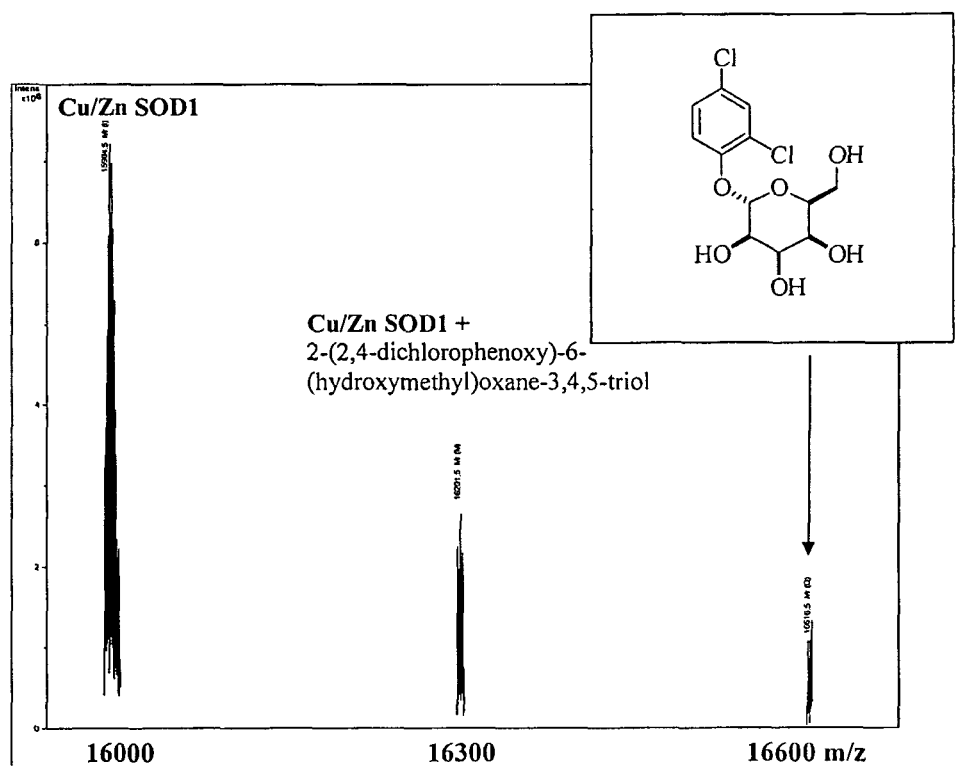
FIG. 15 depicts mass spectrometry data for one binder of SOD-1 Trp32, revealing high affinity in a competitive binding assay.
Figure 16:
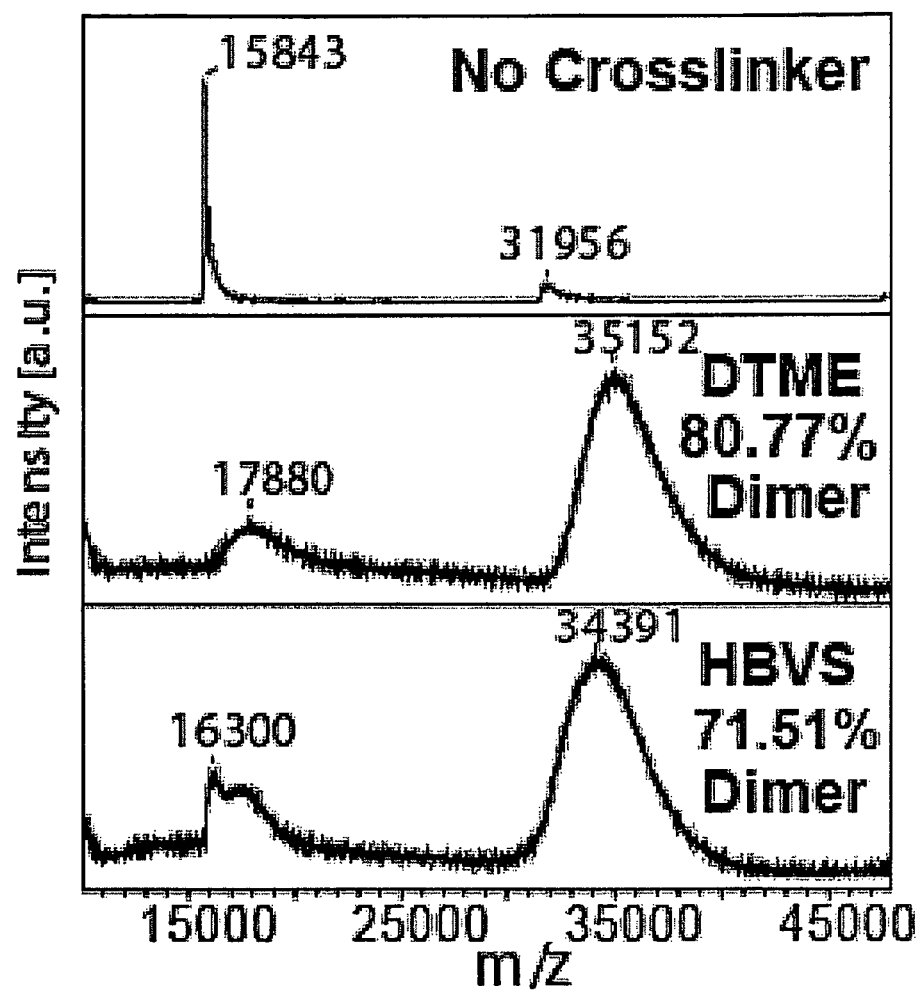
FIG. 16 depicts data showing intersubunit crosslinking of SOD-1 Cys111: intersubunit bridged SOD-1 (top); and implementation of Cys111 bridging-crossliners using both maleimide (DTME) and vinyl sulfone (HBVS) chemistry (bottom).

(5) Some of the top scoring compounds (see FIGS. 13 and 14) were purchased, solubilized in DMSO or water, and tested for their $K_d$ directly by mixing them in different concentrations with SOD-1 Mass spectrometry was used to monitor direct binding. A competitive binding assay was used to rank compound affinity. In this assay four compounds are mixed together and the highest affinity compound contributes the most to the mass spectral intensity of bound products. FIG. 15 illustrates the results for one compound.

One aspect of the invention relates to a compound of formula I, or a pharmaceutically acceptable salt thereof:

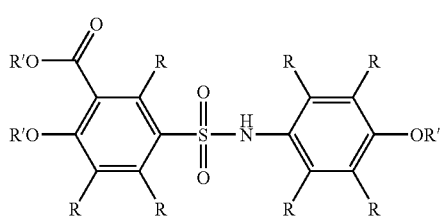

wherein, independently for each occurrence,
R is hydrogen or lower alkyl; and
R' is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R' is hydrogen.

In certain embodiments, the present invention relates to any one of the aforementioned compounds and attendant definitions, provided the compound is not

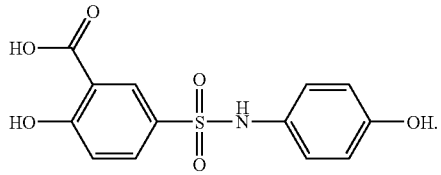 [SMILES: O=C(O)c1cc(S(=O)(=O)Nc2ccc(O)cc2)ccc1O]

One aspect of the invention relates to a compound of formula II, or a pharmaceutically acceptable salt thereof:

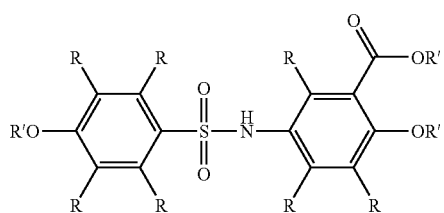

wherein, independently for each occurrence,
R is hydrogen or lower alkyl; and
R' is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R' is hydrogen.

In certain embodiments, the present invention relates to any one of the aforementioned compounds and attendant definitions, provided the compound is not

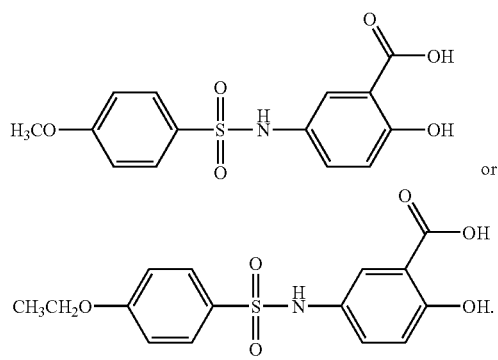

One aspect of the invention relates to a compound of formula III, or a pharmaceutically acceptable salt thereof:

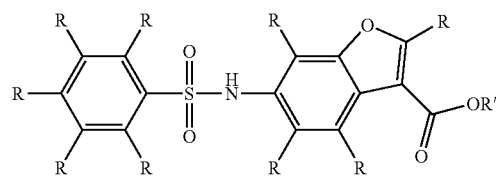

wherein, independently for each occurrence,
R is hydrogen or lower alkyl; and
R' is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R' is hydrogen.

In certain embodiments, the present invention relates to any one of the aforementioned compounds and attendant definitions, provided the compound is not

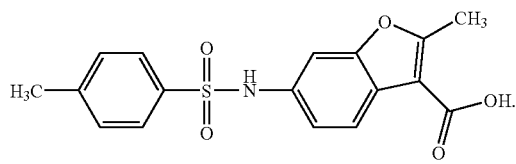

One aspect of the invention relates to a compound of formula IV, or a pharmaceutically acceptable salt thereof:

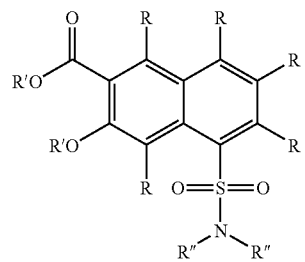

wherein, independently for each occurrence,
R is hydrogen or lower alkyl;
R' is hydrogen or lower alkyl; and
R" is hydrogen, lower alkyl, or the two occurrences of R" taken together are —CH$_2$[CH$_2$]$_2$CH$_2$—, —CH$_2$[CH$_2$]$_3$CH$_2$—, —CH$_2$[CH$_2$]$_4$CH$_2$— or —CH$_2$[CH$_2$]$_5$CH$_2$—.

In certain embodiments, the present invention relates to any one of the aforementioned compounds and attendant definitions, wherein R is hydrogen.

In certain embodiments, the present invention relates to any one of the aforementioned compounds and attendant definitions, wherein R' is hydrogen.

In certain embodiments, the present invention relates to any one of the aforementioned compounds and attendant definitions, wherein R" is hydrogen or lower alkyl.

In certain embodiments, the present invention relates to any one of the aforementioned compounds and attendant definitions, wherein the two occurrences of R" taken together are —CH$_2$[CH$_2$]$_2$CH$_2$—, —CH$_2$[CH$_2$]$_3$CH$_2$—, —CH$_2$[CH$_2$]$_4$CH$_2$— or —CH$_2$[CH$_2$]$_5$CH$_2$—.

In certain embodiments, the present invention relates to any one of the aforementioned compounds and attendant definitions, provided the compound is not

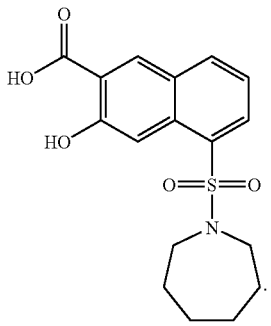 [SMILES: O=C(O)c1cc2cccc(S(=O)(=O)N3CCCCCC3)c2cc1O]

One aspect of the invention relates to a compound of formula V, or a pharmaceutically acceptable salt thereof:

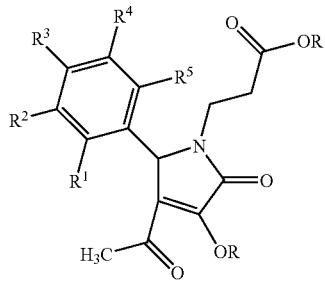

V wherein, independently for each occurrence,
R is hydrogen or lower alkyl;
$R^1$ is hydrogen or lower alkyl;
$R^2$ is hydrogen, nitro or lower alkyl;
$R^3$ is hydrogen or lower alkyl;
$R^4$ is hydrogen or lower alkyl; and
$R^5$ is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein $R^1$ is hydrogen.

In certain embodiments, the present invention relates to any one of the aforementioned compounds and attendant definitions, wherein $R^2$ is nitro.

In certain embodiments, the present invention relates to any one of the aforementioned compounds and attendant definitions, wherein $R^3$ is hydrogen.

In certain embodiments, the present invention relates to any one of the aforementioned compounds and attendant definitions, wherein $R^3$ is lower alkyl.

In certain embodiments, the present invention relates to any one of the aforementioned compounds and attendant definitions, wherein $R^4$ is hydrogen.

In certain embodiments, the present invention relates to any one of the aforementioned compounds and attendant definitions, wherein $R^5$ is hydrogen.

In certain embodiments, the present invention relates to any one of the aforementioned compounds and attendant definitions, provided the compound is not

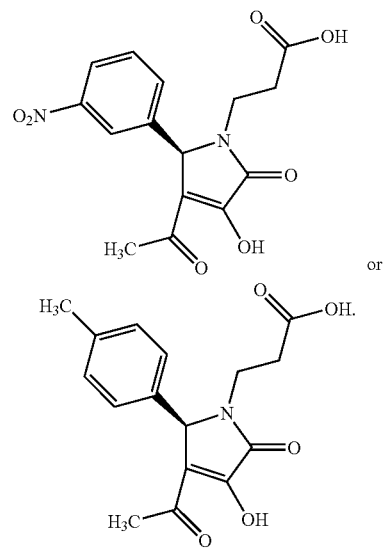

One aspect of the invention relates to a compound of formula V, or a pharmaceutically acceptable salt thereof:

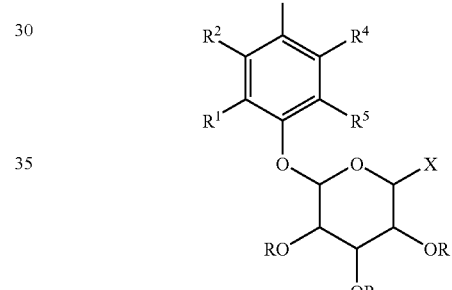

VI wherein, independently for each occurrence,
X is hydrogen or —CH$_2$OR;
R is hydrogen or lower alkyl;
$R^1$ is hydrogen or lower alkyl;
$R^2$ is hydrogen or lower alkyl;
$R^3$ is hydrogen, lower alkyl, —Cl, —OR, or NR$_2$;
$R^4$ is hydrogen or lower alkyl; and
$R^5$ is hydrogen, —Cl, or lower alkyl.

In certain embodiments, the present invention relates to any one of the aforementioned compounds and attendant definitions, wherein X is hydrogen.

In certain embodiments, the present invention relates to any one of the aforementioned compounds and attendant definitions, wherein X is —CH$_2$OH.

In certain embodiments, the present invention relates to any one of the aforementioned compounds and attendant definitions, wherein R is hydrogen.

In certain embodiments, the present invention relates to any one of the aforementioned compounds and attendant definitions, wherein $R^1$ is hydrogen.

In certain embodiments, the present invention relates to any one of the aforementioned compounds and attendant definitions, wherein $R^2$ is hydrogen.

In certain embodiments, the present invention relates to any one of the aforementioned compounds and attendant definitions, wherein $R^3$ is —Cl.

In certain embodiments, the present invention relates to any one of the aforementioned compounds and attendant definitions, wherein $R^3$ is —OH.

In certain embodiments, the present invention relates to any one of the aforementioned compounds and attendant definitions, wherein $R^3$ is —NH$_2$.

In certain embodiments, the present invention relates to any one of the aforementioned compounds and attendant definitions, wherein $R^4$ is hydrogen.

In certain embodiments, the present invention relates to any one of the aforementioned compounds and attendant definitions, wherein $R^5$ is hydrogen.

In certain embodiments, the present invention relates to any one of the aforementioned compounds and attendant definitions, wherein $R^5$ is —Cl.

In certain embodiments, the present invention relates to any one of the aforementioned compounds and attendant definitions, provided the compound is not

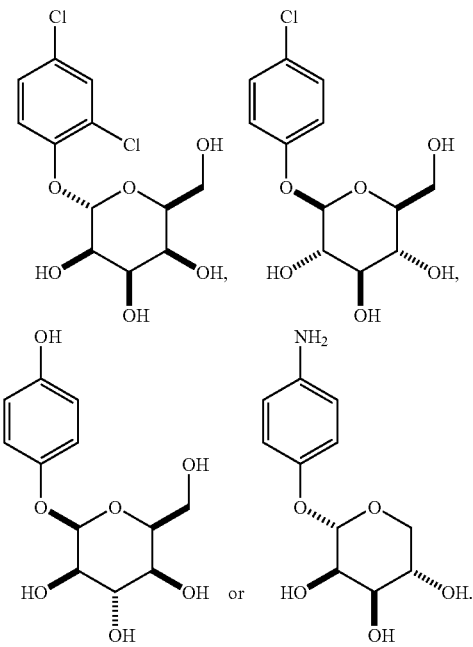

One aspect of the invention relates to a compound of formula VII, or a pharmaceutically acceptable salt thereof:

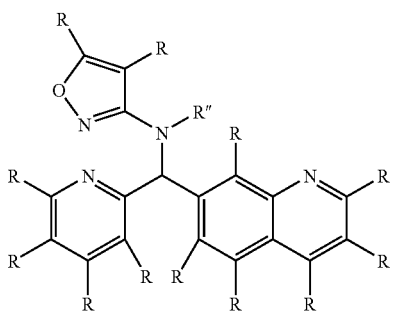

VII wherein, independently for each occurrence,
R is hydrogen or lower alkyl; and
R" is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R" is hydrogen.

In certain embodiments, the present invention relates to any one of the aforementioned compounds and attendant definitions, provided the compound is not

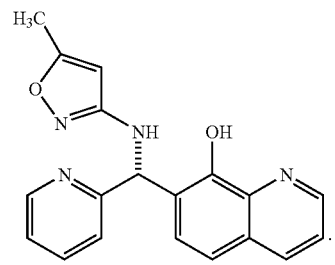

One aspect of the invention relates to a compound of formula VIII, or a pharmaceutically acceptable salt thereof:

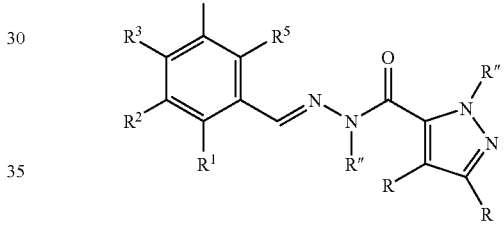

VIII wherein, independently for each occurrence,
R is hydrogen or lower alkyl;
R" is hydrogen or lower alkyl;
$R^1$ is hydrogen or lower alkyl;
$R^2$ is hydrogen or lower alkyl;
$R^3$ is hydrogen, lower alkyl, —Cl, or —OR;
$R^4$ is hydrogen, lower alkyl, —Cl, or —OR; and
$R^5$ is hydrogen, —Cl, or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R" is hydrogen.

In certain embodiments, the present invention relates to any one of the aforementioned compounds and attendant definitions, wherein $R^1$ is hydrogen.

In certain embodiments, the present invention relates to any one of the aforementioned compounds and attendant definitions, wherein $R^2$ is hydrogen.

In certain embodiments, the present invention relates to any one of the aforementioned compounds and attendant definitions, wherein $R^3$ is hydrogen.

In certain embodiments, the present invention relates to any one of the aforementioned compounds and attendant definitions, wherein $R^3$ is —OH.

In certain embodiments, the present invention relates to any one of the aforementioned compounds and attendant definitions, wherein $R^3$ is —Cl.

In certain embodiments, the present invention relates to any one of the aforementioned compounds and attendant definitions, wherein R⁴ is hydrogen.

In certain embodiments, the present invention relates to any one of the aforementioned compounds and attendant definitions, wherein R⁴ is —OCH₃.

In certain embodiments, the present invention relates to any one of the aforementioned compounds and attendant definitions, wherein R⁵ is hydrogen.

In certain embodiments, the present invention relates to any one of the aforementioned compounds and attendant definitions, wherein R⁵ is —OH.

In certain embodiments, the present invention relates to any one of the aforementioned compounds and attendant definitions, wherein R⁵ is —Cl.

In certain embodiments, the present invention relates to any one of the aforementioned compounds and attendant definitions, provided the compound is not

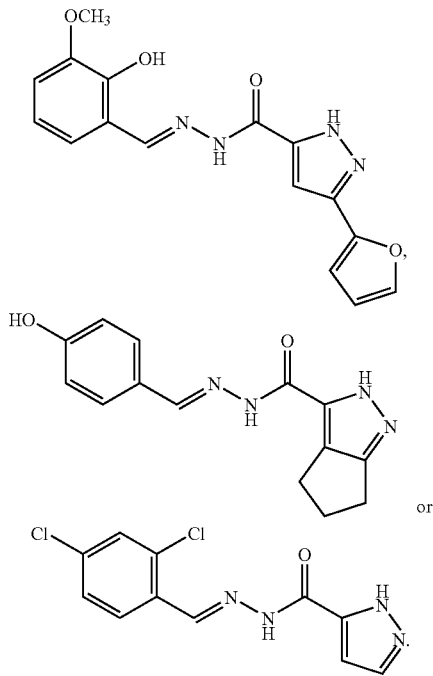

One aspect of the invention relates to a compound of formula IX, or a pharmaceutically acceptable salt thereof:

IX

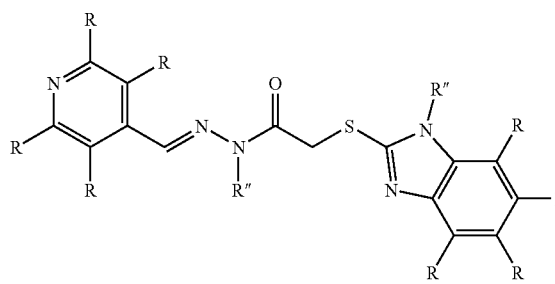

wherein, independently for each occurrence,
R is hydrogen or lower alkyl; and
R" is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R" is hydrogen.

In certain embodiments, the present invention relates to any one of the aforementioned compounds and attendant definitions, provided the compound is not

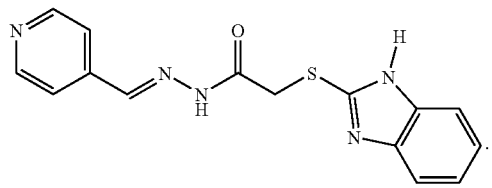 [SMILES: O=C(CSc1nc2ccccc2[nH]1)N/N=C/c1ccncc1]

One aspect of the invention relates to a compound of formula X, or a pharmaceutically acceptable salt thereof:

X

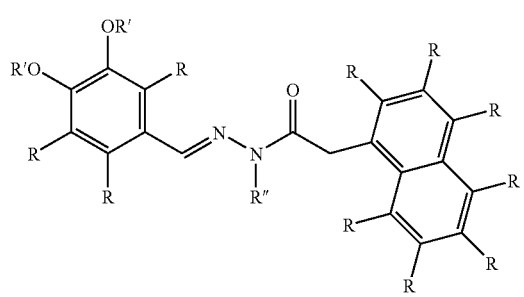

wherein, independently for each occurrence,
R is hydrogen or lower alkyl;
R' is hydrogen or lower alkyl; and
R" is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R' is hydrogen.

In certain embodiments, the present invention relates to any one of the aforementioned compounds and attendant definitions, wherein R" is hydrogen.

In certain embodiments, the present invention relates to any one of the aforementioned compounds and attendant definitions, provided the compound is not

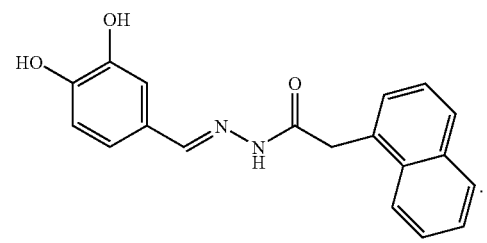 [SMILES: O=C(Cc1cccc2ccccc12)N/N=C/c1ccc(O)c(O)c1]

One aspect of the invention relates to a compound of formula XI, or a pharmaceutically acceptable salt thereof:

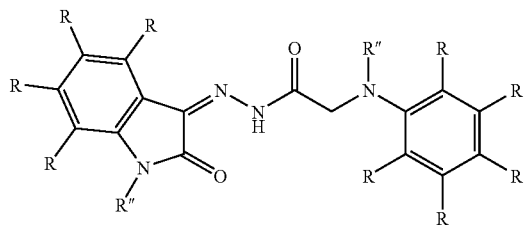

wherein, independently for each occurrence,
R is hydrogen or lower alkyl; and
R″ is hydrogen or lower alkyl.

In certain embodiments, the present invention relates to any one of the aforementioned compounds and attendant definitions, wherein R is hydrogen.

In certain embodiments, the present invention relates to any one of the aforementioned compounds and attendant definitions, wherein R″ is hydrogen.

In certain embodiments, the present invention relates to any one of the aforementioned compounds and attendant definitions, provided the compound is not

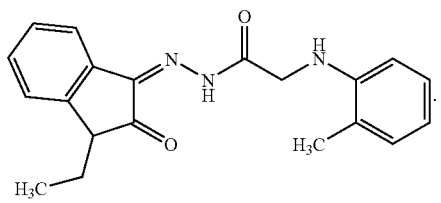 [SMILES: CCC1C(=O)/C(=N\NC(=O)CNc2ccccc2C)c2ccccc21]

In certain embodiments, the present invention relates to any one of the aforementioned compounds and attendant definitions, provided the compound is not selected from the group consisting of 2-(2,4-dichlorophenoxy)-6-(hydroxymethyl)oxane-3,4,5-triol; 3-[3-acetyl-4-hydroxy-2-(4-methylphenyl)-5-oxo-2H-pyrrol-1-yl]propanoate; 2-hydroxy-5-[(2-pyridin-2-ylsulfanylacetyl)amino]benzoate; (2S,3R,4R,5S,6R)-2-(hydroxymethyl)-6-(4-hydroxyphenoxy)oxane-3,4,5-triol; (2S,3R,4R,5S)-2-(4-aminophenoxy)oxane-3,4,5-triol; 2-hydroxy-5-[(4-hydroxyphenyl)sulfamoyl]benzoate; 3-[3-acetyl-2-(3-nitrophenyl)-4,5-dioxopyrrolidin-1-yl]propanoate; (2R,3R,4S,5S,6S)-2-(4-chlorophenoxy)-6-(hydroxymethypoxane-3,4,5-triol; 2-[2-(1-benzofuran-2-yl)-2-oxoethyl]sulfanyl-1H-quinazolin-4-one; 5-[(4-ethoxyphenyl)sulfonylamino]-2-hydroxybenzoate; 5-(2-furanyl)-N-[(2-hydroxy-3-methoxyphenyl)methylideneamino]-1H-pyrazole-3-carboxamide; 2-(1H-benzimidazol-2-ylsulfanyl)-N-(pyridin-4-ylmethylideneamino)acetamide; 2-methyl-5-[(4-methylphenyl)sulfonylamino]-1-benzofuran-3-carboxylic acid; N-[(3,4-dihydroxyphenyl)methylideneamino]-2-naphthalen-1-ylacetamide; 7-[[(5-methyl-1,2-oxazol-3-yl)amino]-pyridin-2-ylmethyl]quinolin-8-ol; 5-(azepan-1-ylsulfonyl)-3-hydroxynaphthalene-2-carboxylate; 2-[(2-methylphenyl)amino]-N-[(1-ethyl-2-oxoindol-3-ylidene)amino]acetamide; N-[(4-hydroxyphenyl)methylideneamino]-1,4,5,6-tetrahydrocyclopenta[d]pyrazole-3-carboxamide; 2-hydroxy-5-{[(4-methoxyphenyl)sulfonyl]amino}benzoic acid; and N-[(2,4-dichlorophenyl)methylideneamino]-2H-pyrazole-3-carboxamide.

One aspect of the invention relates to a method of treating or preventing a neurodegenerative disease, comprising the step of administering to a patient in need thereof a therapeutically effective amount of formula I, or a pharmaceutically acceptable salt thereof:

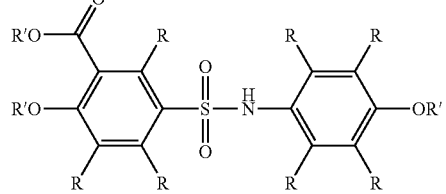

wherein, independently for each occurrence,
R is hydrogen or lower alkyl; and
R' is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R' is hydrogen.

In certain embodiments, the present invention relates to any one of the aforementioned methods and attendant definitions, wherein the compound is

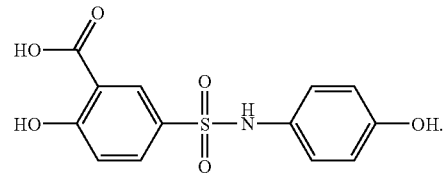 [SMILES: O=C(O)c1cc(S(=O)(=O)Nc2ccc(O)cc2)ccc1O]

One aspect of the invention relates to a method of treating or preventing a neurodegenerative disease, comprising the step of administering to a patient in need thereof a therapeutically effective amount of formula II, or a pharmaceutically acceptable salt thereof:

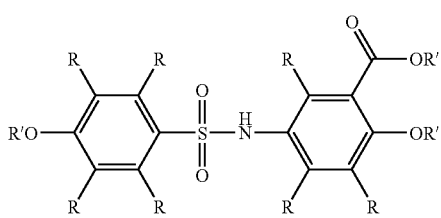

wherein, independently for each occurrence,
R is hydrogen or lower alkyl; and
R' is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R' is hydrogen.

In certain embodiments, the present invention relates to any one of the aforementioned methods and attendant definitions, wherein the compound is

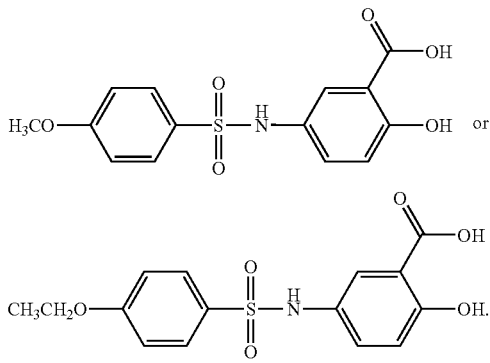

One aspect of the invention relates to a method of treating or preventing a neurodegenerative disease, comprising the step of administering to a patient in need thereof a therapeutically effective amount of formula III, or a pharmaceutically acceptable salt thereof:

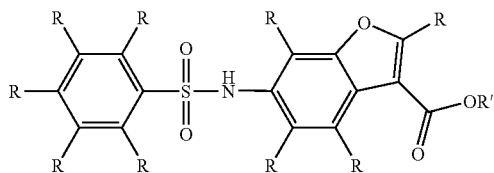

wherein, independently for each occurrence,

R is hydrogen or lower alkyl; and
R' is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R' is hydrogen.

In certain embodiments, the present invention relates to any one of the aforementioned methods and attendant definitions, wherein the compound is

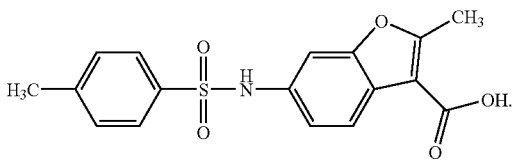 [SMILES: Cc1ccc(S(=O)(=O)Nc2ccc3c(C(=O)O)c(C)oc3c2)cc1]

One aspect of the invention relates to a method of treating or preventing a neurodegenerative disease, comprising the step of administering to a patient in need thereof a therapeutically effective amount of formula IV, or a pharmaceutically acceptable salt thereof:

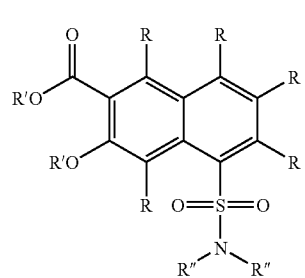

wherein, independently for each occurrence,

R is hydrogen or lower alkyl;
R' is hydrogen or lower alkyl; and
R" is hydrogen, lower alkyl, or the two occurrences of R" taken together are $-CH_2[CH_2]_2CH_2-$, $-CH_2[CH_2]_3CH_2-$, $-CH_2[CH_2]_4CH_2-$ or $-CH_2[CH_2]_5CH_2-$.

In certain embodiments, the present invention relates to any one of the aforementioned methods and attendant definitions, wherein R is hydrogen.

In certain embodiments, the present invention relates to any one of the aforementioned methods and attendant definitions, wherein R' is hydrogen.

In certain embodiments, the present invention relates to any one of the aforementioned methods and attendant definitions, wherein R" is hydrogen or lower alkyl.

In certain embodiments, the present invention relates to any one of the aforementioned methods and attendant definitions, wherein the two occurrences of R" taken together are $-CH_2[CH_2]_2CH_2-$, $-CH_2[CH_2]_3CH_2-$, $-CH_2[CH_2]_4CH_2-$ or $-CH_2[CH_2]_5CH_2-$.

In certain embodiments, the present invention relates to any one of the aforementioned methods and attendant definitions, wherein the compound is

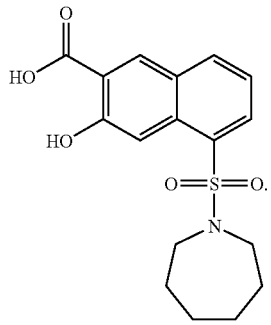 [SMILES: O=C(O)c1cc2cccc(S(=O)(=O)N3CCCCCC3)c2cc1O]

One aspect of the invention relates to a method of treating or preventing a neurodegenerative disease, comprising the step of administering to a patient in need thereof a therapeutically effective amount of formula V, or a pharmaceutically acceptable salt thereof:

V

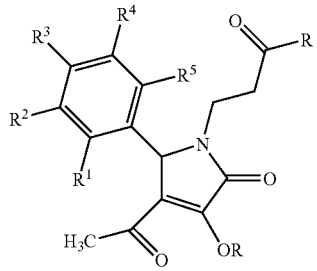

wherein, independently for each occurrence,
R is hydrogen or lower alkyl;
$R^1$ is hydrogen or lower alkyl;
$R^2$ is hydrogen, nitro or lower alkyl;
$R^3$ is hydrogen or lower alkyl;
$R^4$ is hydrogen or lower alkyl; and
$R^5$ is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein $R^1$ is hydrogen.

In certain embodiments, the present invention relates to any one of the aforementioned methods and attendant definitions, wherein $R^2$ is nitro.

In certain embodiments, the present invention relates to any one of the aforementioned methods and attendant definitions, wherein $R^3$ is hydrogen.

In certain embodiments, the present invention relates to any one of the aforementioned methods and attendant definitions, wherein $R^3$ is lower alkyl.

In certain embodiments, the present invention relates to any one of the aforementioned methods and attendant definitions, wherein $R^4$ is hydrogen.

In certain embodiments, the present invention relates to any one of the aforementioned methods and attendant definitions, wherein $R^5$ is hydrogen.

In certain embodiments, the present invention relates to any one of the aforementioned methods and attendant definitions, wherein the compound is

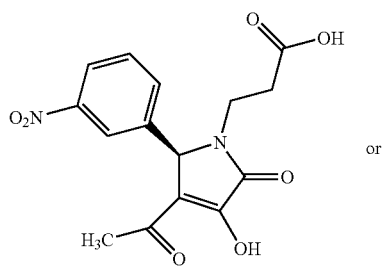

or

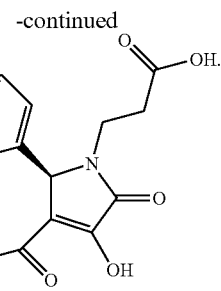

One aspect of the invention relates to a method of treating or preventing a neurodegenerative disease, comprising the step of administering to a patient in need thereof a therapeutically effective amount of formula V, or a pharmaceutically acceptable salt thereof:

VI

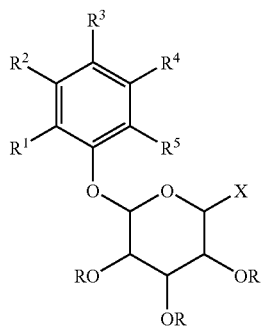

wherein, independently for each occurrence,
X is hydrogen or —$CH_2OR$;
R is hydrogen or lower alkyl;
$R^1$ is hydrogen or lower alkyl;
$R^2$ is hydrogen or lower alkyl;
$R^3$ is hydrogen, lower alkyl, —Cl, —OR, or $NR_2$;
$R^4$ is hydrogen or lower alkyl; and
$R^5$ is hydrogen, —Cl, or lower alkyl.

In certain embodiments, the present invention relates to any one of the aforementioned methods and attendant definitions, wherein X is hydrogen.

In certain embodiments, the present invention relates to any one of the aforementioned methods and attendant definitions, wherein X is —$CH_2OH$.

In certain embodiments, the present invention relates to any one of the aforementioned methods and attendant definitions, wherein R is hydrogen.

In certain embodiments, the present invention relates to any one of the aforementioned methods and attendant definitions, wherein $R^1$ is hydrogen.

In certain embodiments, the present invention relates to any one of the aforementioned methods and attendant definitions, wherein $R^2$ is hydrogen.

In certain embodiments, the present invention relates to any one of the aforementioned methods and attendant definitions, wherein $R^3$ is —Cl.

In certain embodiments, the present invention relates to any one of the aforementioned methods and attendant definitions, wherein $R^3$ is —OH.

In certain embodiments, the present invention relates to any one of the aforementioned methods and attendant definitions, wherein $R^3$ is —$NH_2$.

In certain embodiments, the present invention relates to any one of the aforementioned methods and attendant definitions, wherein $R^4$ is hydrogen.

In certain embodiments, the present invention relates to any one of the aforementioned methods and attendant definitions, wherein $R^5$ is hydrogen.

In certain embodiments, the present invention relates to any one of the aforementioned methods and attendant definitions, wherein $R^5$ is —Cl.

In certain embodiments, the present invention relates to any one of the aforementioned methods and attendant definitions, wherein the compound is

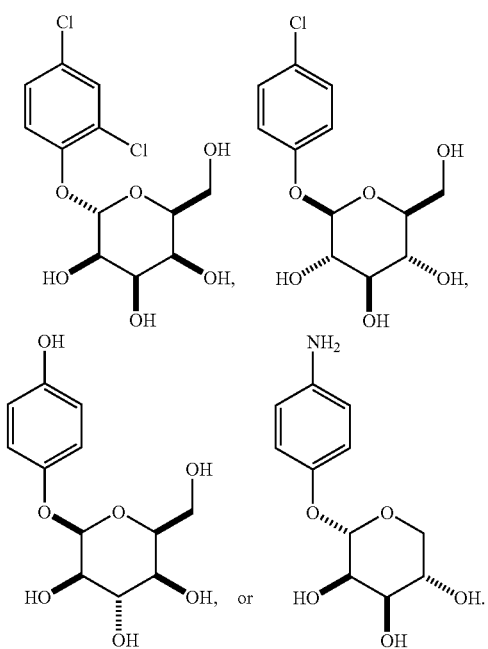

One aspect of the invention relates to a method of treating or preventing a neurodegenerative disease, comprising the step of administering to a patient in need thereof a therapeutically effective amount of formula VII, or a pharmaceutically acceptable salt thereof:

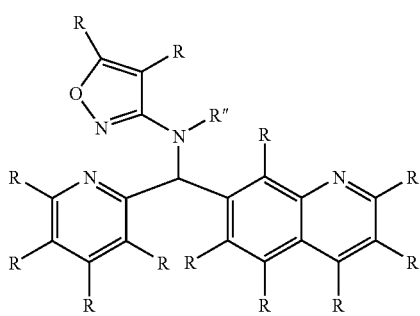

VII wherein, independently for each occurrence,
R is hydrogen or lower alkyl; and
R" is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R" is hydrogen.

In certain embodiments, the present invention relates to any one of the aforementioned methods and attendant definitions, wherein the compound is

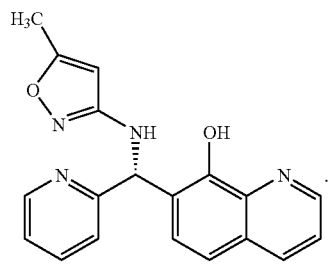 [SMILES: Cc1cc(N[C@@H](c2ccccn2)c2ccc3cccnc3c2O)no1 ; "."]

One aspect of the invention relates to a method of treating or preventing a neurodegenerative disease, comprising the step of administering to a patient in need thereof a therapeutically effective amount of formula VIII, or a pharmaceutically acceptable salt thereof:

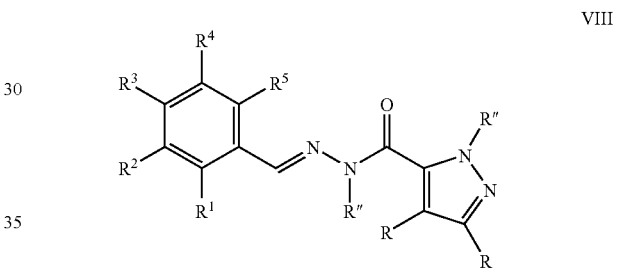

VIII wherein, independently for each occurrence,
R is hydrogen or lower alkyl;
R" is hydrogen or lower alkyl;
$R^1$ is hydrogen or lower alkyl;
$R^2$ is hydrogen or lower alkyl;
$R^3$ is hydrogen, lower alkyl, —Cl, or —OR;
$R^4$ is hydrogen, lower alkyl, —Cl, or —OR; and
$R^5$ is hydrogen, —Cl, or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R" is hydrogen.

In certain embodiments, the present invention relates to any one of the aforementioned methods and attendant definitions, wherein $R^1$ is hydrogen.

In certain embodiments, the present invention relates to any one of the aforementioned methods and attendant definitions, wherein $R^2$ is hydrogen.

In certain embodiments, the present invention relates to any one of the aforementioned methods and attendant definitions, wherein $R^3$ is hydrogen.

In certain embodiments, the present invention relates to any one of the aforementioned methods and attendant definitions, wherein $R^3$ is —OH.

In certain embodiments, the present invention relates to any one of the aforementioned methods and attendant definitions, wherein $R^3$ is —Cl.

In certain embodiments, the present invention relates to any one of the aforementioned methods and attendant definitions, wherein $R^4$ is hydrogen.

In certain embodiments, the present invention relates to any one of the aforementioned methods and attendant definitions, wherein $R^4$ is —$OCH_3$.

In certain embodiments, the present invention relates to any one of the aforementioned methods and attendant definitions, wherein $R^5$ is hydrogen.

In certain embodiments, the present invention relates to any one of the aforementioned methods and attendant definitions, wherein $R^5$ is —OH.

In certain embodiments, the present invention relates to any one of the aforementioned methods and attendant definitions, wherein $R^5$ is —Cl.

In certain embodiments, the present invention relates to any one of the aforementioned methods and attendant definitions, wherein the compound is

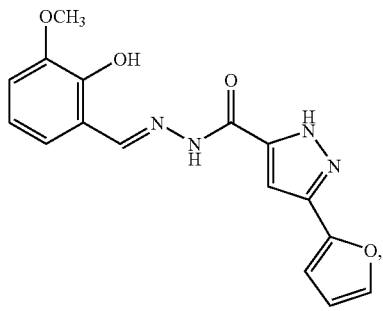

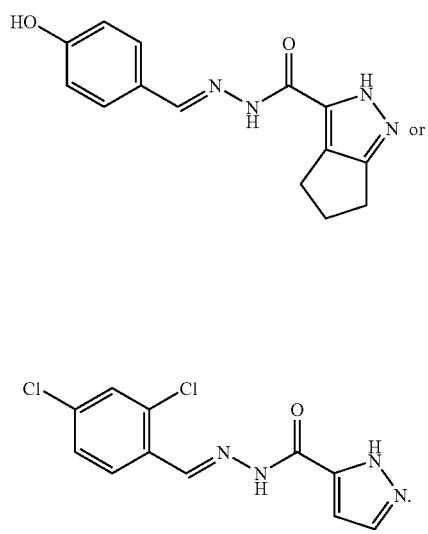

One aspect of the invention relates to a method of treating or preventing a neurodegenerative disease, comprising the step of administering to a patient in need thereof a therapeutically effective amount of formula IX, or a pharmaceutically acceptable salt thereof:

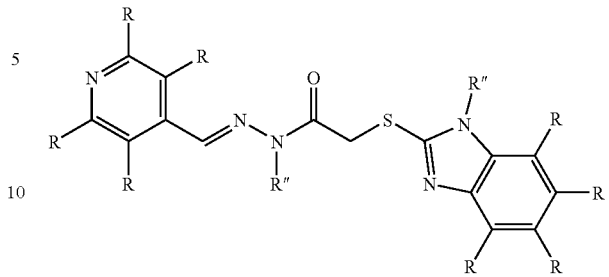

IX wherein, independently for each occurrence,
R is hydrogen or lower alkyl; and
R" is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R" is hydrogen.

In certain embodiments, the present invention relates to any one of the aforementioned methods and attendant definitions, wherein the compound is

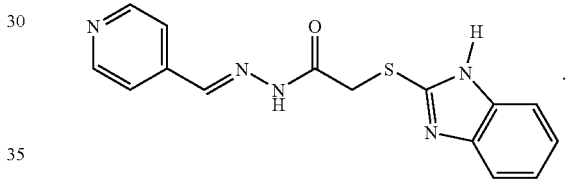

One aspect of the invention relates to a method of treating or preventing a neurodegenerative disease, comprising the step of administering to a patient in need thereof a therapeutically effective amount of formula X, or a pharmaceutically acceptable salt thereof:

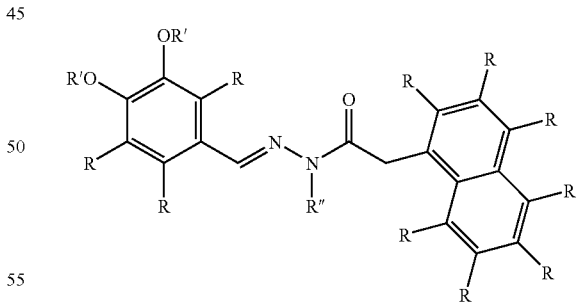

X wherein, independently for each occurrence,
R is hydrogen or lower alkyl;
R' is hydrogen or lower alkyl; and
R" is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R' is hydrogen.

In certain embodiments, the present invention relates to any one of the aforementioned methods and attendant definitions, wherein R" is hydrogen.

In certain embodiments, the present invention relates to any one of the aforementioned methods and attendant definitions, wherein the compound is

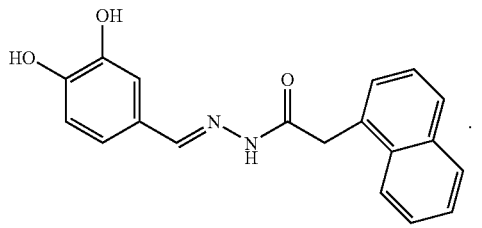 [SMILES: O=C(Cc1cccc2ccccc12)N/N=C/c1ccc(O)c(O)c1 ; "."]

One aspect of the invention relates to a method of treating or preventing a neurodegenerative disease, comprising the step of administering to a patient in need thereof a therapeutically effective amount of formula XI, or a pharmaceutically acceptable salt thereof:

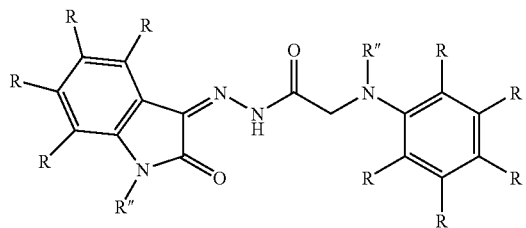

wherein, independently for each occurrence,
R is hydrogen or lower alkyl; and
R" is hydrogen or lower alkyl.

In certain embodiments, the present invention relates to any one of the aforementioned methods and attendant definitions, wherein R is hydrogen.

In certain embodiments, the present invention relates to any one of the aforementioned methods and attendant definitions, wherein R" is hydrogen.

In certain embodiments, the present invention relates to any one of the aforementioned methods and attendant definitions, wherein the compound is

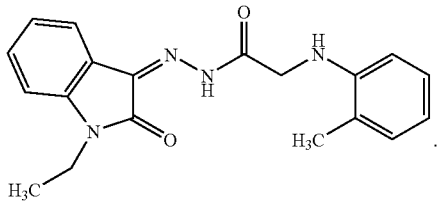 [SMILES: CCN1C(=O)/C(=N\NC(=O)CNc2ccccc2C)c2ccccc21 ; "."]

One aspect of the invention relates to a method of treating or preventing a neurodegenerative disease, comprising the step of administering to a patient in need thereof a therapeutically effective amount of a compound selected from the group consisting of 2-(2,4-dichlorophenoxy)-6-(hydroxymethyl)oxane-3,4,5-triol; 3-[3-acetyl-4-hydroxy-2-(4-methylphenyl)-5-oxo-2H-pyrrol-1-yl]propanoate; 2-hydroxy-5-[(2-pyridin-2-ylsulfanylacetyl)amino]benzoate; (2S,3R,4R,5S,6R)-2-(hydroxymethyl)-6-(4-hydroxyphenoxy)oxane-3,4,5-triol; (2S,3R,4R,5S)-2-(4-aminophenoxy)oxane-3,4,5-triol; 2-hydroxy-5-[(4-hydroxyphenyl)sulfamoyl]benzoate; 3-[3-acetyl-2-(3-nitrophenyl)-4,5-dioxopyrrolidin-1-yl]propanoate; (2R,3R,4S,5S,6S)-2-(4-chlorophenoxy)-6-(hydroxymethyl)oxane-3,4,5-triol; 2-[2-(1-benzofuran-2-yl)-2-oxoethyl]sulfanyl-1H-quinazolin-4-one; 5-[(4-ethoxyphenyl)sulfonylamino]-2-hydroxybenzoate; 5-(2-furanyl)-N-[(2-hydroxy-3-methoxyphenyl) methylideneamino]-1H-pyrazole-3-carboxamide; 2-(1H-benzimidazol-2-ylsulfanyl)-N-(pyridin-4-ylmethylideneamino)acetamide; 2-methyl-5-[(4-methylphenyl)sulfonylamino]-1-benzofuran-3-carboxylic acid; N-[(3,4-dihydroxyphenyl)methylideneamino]-2-naphthalen-1-ylacetamide; 7-[[(5-methyl-1,2-oxazol-3-yl) amino]-pyridin-2-ylmethyl]quinolin-8-ol; 5-(azepan-1-ylsulfonyl)-3-hydroxynaphthalene-2-carboxylate; 2-[(2-methylphenyl)amino]-N-[(1-ethyl-2-oxoindol-3-ylidene) amino]acetamide; N-[(4-hydroxyphenyl) methylideneamino]-1,4,5,6-tetrahydrocyclopenta[d] pyrazole-3-carboxamide; 2-hydroxy-5-{[(4-methoxyphenyl)sulfonyl]amino}benzoic acid; and N-[(2,4-dichlorophenyl)methylideneamino]-2H-pyrazole-3-carboxamide.

In certain embodiments, the present invention relates to any one of the aforementioned methods and attendant definitions, wherein the neurodegenerative disease is Alzheimer, Parkinson, or Amyotrophic lateral sclerosis.

In certain embodiments, the present invention relates to any one of the aforementioned methods and attendant definitions, wherein the neurodegenerative disease is Amyotrophic lateral sclerosis.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH-buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

DEFINITIONS

For convenience, the meaning of certain terms and phrases employed in the specification, examples, and appended claims are provided below. Unless defined otherwise, all technical and scientific terms used herein have the same meaning as commonly understood by one of ordinary skill in the art to which this invention belongs.

The articles "a" and "an" are used herein to refer to one or more than one (i.e., to at least one) of the grammatical object of the article.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, unless clearly indicated to the contrary, in any methods claimed herein that include more than one step or act, the order of the steps or acts of the method is not necessarily limited to the order in which the steps or acts of the method are recited.

The term "amino acid" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid" further includes analogs, derivatives and congeners of any specific amino acid referred to herein, as well as C-terminal or N-terminal protected amino acid derivatives (e.g., modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1 methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (d) and (1) stereoisomers of such amino acids when the structure of the amino acid admits of stereoisomeric forms. The configuration of the amino acids and amino acid residues herein are designated by the appropriate symbols (d), (l) or (dl), furthermore when the configuration is not designated the amino acid or residue can have the configuration (d), (l) or (dl). It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (d) or (l) stereoisomers.

The term "conservative substitutions" refers to changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; valine-leucine-isoleucine-methionine; phenylalanine-tyrosine; phenylalanine-tyrosine-tryptophan; lysine-arginine; and histidine-lysine-arginine.

"Equivalent" when used to describe nucleic acids or nucleotide sequences refers to nucleotide sequences encoding functionally equivalent polypeptides. Equivalent nucleotide sequences will include sequences that differ by one or more nucleotide substitution, addition or deletion, such as an allelic variant; and will, therefore, include sequences that differ due to the degeneracy of the genetic code. For example, nucleic acid variants may include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions.

Variant peptides may be covalently prepared by direct chemical synthesis using methods well known in the art. Variants may further include, for example, deletions, insertions or substitutions of residues within the amino acid sequence. Any combination of deletion, insertion, and substitution may also be made to arrive at the final construct, provided that the final construct possesses the desired activity. These variants may be prepared by site-directed mutagenesis, (as exemplified by Adelman et al., DNA 2: 183 (1983)) of the nucleotides in the DNA encoding the peptide molecule thereby producing DNA encoding the variant and thereafter expressing the DNA in recombinant cell culture. The variants typically exhibit the same qualitative biological activity as wild type polypeptides. It is known in the art that one may also synthesize all possible single amino acid substitutions of a known polypeptide (Geysen et al., Proc. Nat. Acad. Sci. (USA) 18:3998-4002 (1984)). While the effects of different substitutions are not always additive, it is reasonable to expect that two favorable or neutral single substitutions at different residue positions in a polypeptide can safely be combined without losing any protein activity. Methods for the preparation of degenerate polypeptides are as described in Rutter, U.S. Pat. No. 5,010,175; Haughter et al., Proc. Nat. Acad. Sci. (USA) 82:5131-5135 (1985); Geysen et al., Proc. Nat. Acad. Sci. (USA) 18:3998-4002 (1984); WO86/06487; and WO86/00991.

In devising a substitution strategy, a person of ordinary skill would determine which residues to vary and which amino acids or classes of amino acids are suitable replacements. One may also take into account studies of sequence variations in families or naturally occurring homologous proteins. Certain amino acid substitutions are more often tolerated than others, and these are often correlated with similarities in size, charge, etc., between the original amino acid and its replacement. Insertions or deletions of amino acids may also be made, as described above. The substitutions are preferably conservative, see, e.g., Schulz et al., Principle of Protein Structure (Springer-Verlag, New York (1978)); and Creighton, Proteins: Structure and Molecular Properties (W. H. Freeman & Co., San Francisco (1983)); both of which are hereby incorporated by reference in their entireties.

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted religation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., hit. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, "Handbook of Chemistry and Physics", 67th Ed., 1986-87, inside cover.

As used herein, the term "subject" or "individual" refers to a human or other vertebrate animal. It is intended that the term encompass "patients."

EXEMPLIFICATION

It should be understood that the above-described embodiments and the following examples are given by way of illustration, not limitation. Various changes and modifications within the scope of the present invention will become apparent to those skilled in the art from the present description.

Example 1

Blood Samples

B6SJL-TgN(SOD-1wt)2Gur and B6SJL-TgN(SOD-1G93A)1Gur mice, transgenic for human SOD-1wt and SOD-1G93A respectively, were established from breeding pairs obtained from The Jackson Laboratory (Bar Harbor, Me.). Mice hemizygous for the transgene were obtained by breeding hemizygous males with non-transgenic B6SJL females. Human SOD-1 transgenes were identified by PCR as previously described. See Shinder, G. A., Lacourse, M. C., Minotti, S., and Durham, H. D. (2001) J. Biol. Chem. 276, 12791-12796. Blood samples were obtained by cardiac puncture following anesthesia with intraperitoneal injection of ketamine/xylazine. Human blood samples were obtained by finger prick, with 200 µl of blood added to an equal volume of 7.6% sodium citrate in phosphate-buffered saline (PBS), pH 7.2 (citrate PBS). Erythrocytes were separated from plasma by centrifugation at 600×g for 5 min, washed twice by resuspension in a 20× volume of citrate PBS, and lysed by resuspension in a 5× volume of hypo-osmotic solution of 10 mM ammonium bicarbonate, pH 8.0, using fast aspiration with a 200-0 micropipette tip. The solution was clarified by centrifugation at 15,000×g for 10 min, and the supernatant was used for subsequent immunopurification.

Example 2

Antibody to Human SOD-1

Two rabbits were both immunized with four injections (at 3-week intervals) of 1.5 mg of human erythrocyte SOD-1 (hSOD-1) (Sigma-Aldrich) plus TiterMax® Gold Adjuvant (Sigma-Aldrich). Anti-hSOD-1 antibody was affinity-purified using 15 mg of hSOD-1 permanently coupled to a gel affinity column (Pierce) following the manufacturer's instructions, except for the addition of 2 M sodium citrate during the coupling step. During coupling optimization, citrate was found to increase coupling efficiency, and 2 M was found to be the optimal citrate concentration. Because the antibody was purified by affinity to SOD-1, it was likely a mixture of different antibody classes. Further characterization of the antibody revealed that it was able to pull down metallated copper/zinc SOD-1, as well as all post-translational modifications present in the original SOD-1 antigen, including modification of SOD-1 by 1-7 oxygen atoms. The antibody was also able to deplete>90% of SOD-1 from erythrocyte lysates and homogenized spinal cord samples, where depletion was judged by Western blotting using a commercial SOD-1 antibody (SOD-100 Stressgen, Victoria, BC, Canada).

Example 3

Purification of SOD-1 and Mass Spectrometry

Isolation of hSOD-1 was performed using affinity-purified anti-hSOD-1 polyclonal antibody that was permanently coupled to Ultralink Biosupport medium (Pierce) following the manufacturer's instructions. Microcolumns of these beads were prepared in pipette tips containing frits (SDR Molecular, Sydney, Australia). For immunopurification, the lysed erythrocyte supernatant was passed and repassed over the column five times. Columns were washed with 40 volumes of 10 mM ammonium bicarbonate, pH 8.0, and SOD-1 was eluted with five volumes of 5% acetic acid directly into two volumes of 10% ammonium hydroxide, making the final pH 8.0. Samples were solvent-exchanged into high pressure liquid chromatography-grade water by centrifugal ultrafiltration (10 kDa) (Centricon, Millipore Corporation, Mississauga, ON, Canada) for direct infusion into the mass spectrometer. Western blot analysis using commercial anti-human (S100) or anti-mouse (S101) antibodies (Stressgen Bioreagents Corporation, Victoria, BC, Canada) confirmed that >95% of the immunoreactive SOD-1 was removed from erythrocyte lysates of SOD-1wt transgenic mouse or human blood samples. The entire immunopurification protocol was completed in 20 min, reducing the likelihood of artifactual oxidation. In addition, the presence of modifications in vivo was confirmed by conducting the entire procedure of erythrocyte lysis, immunopurification, and digestion in a sub-parts/million O2 anaerobic glove-box, with samples kept in anaerobic gas-tight syringes until electrosprayed.

Example 4

Identification of SOD-1 Modifications

Immunopurified intact proteins were infused directly into an MDS-Sciex QSTAR® Pulsar or micromass Q-TOF II high performance liquid chromatography (LC) mass spectrometer. All LC-MS analyses took place using endoproteinase GluC-digested SOD-1, as previously described, and injected into an Agilent 1100 nanoflow coupled to a QSTAR® in data-dependent acquisition mode, where the most abundant LC peak at any given time was subject to isolation and collision-activated dissociation (CAD). Kurahashi, T., Miyazaki, A., Suwan, S., and Isobe, M. (2001) J. Am. Chem. Soc. 123, 9268-9278; and Papayannopoulous, I. A. (1995) Mass Spectrom. Rev. 14, 49-73. MS/MS data were correlated to the protein sequence using MASCOT, and data were inspected manually. In this way, endoproteinase-digested fragments for the entire primary sequence of SOD-1 were accounted for. Modifications discovered at the whole-protein level (for example 16 Da, or one oxygen; see FIG. 8) were used to interrogate the LC-MS data. For example, when oxidative modification by 16 Da was observed in the intact protein, endoproteinase peptide data were searched for peptides that were potentially modified by 16 Da (see FIG. 9B). Putative modified peptides were then subjected to subsequent LC-MS/MS analyses, and the amino acid sequence and sites of modification were derived from CAD data. The crystal structure from the Protein Data Bank (code 1 SPD [PDB]) was used to illustrate modifications, with its surface rendered in gray using PyMOL software. Deng, H. X., Hentati, A., Tainer, J. A., Iqbal, Z., Cayabyab, A., Hung, W. Y., Getzoff, E. D., Hu, P., Herzfeldt, B., and Roos, R. P. (1993) Science 261, 1047-1051.

Example 5

Spinal Cord-Dorsal Root Ganglion Cultures

Dissociation of spinal cord-dorsal root ganglia from embryonic day 13 CD 1 mice (Charles River Laboratories, Wilmington, Mass.), plating on poly-D-lysine-coated coverslips, culture media, and identification of motor neurons were as previously described. Roy, J., Minotti, S., Dong, L., Figlewicz, D. A., and Durham, H. D. (1998) J. Neurosci. 18, 9673-9684. Cultures were used 3-6 weeks after plating.

Example 6

Expression of SOD-1 Variants in Motor Neurons

Subcloning of SOD-1G93A and SOD-1 wt cDNAs into the BamHI/HindIII sites of pcDNA3 (Invitrogen) was performed previously using cDNAs provided by Dr. Denise Figlewicz (University of Michigan, Ann Arbor, Mich.). Wang, J., Xu, G., and Borchelt, D. R. (2002) Neurobiol. Dis. 9, 139-148. Trp 4 Phe (W32F) mutations were created by site-specific mutagenesis of SOD-1 G93A and SOD-1 wt (TOP Gene Technologies, Quebec, Canada), producing SOD-1 W32F/G93A and SOD-1 W32F mutants, respectively. Intranuclear microinjection of plasmids was used to express SOD-1 constructs in motor neurons and to assess their effects on the survival and formation of inclusions as previously described Durham, H. D., Roy, J., Dong, L., and Figlewicz, D. A. (1997) J. Neuropathol. Exp. Neurol. 56, 523-530.

For viability experiments, motor neurons containing the co-injected fluorescent marker were counted daily under epi-fluorescence microscopy beginning 24 h post-microinjection. The number of motor neurons was expressed as a percentage of those present at 24 h to exclude those dying from injury during microinjection. The morphology of each cell was also evaluated by phase microscopy. All experiments involved a minimum of six cultures per condition with 20-80 motor neurons (average of 40) analyzed per culture. All experimental groups were analyzed simultaneously using cultures from the same batch, but each set of conditions was assessed for reproducibility in more than one culture batch. For viability experiments, injectates were coded by an independent researcher, and cell counts for viability were carried out blind to the identity of the experimental condition. Rates of cell death were calculated by a linear curve fit of the data (see FIG. 11) and are expressed as the percentage of death/day. The lowest observed linear regression r2 value was 0.94, and the average value was 0.96.

Example 7

Immunocytochemistry and Imaging

To visualize protein expression and localization, spinal cord cultures were fixed with 3% paraformaldehyde in PBS, pH 7.3, for 10 min and permeabilized in 0.5% Nonidet P-40/PBS for 1 min followed by additional fixation in 3% paraformaldehyde/PBS for 2 min. Immunocytochemistry with SOD-1 monoclonal antibody (1:300, clone SD-G6, Sigma-Aldrich) was carried out by incubating for 30 min using bovine serum albumin to block nonspecific binding and Alexa-Red 594-conjugated anti-mouse IiG (Molecular Probes Inc., Eugene, Oreg.). Coverslips were mounted onto glass slides using Immu-mount (Fisher Scientific Company, Ottawa, ON, Canada), and images were captured using a Zeiss LSM 510 confocal microscope and compatible software (Carl Zeiss Canada Ltd., Toronto, ON, Canada).

Example 8

Statistical Analysis

For the survival assays, statistical significance was determined using analysis of variance between groups (SigmaStat, Systat Software, Inc., Point Richmond, Calif.). Significance was established at p less than or equal to 0.05. Data for percentage of motor neurons with inclusions were tested for normal distribution and then compared using a one-tailed, two-sample t test for equal means under the assumption of unequal variance. A null hypothesis of equal means was rejected when p is less than or equal to 0.05.

Example 9

Preparation of Cell Lines for Proteasome Activity-Based Screening Assays pcDNA-3 vector with wild-type SOD-1, G93A SOD-1, W32F SOD-1, W32F G93A SOD-1 cDNA sequence were prepared by standard site-directed mutagenesis techniques. The sequences were determined for each construct and are listed in FIG. 2-6. NIH/3T3 cells were maintained in Dulbecco's modified Eagle's medium (ATCC, Mannassas, Va.) supplemented with 10% newborn calf serum (Invitrogen, Carlsbad, Calif.). Cells were transfected with the plasmids using Lipofectamine 2000 (Invitrogen, Carlsbad, Calif.). A mock transfection was performed and cells were transfected under the same conditions but using either empty pcDNA-3 expression vector or no vector (to test the efficiency of selection). Five hours after transfection medium was changed. 24 hours after transfection cells were diluted to allow for single colony selection. 48 hours after transfection Geneticin (ATCC, Mannassas, Va., final conc. 0.5 mg/mL) was added for selection of stable cell lines. For each construct (individual fALS mutants) 30 individual clones were isolated and grown, and six SOD-1 clones were selected for each construct.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating a neurodegenerative disease, comprising the step of administering to a patient in need thereof a therapeutically effective amount of a compound of formula I, III, IV, V, VI, VII, VIII, IX, X, or XI, or a pharmaceutically acceptable salt thereof, wherein
the neurodegenerative disease is Alzheimer's disease, Parkinson's disease, or Amyotrophic lateral sclerosis;
the compound of formula I is represented by:

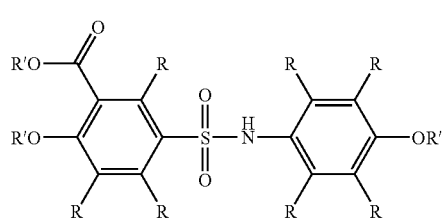

wherein, independently for each occurrence, R is hydrogen or lower alkyl; and R' is hydrogen or lower alkyl;
the compound of formula III is represented by:

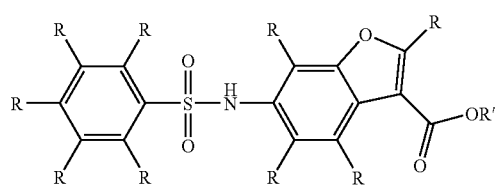

wherein, independently for each occurrence, R is hydrogen or lower alkyl; and R' is hydrogen or lower alkyl;
the compound of formula IV is represented by:

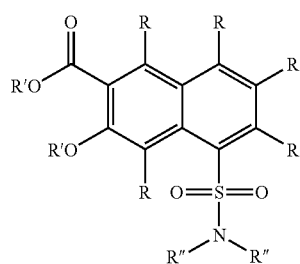

wherein, independently for each occurrence, R is hydrogen or lower alkyl; R' is hydrogen or lower alkyl; and R" is hydrogen, lower alkyl, or the two occurrences of R" taken together are —CH$_2$[CH$_2$]$_2$CH$_2$—, —CH$_2$[CH$_2$]$_3$CH$_2$—, —CH$_2$[CH$_2$]$_4$CH$_2$— or —CH$_2$[CH$_2$]$_5$CH$_2$—;

the compound of formula V is represented by:

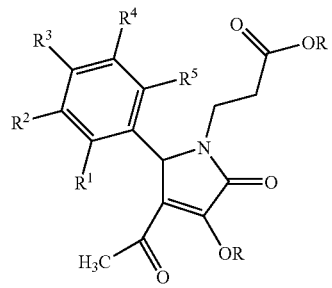

wherein, independently for each occurrence, R is hydrogen or lower alkyl; R$^1$ is hydrogen or lower alkyl; R$^2$ is hydrogen, nitro or lower alkyl; R$^3$ is hydrogen or lower alkyl; R$^4$ is hydrogen or lower alkyl; and R$^5$ is hydrogen or lower alkyl;
the compound of formula VI is represented by:

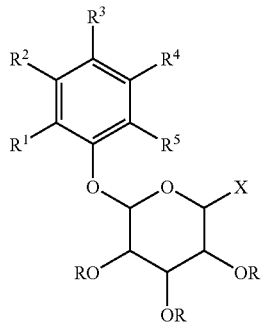

wherein, independently for each occurrence, X is hydrogen or —CH$_2$OR; R is hydrogen or lower alkyl; R$^1$ is hydrogen or lower alkyl; R$^2$ is hydrogen or lower alkyl; R$^3$ is hydrogen, lower alkyl, —Cl, —OR, or NR$_2$; R$^4$ is hydrogen or lower alkyl; and R$^5$ is hydrogen, —Cl, or lower alkyl;
the compound of formula VII is represented by:

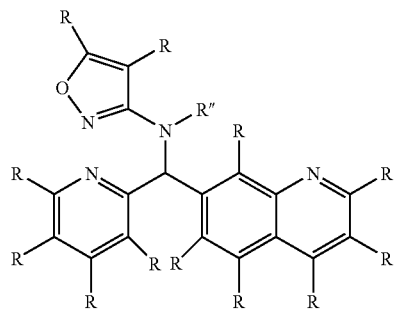

wherein, independently for each occurrence, R is hydrogen or lower alkyl; and R" is hydrogen or lower alkyl; the compound of formula VIII is represented by:

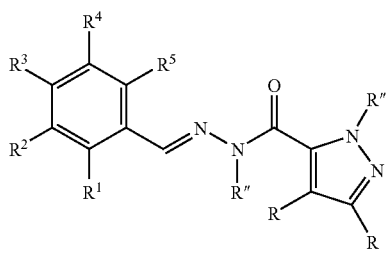

VIII wherein, independently for each occurrence, R is hydrogen or lower alkyl; R" is hydrogen or lower alkyl; $R^1$ is hydrogen or lower alkyl; $R^2$ is hydrogen or lower alkyl; $R^3$ is hydrogen, lower alkyl, —Cl, or —OR; $R^4$ is hydrogen, lower alkyl, —Cl, or —OR; and $R^5$ is hydrogen, —Cl, or lower alkyl;
the compound of formula IX is represented by:

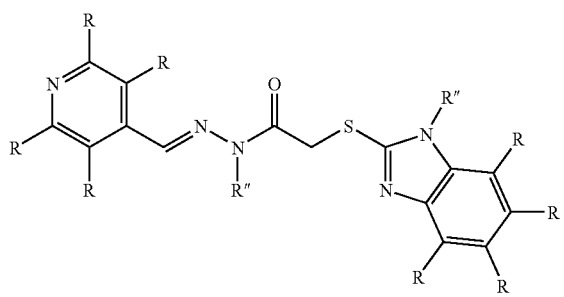

IX wherein, independently for each occurrence, R is hydrogen or lower alkyl; and R" is hydrogen or lower alkyl;
the compound of formula X is represented by:

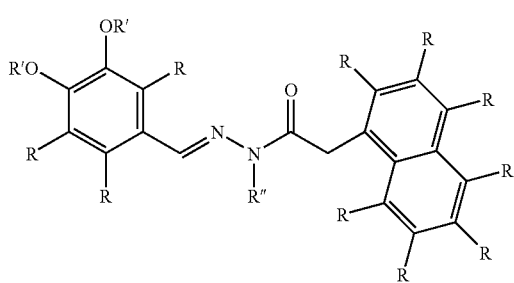

X wherein, independently for each occurrence, R is hydrogen or lower alkyl; R' is hydrogen or lower alkyl; and R" is hydrogen or lower alkyl; and
the compound of formula VI is represented by:

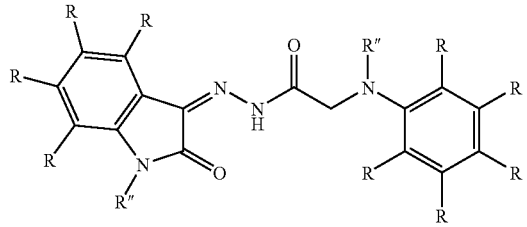

XI wherein, independently for each occurrence, R is hydrogen or lower alkyl; and R" is hydrogen or lower alkyl.

2. The method of claim 1, wherein the compound is

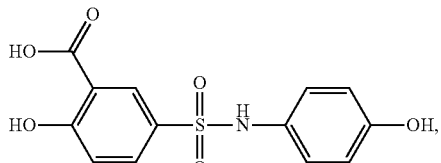

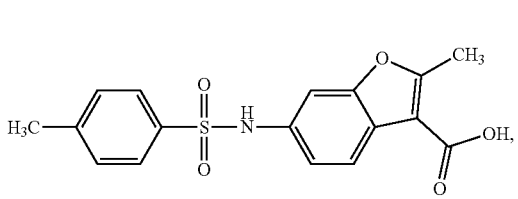

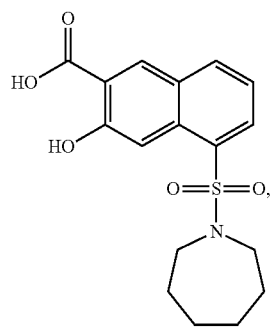

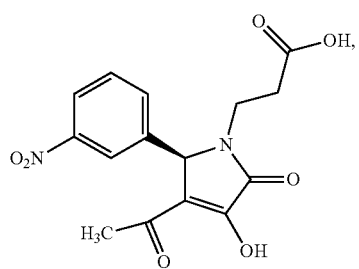

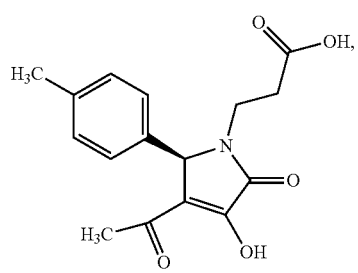

-continued

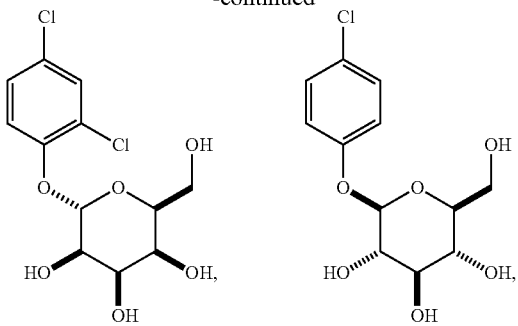

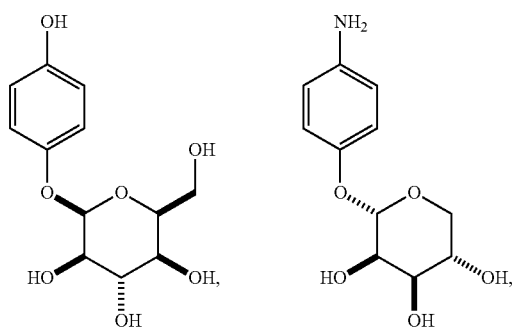

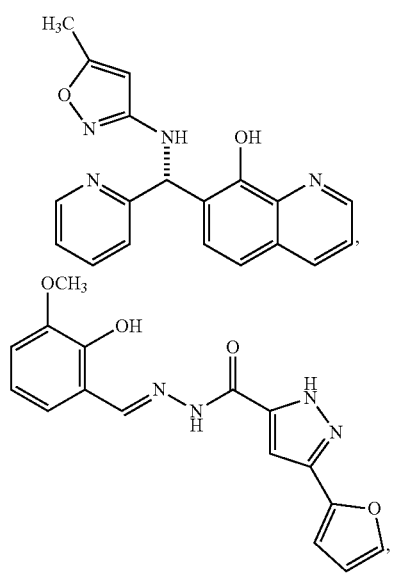

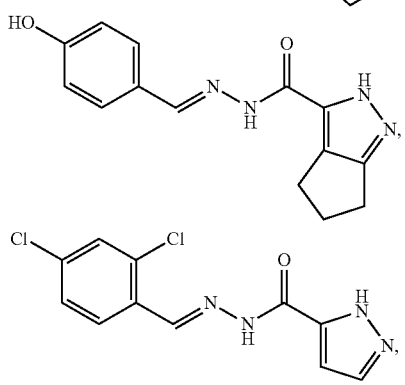

-continued

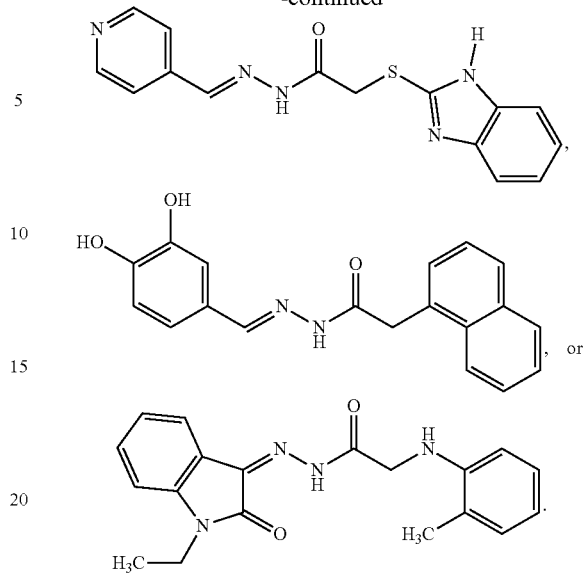

3. A method of treating a neurodegenerative disease, comprising the step of administering to a patient in need thereof a therapeutically effective amount of a compound selected from the group consisting of 2-(2,4-dichlorophenoxy)-6-(hydroxymethyl)oxane-3,4,5-triol; 3-[3-acetyl-4-hydroxy-2-(4-methylphenyl)-5-oxo-2H-pyrrol-1-yl]propanoate; 2-hydroxy-5-[(2-pyridin-2-ylsulfanylacetyl)amino]benzoate; (2S,3R,4R,5S,6R)-2-(hydroxymethyl)-6-(4-hydroxyphenoxy)oxane-3,4,5-triol; (2S,3R,4R,5S)-2-(4-aminophenoxy)oxane-3,4,5-triol; 2-hydroxy-5-[(4-hydroxyphenyl)sulfamoyl]benzoate; 3-[3-acetyl-2-(3-nitrophenyl)-4,5-dioxopyrrolidin-1-yl]propanoate; (2R,3R,4S,5S,6S)-2-(4-chlorophenoxy)-6-(hydroxymethyl)oxane-3,4,5-triol; 2-[2-(1-benzofuran-2-yl)-2-oxoethyl]sulfanyl-1H-quinazolin-4-one; 5-(2-furanyl)-N-[(2-hydroxy-3-methoxyphenyl)methylideneamino]-1H-pyrazole-3-carboxamide; 2-(1H-benzimidazol-2-ylsulfanyl)-N-(pyridin-4-ylmethylideneamino)acetamide; 2-methyl-5-[(4-methylphenyl)sulfonylamino]-1-benzofuran-3-carboxylic acid; N-[(3,4-dihydroxyphenyl)methylideneamino]-2-naphthalen-1-ylacetamide; 7-[[(5-methyl-1,2-oxazol-3-yl)amino]-pyridin-2-ylmethyl]quinolin-8-ol; 5-(azepan-1-ylsulfonyl)-3-hydroxynaphthalene-2-carboxylate; 2-[(2-methylphenyl)amino]-N-[(1-ethyl-2-oxoindol-3-ylidene)amino]acetamide; N-[(4-hydroxyphenyl)methylideneamino]-1,4,5,6-tetrahydrocyclopenta[d]pyrazole-3-carboxamide; and N-[(2,4-dichlorophenyl)methylideneamino]-2H-pyrazole-3-carboxamide;
wherein the neurodegenerative disease is Alzheimer's disease, Parkinson's disease, or Amyotrophic lateral sclerosis.

4. The method of claim 1, wherein the neurodegenerative disease is Amyotrophic lateral sclerosis.

5. The method of claim 3, wherein the neurodegenerative disease is Amyotrophic lateral sclerosis.

6. The method of claim 1, wherein the compound of formula I, III, IV, V, VI, VII, VIII, IX, X, or XI binds at or adjacent to a SOD-1 Trp32.

7. The method of claim 3, wherein the compound binds at or adjacent to a SOD-1 Trp32.

8. The method of claim 1, wherein the compound of formula I, III, IV, V, VI, VII, VIII, IX, X, or XI binds at or adjacent to a SOD-1 Trp32; and the SOD-1 Trp32 is oxidized.

9. The method of claim 3, wherein the compound binds at or adjacent to a SOD-1 Trp32; and the SOD-1 Trp32 is oxidized.

* * * * *